US012698516B2

(12) United States Patent
Geissler et al.

(10) Patent No.: US 12,698,516 B2
(45) Date of Patent: Aug. 4, 2026

(54) PRODUCTION OF CANNABINOIDS/PHYTOCANNABINOIDS WITH A PLANT EXTRACT

(71) Applicant: Technische Universität Darmstadt, Darmstadt (DE)

(72) Inventors: Marcus Geissler, Höchst im Odenwald (DE); Lisa Niederreiter, Freiburg (DE); Heribert Warzecha, Darmstadt (DE)

(73) Assignee: Technische Universität Darmstadt, Darmstadt (DE)

( * ) Notice: Subject to any disclaimer, the term of this patent is extended or adjusted under 35 U.S.C. 154(b) by 391 days.

(21) Appl. No.: 18/036,725

(22) PCT Filed: Nov. 11, 2021

(86) PCT No.: PCT/EP2021/081309
§ 371 (c)(1),
(2) Date: May 12, 2023

(87) PCT Pub. No.: WO2022/101306
PCT Pub. Date: May 19, 2022

(65) Prior Publication Data
US 2025/0263761 A1 Aug. 21, 2025

(30) Foreign Application Priority Data
Nov. 12, 2020 (EP) .................................... 20207220

(51) Int. Cl.

| | |
|---|---|
| ***C12P 17/06*** | (2006.01) |
| ***C12N 9/02*** | (2006.01) |
| ***C12N 9/10*** | (2006.01) |
| ***C12P 7/22*** | (2006.01) |
| ***C12P 7/42*** | (2006.01) |

(52) U.S. Cl.
CPC .............. *C12P 17/06* (2013.01); *C12N 9/001* (2013.01); *C12N 9/1085* (2013.01); *C12P 7/22* (2013.01); *C12P 7/42* (2013.01); *C12Y 103/03* (2013.01); *C12Y 121/03007* (2015.07); *C12Y 121/03008* (2015.07); *C12Y 205/01011* (2013.01)

(58) Field of Classification Search
None
See application file for complete search history.

(56) References Cited

U.S. PATENT DOCUMENTS

2019/0225975 A1* 7/2019 Rushton ............... C12N 9/0004
2022/0154197 A1* 5/2022 Hofenk ................ C07K 14/415

FOREIGN PATENT DOCUMENTS

WO WO 2018057385 A2 9/2017
WO WO 2020182866 A1 9/2020

OTHER PUBLICATIONS

Accession CDI30233. Jan. 7, 2014 (Year: 2014).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Thies Gülck, et al, "Synthetic biology of cannabinoids and cannabinoid glucosides in Nicotiana benthamiana and *Saccharomyces cerevisiae*", J. Nat. Prod., 2020, 83, 2877-2893.
Bastian Zirpel, et al., "Engineering yeasts as platform organisms for cannabinoid biosynthesis", J. Biotechnol., 2017, 259, 204-212.
Xiaozhou Luo, et al., "Complete biosynthesis of cannabinoids and their unnatural analogues in yeast", Nature, 2019, 567, 123-126.

* cited by examiner

*Primary Examiner* — Christian L Fronda
(74) *Attorney, Agent, or Firm* — Grimes & Yvon LLP

(57) ABSTRACT

The present invention relates to a process for the production of a compound of Formula (I), wherein the process comprises the step of reacting a plant extract having prenyltransferase activity with a compound of Formula (II) and geranyl pyrophosphate (GPP) having Formula (III) to produce the compound of Formula (I), wherein the plant extract is not a plant extract obtainable from a plant that naturally produces cannabinoids/phytocannabinoids. Accordingly, the present invention relates to a process for the production of a compound of Formula (I), wherein the process comprises the step of reacting a plant extract having prenyltransferase activity with a compound of Formula (II) and geranyl pyrophosphate (GPP) having Formula (III) to produce the compound of Formula (I), wherein the plant extract is not *Cannabis sativa* plant extract. Further, the present invention relates to the process for the production of a compound of Formula (IV), wherein the process comprises producing a compound of Formula (I) by the process as described herein and converting the compound of Formula (I) to the compound of Formula (IV) in the presence of the tetrahydrocannabinolic acid synthase (THCAS; EC 1.21.3.7). The present invention also relates to a process for the production of a compound of Formula (V) wherein the process comprises producing a compound of Formula (I) by the process as described herein and converting the compound of Formula (I) to a compound of Formula (V) in the presence of the THCAS (EC 1.21.3.7), cannabidiolic acid synthase (CBDAS; EC 1.21.3.8) and/or cannabichromenic acid synthase (CBCAS; EC 1.3.3.-). Further, the present invention relates to a process for the production of a compound of Formula (VI) wherein the process comprises producing a compound of Formula (I) by the process as described herein and converting the compound of Formula (I) to a compound of Formula (VI) in the presence of the CBDAS (EC 1.21.3.8).

12 Claims, 8 Drawing Sheets

Specification includes a Sequence Listing.

PRODUCTION OF CANNABINOIDS/PHYTOCANNABINOIDS WITH A PLANT EXTRACT

CROSS-REFERENCE TO RELATED APPLICATIONS

This application is a National Stage of International Application No. PCT/EP2021/081309, filed on Nov. 11, 2021, which claims the benefit of priority to European Patent Application No. 20207220.3, filed on Nov. 12, 2020, the entireties of both of which are herein incorporated by reference.

SEQUENCE LISTING

This application contains a Sequence Listing which has been submitted electronically in ASCII format and is hereby incorporated by reference in its entirety. Said ASCII copy, created on Nov. 20, 2023, is named VOS_005_US1-Replacement_Sequence_Listing.txt and is 16,118 bytes in size.

BACKGROUND

Figure 1:
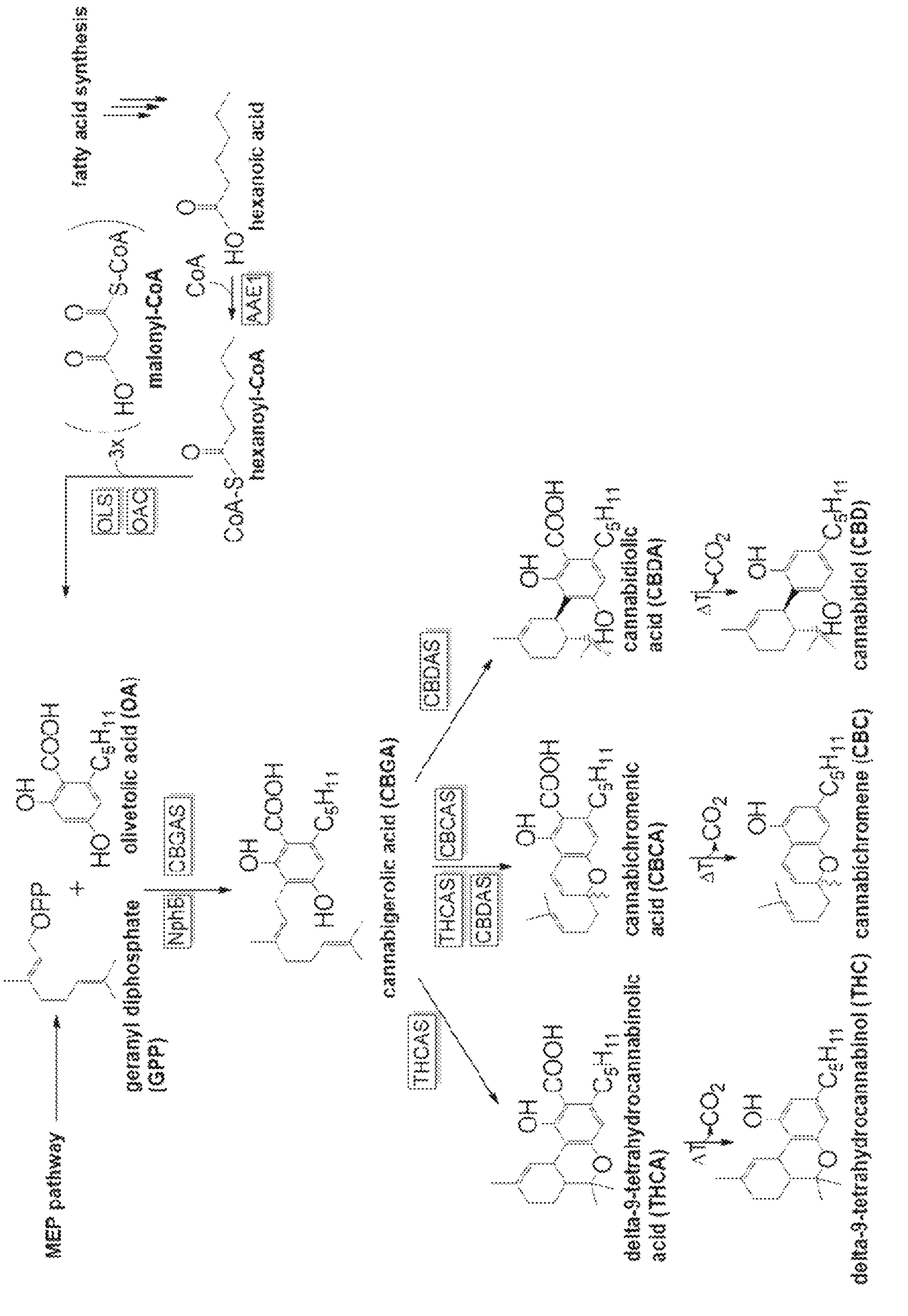

*Cannabis sativa* is one of the oldest domesticated crops and has been used for thousands of years as a supplier of textile fibers, as an oil producer or for its therapeutic effects (Russo et al., J Exp Bot. (2008), 59 (15): 4171-4182). *Cannabis sativa* has also been investigated for the presence of its plant-derived natural compounds, the so-called phytocannabinoids. Due to its versatile applications and new medical knowledge of the effects of phytocannabinoids on the human endocannabinoid acting on CB1 and CB2 receptors (De Petrocellis et al., Br J Pharmacol. (2011), 163 (7): 1479-94). *Cannabis sativa* has recently gained renewed interest: Among other things, because of its use for the production of bioplastics (Marsh, Mater Today. (2003), 6:36-43), but mainly because of its enormous pharmaceutical potential. Thus, *Cannabis sativa*'s phytochemical portfolio includes the aforementioned phytocannabinoids, which, with more than 100 different compounds in ten subclasses, make up a large group of ingredients (EISohly and Slade, Life Sci. (2005), 78:539-548; Radwan et al., J Nat Prod. (2009), 72:906-911; Fischedick et al., Phytochemistry (2010), 71:2058-2073). The most important cannabinoids/phytocannabinoids represented in *Cannabis sativa* are the psychoactive tetrahydrocannabinol (THC) as well as the non-psychotropic cannabinoids cannabidiol (CBD) and cannabichrome (CBC). The biosynthesis pathway for the production of the cannabinoids THC, CBC and CBD from the substrates olivetolic acid (OA) and geranyl pyrophosphate (GPP) in *Cannabis sativa* is shown in FIG. 1 (Figure modified from Schachtsiek et al., Planta Med. (2018), 84 (4): 214-220). The biosynthesis of the cannabinoids/phytocannabinoids in *Cannabis sativa* can generally be divided into (i) a monoterpene producing part (production of geranyl pyrophosphate (GPP) via the methylerythritol phosphate (MEP) pathway, localized in the chloroplasts, (ii) the olivetolic acid (OA) producing part starting from fatty acid synthesis and (iii) the actual cannabinoid-producing part. The hexanoic acid originating from the fatty acid metabolism is first converted to the active CoA thioester (hexanoyl-CoA) by the acyl-activating enzyme 1 (AAE1). OA is then formed from three molecules of malonyl-CoA and one molecule of hexanoyl-CoA by aldol condensation, catalyzed by the enzymes olivetol synthase (OLS) and olivetolic acid cyclase (OAC). The general precursor for the synthesis of further cannabinoids, cannabigerolic acid (CBGA), is subsequently produced by prenylation of the OA by means of membrane-bound cannabigerolic acid synthase (CBGAS) through the GPP provided by the MEP pathway. Finally, the different cannabinoids tetrahydrocannabinolic acid (THCA), cannabidiolic acid (CBDA) and cannabichromenic acid (CBCA) are formed by stereoselective cyclizing the terpene unit of CBGA by the respective enzymes tetrahydrocannabinolic acid synthase (THCAS), cannabidiolic acid synthase (CBDAS) and cannabichromenic acid synthase (CBCAS; Zirpel et al., J Biotechnol. (2017), 259:204-212 2017).

Cannabinoids are described to be unique terpenophenolic matabolites found only in *Cannabis sativa* (Sirikantaramas and Taura, Springer (2017), 1st edition, Chapter 8, p. 183-206). Alternative cannabinoid-like substances or cannabimimetic compounds can not only be found in *Cannabis sativa*, but also in other plant species including *Acmella oleracea* (Dallazan et al., Inflammopharmacology (2019), 28:175-186), *Echinaceae angustifolia* (Raduner et al., J Biol Chem. (2006), 281 (20): 14192-14206), *Echinaceae purpurea* (Raduner et al., J Biol Chem. (2006), 281 (20): 14192-14206), *Helichrysum umbraculigerum* (Pollastro et al., Fitoterapia (2018), 126:35-39), *Heliopsis helianthoides* (Hajdu et al., J Nat Prod. (2014), 77 (7): 1663-9), *Lepidium meyenii* (Hajdu et al., J Nat Prod. (2014), 77 (7): 1663-9), *Piper methysticum* (Ligresti et al., Pharmacol Res. (2012), 6 (2): 163-169), *Piper nigrum* (Reynoso-Moreno et al., J Agric Food Chem. (2017), 65 (43): 9435-9442), *Radula marginata* (Hussain et al., Phytochem rev. (2019), 18:953-965), *Radula perrottetii* (Chicca et al., Neurophysiol. (2018), 4 (10)), *Rhododendron anthopogonoides* (Iwata and Kitanaka, Chem Pharm Bull. (2011), 59 (11): 1409-12) and *Tuber melanosporum* (Degenhardt et al., Biology, Pharmacology, Diagnosis, and Treatment (2017), Chapter 2, p. 13-23), (Pacioni et al., Phytochemistry (2015), 110:104-10).

The cannabinoid/phytocannabinoid production by using *Cannabis sativa* is generally hampered by its legal scheduling, the low in planta abundances of nearly all of the known cannabinoids, and the structural complexity of the cannabinoids, which limits bulk chemical synthesis (Luo et al., Nature. (2019), 567:123-126). Since engineering of cannabinoid biosynthesis is furthermore thought to enable the flux of the pathway towards desired target products, for instance towards the formation of pharmacologically attractive non-psychotropic cannabinoids, heterologous production has already been investigated in previous studies. However, a decisive limitation for heterologous cannabinoid production is the sufficient formation of the central intermediate CBGA, which is, as described previously, in *Cannabis sativa* produced by the geranyl diphosphate: olivetolate geranyltransferase CBGAS. The enzyme CBGAS was first identified by Fellermeier and Zenk (Fellermeier and Zenk., FEBS Lett. (1998), 427 (2): 283-5) by using crude homogenates from *Cannabis sativa* leaves as source to biochemically characterize the enzyme. Prenyltransferase activity was determined by contacting the plant extract of *Cannabis sativa* with OA and GPP and measuring product formation of CBGA. Prenyltransferase enzymes have been identified in various plant species, however, besides the prenyltransferase from *Cannabis sativa*, none of the identified plant enzymes has been described to show substrate specificity towards OA (de Bruijn et al., Trends Biotechnol. (2020), 38 (8): 917-934). Furthermore, all known sequences of plant aromatic prenyltransferases were shown to belong to membrane-bound enzymes (Degenhardt et al., (2017), Biology, Pharmacology, Diagnosis, and Treatment, Chapter 2, p. 13-23).

An attempt to enable heterologous cannabinoid production has been made by Luo et al. (Luo et al., Nature. (2019), 567:123-126) by using yeast as heterologous host. Although several enzymes with putative function from *Cannabis sativa* have been described, their functionality is very limited or even non-existent and after testing, Luo et al. describes a CBGAS from *Cannabis sativa* as non-functional in yeast. The group then used a newly identified isoenzyme (CsPT4) from *Cannabis* for the process, yet, resulting in a product yield of 8.0 mg/L, the enzyme conversion rates are not convincing. It was shown that CsPT4 having prenyltransferase activity was capable of producing CBGA analogues from the different fatty acid precursors hexanoic acid, pentanoic acid, heptanoic acid, 4-methylhexanoic acid, 5-hexenoic acid and 6-heptynoic acid which were successfully converted to the corresponding cannabinoid analogues.

Another approach in yeast has been investigated by using bacterial enzymes for the prenyl transfer (Zirpel et al., J Biotechnol. (2017), 259:204-212). Bacterial enzymes usually have a lower specificity than the enzymes from *Cannabis sativa* but are able to prenylate intermediate olivetolic acid (OA) in the 2-position. The enzyme used in this study is the enzyme NphB from *Streptomyces* sp. The study of Zirpel et al. discloses yeast mutants successfully producing CBGA by the functionally active NphB. NphB, therefore, principally has the potential to replace prenyltransferases from *Cannabis sativa* in a biotechnological process (Valliere et al., Nat Commun. (2019), 10; 565). Although NphB has the advantage of being a soluble enzyme, bacterial prenyltransferases still have the disadvantage that they preferably produce products like 2-O-geranyl olivetolic acid, while producing the desired CBGA only as side product.

Furthermore, *Nicotiana benthamiana* has been investigated as heterologous host for the production of cannabinoids (Gülck et al., J. Nat. Prod. (2020)). By biotechnological manipulation using *Agrobacterium*-mediated transient expression of the prenyltransferase CsaPT4 from *Cannabis sativa* with concomitant infiltration of OA and GPP, Gülck et al. prove CsaPT4 as functional CBGAS in *Nicotiana benthamiana*. Notably, the chromatograms shown in FIG. 7 of Gülck et al. did not report that a plant extract from *N. benthamiana* has an endogenous prenyltransferase activity: neither CBGA nor any derivatives thereof could be detected in the *N. benthamiana* plant extracts.

Given the numerous therapeutic applications of cannabinoids including the treatment of chronic pain, multiple sclerosis and posttraumatic stress (Wilsey et al., Pain Res. (2016), 31 (9): 587-98; Leocani et al., J neurol. (2015), 262 (11): 2520-7; O'Neil et al., Ann Intern Med. (2017), 167 (5): 332-340), many of these compounds are of high interest. Because so far, the approaches to establish heterologous cannabinoid production were unconvincing in terms of yield and specificity, there is the need to provide new methods for the cost efficient and simple production of cannabinoids to comply with the increasing demand for these compounds.

SUMMARY OF INVENTION

The present invention relates to a process for the production of a compound of Formula (I), wherein the process comprises the step of reacting a plant extract having prenyltransferase activity with a compound of Formula (II) and geranyl pyrophosphate (GPP) having Formula (III) to produce the compound of Formula (I), wherein the plant extract is not a plant extract obtainable from a plant that naturally produces cannabinoids/phytocannabinoids, such as *Cannabis sativa*. Accordingly, the present invention relates to a process for the production of a compound of Formula (I), wherein the process comprises the step of reacting a plant extract having prenyltransferase activity with a compound of Formula (II) and geranyl pyrophosphate (GPP) having Formula (III) to produce the compound of Formula (I), wherein the plant extract is not a *Cannabis sativa* plant extract. Further, the present invention relates to the process for the production of a compound of Formula (IV), wherein the process comprises producing a compound of Formula (I) by the process as described herein and converting the compound of Formula (I) to the compound of Formula (IV) in the presence of the tetrahydrocannabinolic acid synthase (THCAS; EC 1.21.3.7). The present invention also relates to a process for the production of a compound of Formula (V) wherein the process comprises producing a compound of Formula (I) by the process as described herein and converting the compound of Formula (I) to a compound of Formula (V) in the presence of the THCAS (EC 1.21.3.7), cannabidiolic acid synthase (CBDAS; EC 1.21.3.8) and/or cannabichromenic acid synthase (CBCAS; EC 1.3.3.-). Further, the present invention relates to a process for the production of a compound of Formula (VI) wherein the process comprises producing a compound of Formula (I) by the process as described herein and converting the compound of Formula (I) to a compound of Formula (VI) in the presence of the CBDAS (EC 1.21.3.8).

DETAILED DESCRIPTION

Figure 8:
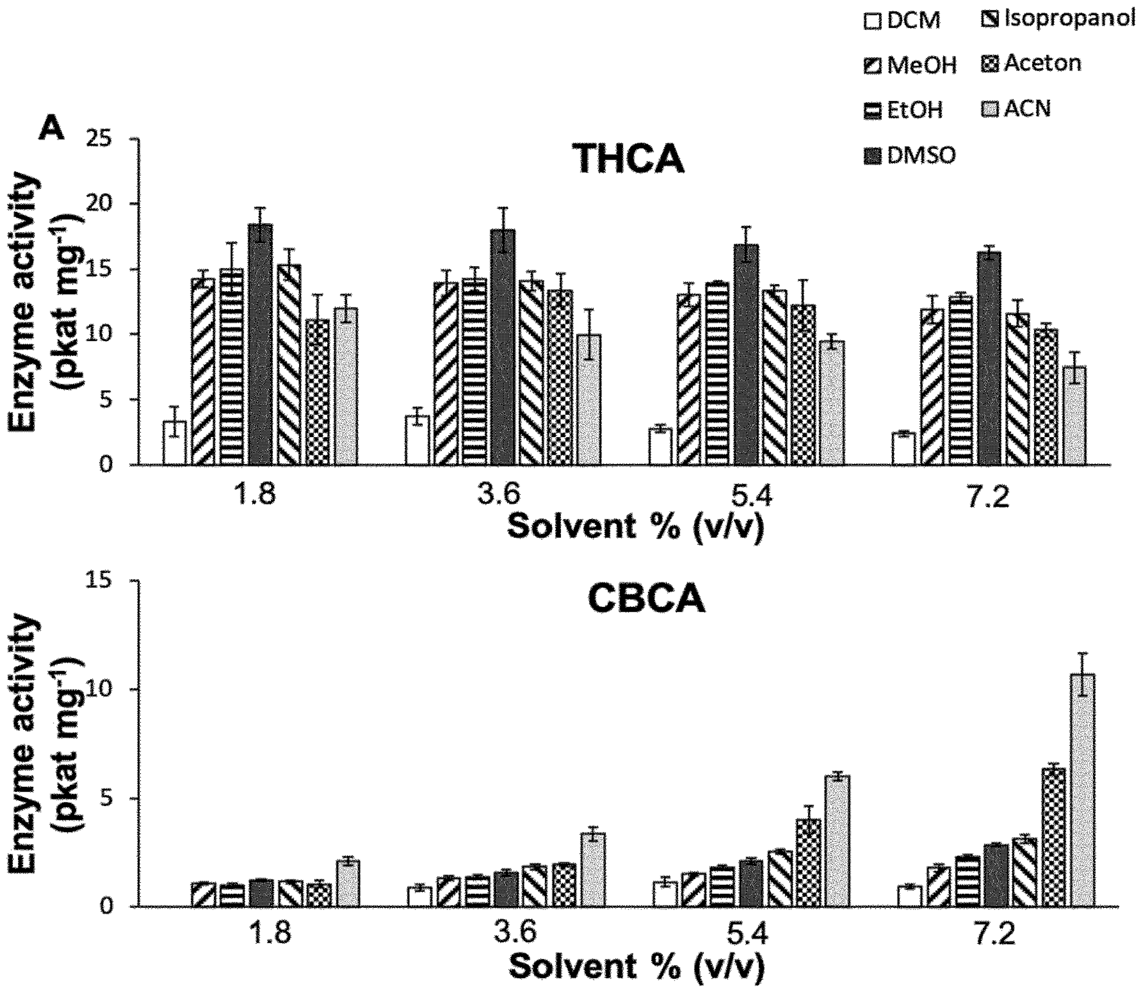
Figure 8:
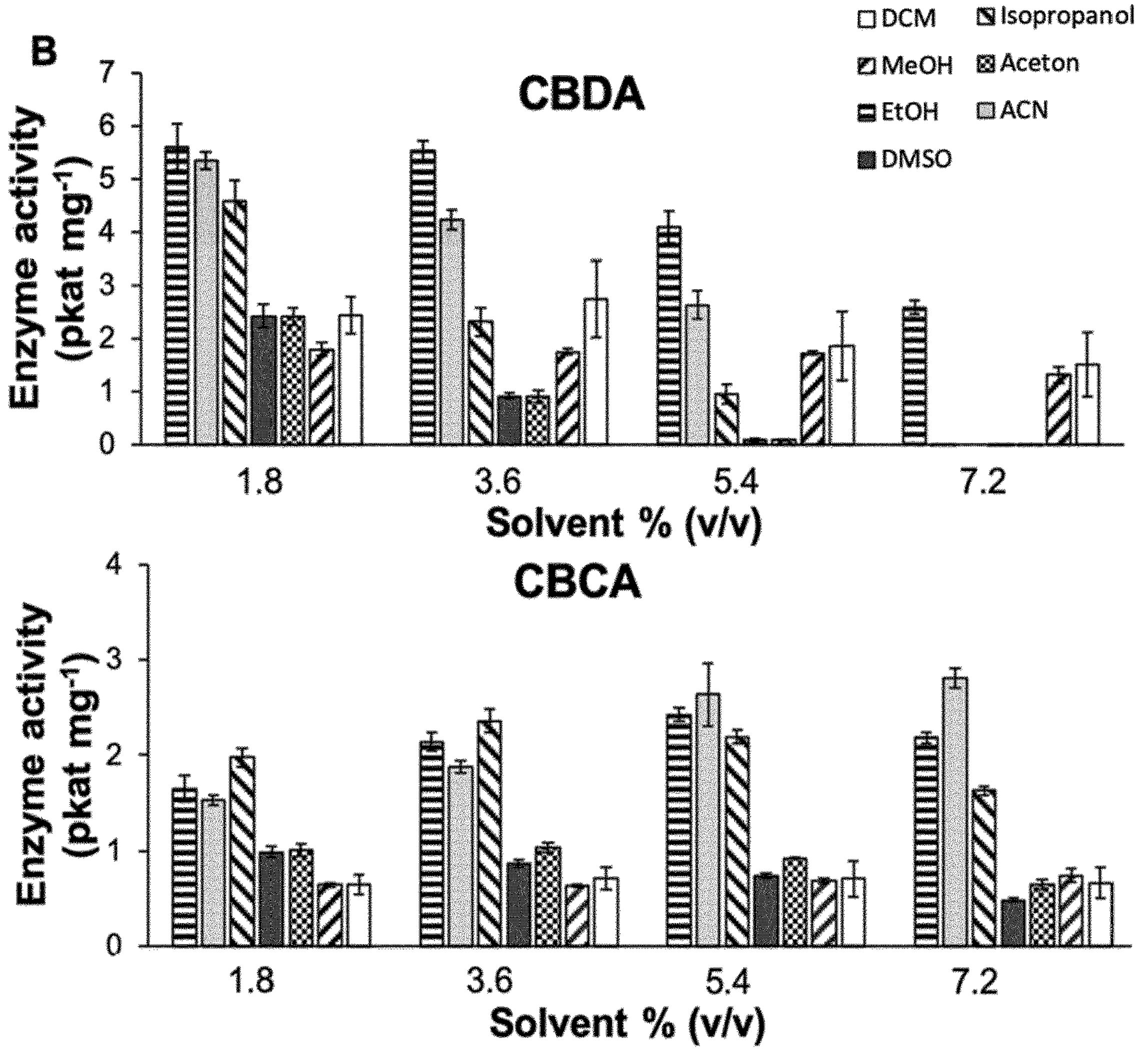
Figure 8:
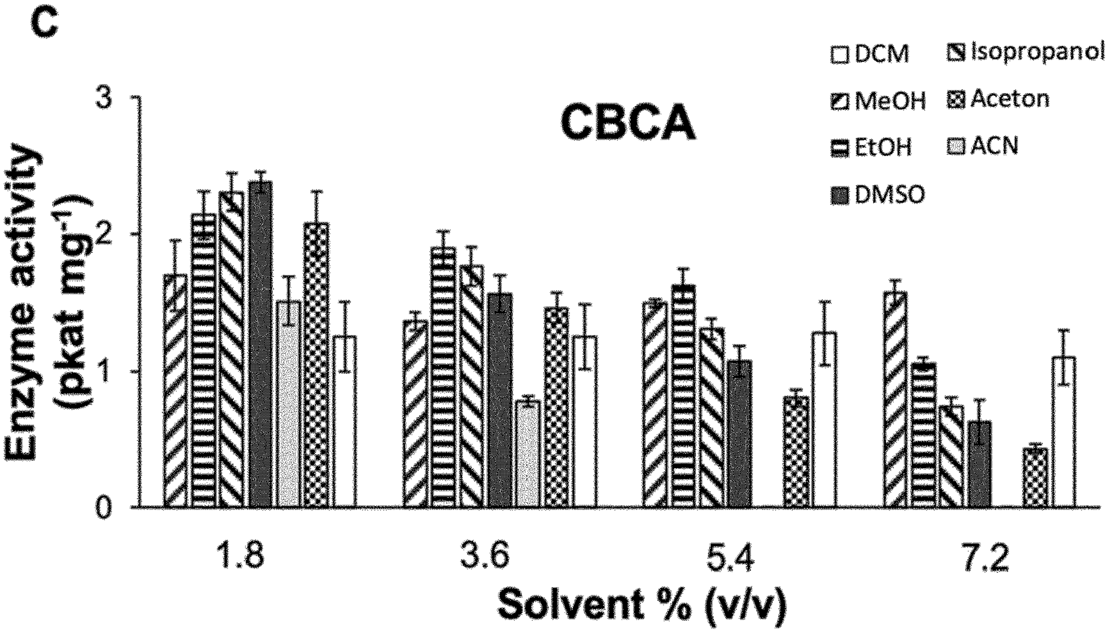
Figure 9:
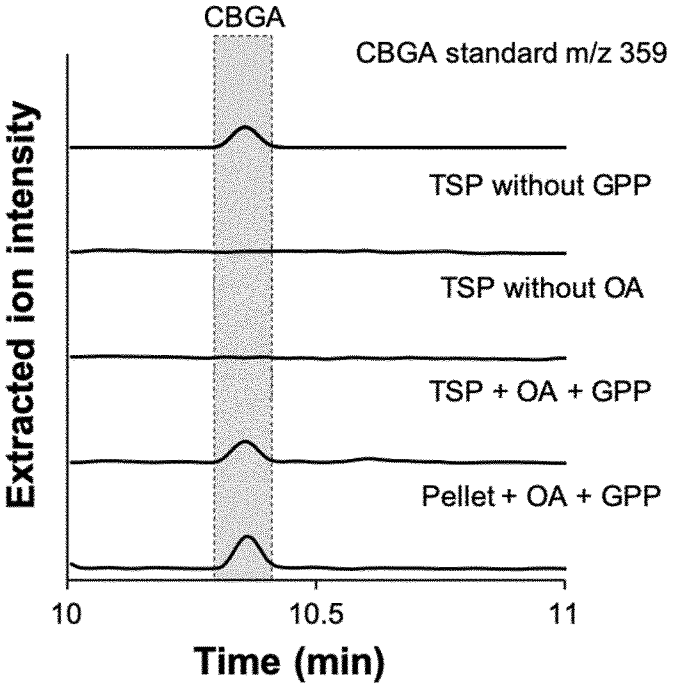

The present invention meets the demand for an alternative process for the production of cannabinoid compounds by utilizing endogenous prenyltransferases occurring in plants which do not naturally produce phytocannabinoids. The present inventors conducted studies showing that the biosynthesis of cannabinoids, like exemplarily shown for the substrates OA and GPP in FIG. 1, can be carried out by using a plant extract, wherein the plant extract is a plant extract derived from/obtainable from a plant that does not naturally produce cannabinoids. As shown in the appended Examples, it was found that a plant extract of *Nicotiana benthamiana*—i.e. a plant that does not endogenously contain or produce cannabinoids—can be used to produce cannabinoids, particularly the central cannabinoid precursor CBGA by the conversion of OA and GPP. Further plants can be used in the process of the invention such as *Lactuca sativa, Nepeta cataria, Nicotiana benthamiana, Nicotiana tabacum* and *Ocimum basilicum*. So far, the capability of producing phytocannabinoids, specifically the central cannabinoid precursor CBGA, has not been described in any other plant than *Cannabis sativa*. Accordingly, the present invention is based on the surprising and unexpected finding that, contrary to the skilled person's knowledge, a plant extract that is not a *Cannabis sativa* plant extract can be used for the production of cannabinoid compounds. As evident from the appended Examples, plant extracts from plants that do not naturally produce phytocannabinoids such as *Nicotiana benthamiana* are characterized by having a prenyltransferase activity eligible to substitute CBGAS from *Cannabis sativa*. For the biotechnological representation this means that neither the CBGAS nor NphB are necessary for the specific prenylation reaction to provide CBGA. This simplifies the genetic modification of a heterologous production system, since genes encoding enzymes showing prenyltransferase activity would not have to be introduced for the production of cannabinoids. As evident from FIGS. 3-5 of the appended Examples, the present invention is directed to a process that allows the production of the central precursor CBGA by using a plant extract, wherein the plant extract is not a *Cannabis sativa* plant extract. Further, CBGA can be further converted into cannabinoids such as THCA, CBDA and CBCA. Furthermore, it has been shown that the process according to the present invention can be manipulated by the addition of organic solvents and by changing their volume ratio in the reaction medium (FIGS. 6 and 8). Such manipulation can specifically favour the production of preferred cannabinoids such as non-psychoactive cannabinoids like CBD. The present invention furthermore provides the advantage that the cannabinoid production process is substantially simplified given that the plant extract having prenyltransferase activity provides, besides membrane-bound prenyltransferases, soluble prenyltransferases (FIG. 9). As described previously, all prenyltransferases in plants have been described to be transmembrane proteins, which are accompanied by a more complex purification process when compared to soluble enzymes.

Accordingly, the present invention relates to a process for the production of a compound of Formula (I), wherein the process comprises the step of reacting a plant extract having prenyltransferase activity with a compound of Formula (II) and geranyl pyrophosphate (GPP) having Formula (III) to produce the compound of Formula (I), wherein the plant extract is not a plant extract that is obtainable from a plant that naturally produces cannabinoids/phytocannabinoids. Cannabinoids synthesized by plants sources are considered to be phytocannabinoids, i.e. plant-based cannabinoids. In the context of the present invention, the term "cannabinoid" may be interchangeably used with "phytocannabinoids". Phytocannabinoids act as ligands to cannabinoid receptors (CB1 and CB2) or share chemical similarity with cannabinoids. Specifically, the plant extract is not a plant extract obtainable from a plant that naturally produces cannabinoids/phytocannabinoids such as *Cannabis sativa*. Accordingly, the present invention relates to a process for the production of a compound of Formula (I), wherein the process comprises the step of reacting a plant extract having prenyltransferase activity with a compound of Formula (II) and geranyl pyrophosphate (GPP) having Formula (III) to produce the compound of Formula (I), wherein the plant extract is not a *Cannabis sativa* plant extract. Furthermore, in the context of the present invention, the plant extract as used in the process disclosed herein is not a plant extract derived from/obtainable from a plant that naturally produces phytocannabinoids, phytocannabinoid-like substances or cannabimimetic compounds. Examples thereof include *Acmella oleracea, Echinaceae* angustifolia, *Echinaceae purpurea, Helichrysum umbraculigerum, Heliopsis helianthoides, Lepidium meyenii, Piper methysticum, Piper nigrum, Radula marginata, Radula perrottetii, Rhododendron anthopogonoides* and *Tuber melanosporum*.

In the present invention, a compound of Formula (I) is considered to have the following structure:

Formula (I)

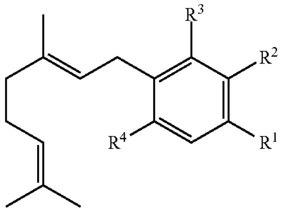

$R^1$ is selected from -hydrogen, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl), -(optionally substituted linear or branched $C_{2-10}$ alkynyl), -(optionally substituted $C_{3-10}$ cycloalkyl), (optionally substituted $C_{6-10}$ aryl), -(optionally substituted linear or branched $C_{1-10}$ alkylene)-(optionally substituted $C_{6-10}$ aryl), -(optionally substituted linear or branched $C_{2-10}$ alkenylene)-(optionally substituted $C_{6-10}$ aryl) and -(optionally substituted linear or branched $C_{2-10}$ alkynylene)-(optionally substituted $C_{6-10}$ aryl). Preferably, $R^1$ is selected from -(optionally substituted linear or branched $C_{1-10}$ alkyl), -(optionally substituted linear or branched $C_{2-10}$ alkenyl) and -(optionally substituted linear or branched $C_{2-10}$ alkynyl). More preferably, $R^1$ is selected from linear or branched $C_{1-10}$ alkyl, linear or branched $C_{2-10}$ alkenyl and linear or branched $C_{2-10}$ alkynyl. Even more preferably, $R^1$ is selected from linear or branched $C_{4-6}$ alkyl. Still more preferably, $R^1$ is a $C_5$ alkyl. Most preferably, $R^1$ is $C_5H_{11}$.

$R^2$ is selected from -hydrogen, —C(O)OH, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl), (optionally substituted linear or branched $C_{2-10}$ alkynyl), -(optionally substituted $C_{3-10}$ cycloalkyl), -(optionally substituted $C_{6-10}$ aryl), -(optionally substituted linear or branched $C_{1-10}$ alkylene)-(optionally substituted $C_{6-10}$ aryl), -(optionally substituted linear or branched $C_{2-10}$ alkenylene)-(optionally substituted $C_{6-10}$ aryl) and -(optionally substituted linear or branched $C_{2-10}$ alkynylene)-(optionally substituted $C_{6-10}$ aryl). Preferably, $R^2$ is selected from -hydrogen, —C(O)OH, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl) and -(optionally substituted linear or branched $C_{2-10}$ alkynyl). Even more preferably, $R^2$ is selected from —C(O)OH, —C(O)-(optionally substituted linear or branched $C_{1-10}$ alkyl) and —C(O)—O-(optionally substituted linear or branched $C_{1-10}$ alkyl). Still more preferably, $R^2$ is selected from —C(O)OH and —C(O)—O-(optionally substituted linear or branched $C_{1-10}$ alkyl). Most preferably, $R^2$ is —C(O)OH.

$R^3$ is selected from —OH, —O-glycosyl, —O($C_{1-6}$ alkyl), -halogen, —SH, —S($C_{1-6}$ alkyl), —$NH_2$, —NH($C_{1-6}$ alkyl), —N($C_{1-6}$ alkyl)$_2$, -piperidyl and -morpholinyl. Preferably, $R^3$ is selected from —OH, —O-glycosyl, —O($C_{1-6}$ alkyl) and -halogen. Even more preferably, $R^3$ is selected from —OH and —O-glycosyl. Still more preferably, $R^3$ is selected from —OH and —O-glucosyl. Most preferably, $R^3$ is —OH.

$R^4$ is selected from —OH, —O-glycosyl, —O($C_{1-6}$ alkyl), -halogen, —SH, —S($C_{1-6}$ alkyl), —$NH_2$, —NH($C_{1-6}$ alkyl), —N($C_{1-6}$ alkyl)$_2$, -piperidyl and -morpholinyl. Preferably, $R^4$ is selected from —OH, —O-glycosyl, —O($C_{1-6}$ alkyl) and -halogen. Even more preferably, $R^4$ is selected from —OH and —O-glycosyl. Still more preferably, $R^4$ is selected from —OH and —O-glucosyl. Most preferably, $R^4$ is —OH.

It is to be understood that the one or more optional substituents of alkyl, alkenyl, alkynyl, alkylene, alkenylene and alkynylene (as defined for any such groups in any moieties) are preferably independently selected from -halogen, —OH, —O—$C_{1-6}$ alkyl and —CN. Furthermore, the one or more optional substituents of cycloalkyl and aryl (as defined for any such groups in any moieties) are preferably independently selected from —$C_{1-6}$, -halogen, —OH, —O—$C_{1-6}$ alkyl and —CN. Any otherwise undefined optional substituents are preferably independently selected from -halogen, —OH, —O—$C_{1-6}$ alkyl and —CN.

As used herein the term "glycosyl" preferably refers to a substituent structure obtained by removing the hemiacetal hydroxyl group from the cyclic form of a monosaccharide. More preferably, the term "glycosyl" refers to "glucosyl", i.e. a substituent structure obtained by removing the hemiacetal hydroxyl group from the cyclic form of glucose.

In the compound of formula (I), it is preferred that the following definitions apply, either independently or in any combination thereof: $R^1$ is preferably linear or branched $C_{4-6}$ alkyl, more preferably, $R^1$ is a $C_5$ alkyl, most preferably, $R^1$ is $C_5H_{11}$, $R^2$ is preferably —C(O)OH, $R^3$ is preferably —OH and $R^4$ is preferably —OH.

Examples of compounds with the formula (I) to be produced in the presence of the plant extract having prenyltransferase activity according to the present invention include the following compounds:

cannabigerovarinic acid (CBGVA); cannabigerolic acid (CBGA); 6-butyl-3-[(2E)-3,7-dimethylocta-2,6-dien-1-yl]-2,4-dihydroxybenzoic acid; 3-[(2E)-3,7-dimethylocta-2,6-dien-1-yl]-6-hexyl-2,4-dihydroxybenzoic acid; 3-[(2E)-3,7-dimethylocta-2,6-dien-1-yl]-2,4-dihydroxy-6-(3-methylpentyl)benzoic acid; 3-[(2E)-3,7-dimethylocta-2,6-dien-1-yl]-2,4-dihydroxy-6-(pent-4-en-1-yl)benzoic acid; 3-[(2E)-3,7-dimethylocta-2,6-dien-1-yl]-6-(hex-5-yn-1-yl)-2,4-dihydroxybenzoic acid; 3-[(2E)-3,7-dimethylocta-2,6-dien-1-yl]-2-hydroxy-6-propyl-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-2-hydroxy-6-pentyl-4-{[(3R,4R,5S,6S)-4,5,6-trihydroxy-3-(hydroxymethyl) oxan-2-yl]oxy}benzoic acid; 6-butyl-3-[(2E)-3,7-dimethylocta-2,6-dien-1-yl]-2-hydroxy-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-6-hexyl-2-hydroxy-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-2-hydroxy-6-(3-methylpentyl)-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-2-hydroxy-6-(pent-4-en-1-yl)-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-6-(hex-5-yn-1-yl)-2-hydroxy-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-4-hydroxy-6-propyl-2-{[(3S,4R,5S,6S)-4,5,6-trihydroxyoxan-3-yl]methoxy}benzoic acid; 3-[(2E)-3,7-dimethylocta-2,6-dien-1-yl]-4-hydroxy-6-pentyl-2-{[(3S,4R,5S,6S)-4,5,6-trihydroxyoxan-3-yl] methoxy}benzoic acid; 6-butyl-3-[(2E)-3,7-dimethylocta-2,6-dien-1-yl]-4-hydroxy-2-{[(3S,4R,5S,6S)-4,5,6-trihydroxyoxan-3-yl]methoxy}benzoic acid; 3-[(2E)-3,7-dimethylocta-2,6-dien-1-yl]-6-hexyl-4-hydroxy-2-{[(3S,4R,5S,6S)-4,5,6-trihydroxyoxan-3-yl] methoxy}benzoic acid; 3-[(2E)-3,7-dimethylocta-2,6-dien-1-yl]-4-hydroxy-6-(3-methylpentyl)-2-{[(3S,4R,5S,6S)-4,5,6-trihydroxyoxan-3-yl]methoxy}benzoic acid; 3-[(2E)-3,7-dimethylocta-2,6-dien-1-yl]-4-hydroxy-6-(pent-4-en-1-yl)-2-{[(3S,4R,5S,6S)-4,5,6-trihydroxyoxan-3-yl]methoxy}benzoic acid; 3-[(2E)-3,7-dimethylocta-2,6-dien-1-yl]-6-(hex-5-yn-1-yl)-4-hydroxy-2-{[(3S,4R,5S,6S)-4,5,6-trihydroxyoxan-3-yl]methoxy}benzoic acid; 3-[(2E)-3,7-dimethylocta-2,6-dien-1-yl]-6-propyl-4-{[(3R,4R,5S,6S)-4,5,6-trihydroxy-3-(hydroxymethyl) oxan-2-yl]oxy}-2-{[(3S,4R,5S,6S)-4,5,6-trihydroxyoxan-3-yl] methoxy}benzoic acid; 3-[(2E)-3,7-dimethylocta-2,6-dien-1-yl]-6-pentyl-4-{[(3R,4R,5S,6S)-4,5,6-trihydroxy-3-(hydroxymethyl) oxan-2-yl]oxy}-2- {[(3S,4R,5S,6S)-4,5,6-trihydroxyoxan-3-yl]methoxy}benzoic acid; 6-butyl-3-[(2E)-3,7-dimethylocta-2,6-dien-1-yl]-4-{[(3R,4R,5S,6S)-4,5,6-trihydroxy-3-(hydroxymethyl) oxan-2-yl]oxy}-2- {[(3S,4R,5S,6S)-4,5,6-trihydroxyoxan-3-yl]methoxy}benzoic acid; 3-[(2E)-3,7-dimethylocta-2,6-dien-1-yl]-6-hexyl-4-{[(3R,4R,5S,6S)-4,5,6-trihydroxy-3-(hydroxymethyl) oxan-2-yl] oxy}-2- {[(3S,4R,5S,6S)-4,5,6-trihydroxyoxan-3-yl] methoxy}benzoic acid; 3-[(2E)-3,7-dimethylocta-2,6-dien-1-yl]-6-(3-methylpentyl)-4-{[(3R,4R,5S,6S)-4,5,6-trihydroxy-3-(hydroxymethyl) oxan-2-yl]oxy}-2-{[(3S,4R,5S,6S)-4,5,6-trihydroxyoxan-3-yl] methoxy}benzoic acid; 3-[(2E)-3,7-dimethylocta-2,6-dien-1-yl]-6-(pent-4-en-1-yl)-4-{[(3R,4R,5S,6S)-4,5,6-trihydroxy-3-(hydroxymethyl) oxan-2-yl]oxy}-2-{[(3S,4R,5S,6S)-4,5,6-trihydroxyoxan-3-yl] methoxy}benzoic acid; and 3-[(2E)-3,7-dimethylocta-2,6-dien-1-yl]-6-(hex-5-yn-1-yl)-4-{[(3R,4R,5S,6S)-4,5,6-trihydroxy-3-(hydroxymethyl) oxan-2-yl]oxy}-2-{[(3S,4R,5S,6S)-4,5,6-trihydroxyoxan-3-yl] methoxy}benzoic acid.

Examples of compounds with the formula (I) to be produced in the presence of the plant extract having prenyltransferase activity according to the present invention alternatively include the following compounds:

cannabigerovarine (CBGV), cannabigerol (CBG), 5-butyl-2-[(2E)-3,7-dimethylocta-2,6-dien-1-yl]benzene-1,3-diol, 2-[(2E)-3,7-dimethylocta-2,6-dien-1-yl]-5-hexylbenzene-1,3-diol, 2-[(2E)-3,7-dimethylocta-2,6-dien-1-yl]-5-(3-methylpentyl)benzene-1,3-diol, 2-[(2E)-3,7-dimethylocta-2,6-dien-1-yl]-5-(pent-4-en-1-yl)benzene-1,3-diol, 2-[(2E)-3,7-dimethylocta-2,6-dien-1-yl]-5-(hex-5-yn-1-yl)benzene-1,3-diol, (2S,3S,4R,5R)-6-{2-[(2E)-3,7-dimethylocta-2,6-dien-1-yl]-3-hydroxy-5-propylphenoxy}-5-(hydroxymethyl) oxane-2,3,4-triol, (2S,3S,4R,5R)-6-{2-[(2E)-3,7-dimethylocta-2,6-dien-1-yl]-3-hydroxy-5-pentylphenoxy}-5-(hydroxymethyl) oxane-2,3,4-triol, (2S,3S,4R,5R)-6-{5-butyl-2-[(2E)-3,7-dimethylocta-2,6-dien-1-yl]-3-hydroxyphenoxy}-5-(hydroxymethyl) oxane-2,3,4-triol, (2S,3S,4R,5R)-6-{2-[(2E)-3,7-dimethylocta-2,6-dien-1-yl]-5-hexyl-3-hydroxyphenoxy}-5-(hydroxymethyl) oxane-2,3,4-triol, (2S,3S,4R,5R)-6-{2-[(2E)-3,7-dimethylocta-2,6-dien-1-yl]-3-hydroxy-5-(3-methylpentyl) phenoxy}-5-(hydroxymethyl) oxane-2,3,4-triol, (2S,3S,4R,5R)-6-{2-[(2E)-3,7-dimethylocta-2,6-dien-1-yl]-3-hydroxy-5-(pent-4-en-1-yl) phenoxy}-5-(hydroxymethyl) oxane-2,3,4-triol, (2S,3S,4R,5R)-6-{2-[(2E)-3,7-dimethylocta-2,6-dien-1-yl]-5-(hex-5-yn-1-yl)-3-hydroxyphenoxy}-5-(hydroxymethyl) oxane-2,3,4-triol, (2S,3S,4R,5R)-6-{2-[(2E)-3,7-dimethylocta-2,6-dien-1-yl]-5-propyl-3-{[(3R,4R,5S,6S)-4,5,6-trihydroxy-3-(hydroxymethyl) oxan-2-yl]oxy}phenoxy}-5-(hydroxymethyl) oxane-2, 3,4-triol, (2S,3S,4R,5R)-6-{2-[(2E)-3,7-dimethylocta-2,6-dien-1-yl]-5-pentyl-3-{[(3R,4R,5S,6S)-4,5,6-trihydroxy-3-(hydroxymethyl) oxan-2-yl]oxy}phenoxy}-5-(hydroxymethyl) oxane-2,3,4-triol, (2S,3S,4R,5R)-6-{5-butyl-2-[(2E)-3,7-dimethylocta-2,6-dien-1-yl]-3-{[(3R,4R,5S,6S)-4,5,6-trihydroxy-3-(hydroxymethyl) oxan-2-yl]oxy}phenoxy}-5-(hydroxymethyl) oxane-2,3,4-triol, (2S,3S,4R,5R)-6-{2-[(2E)-3,7-dimethylocta-2,6-dien-1-yl]-5-hexyl-3-{[(3R,4R,5S,6S)-4,5,6-trihydroxy-3-(hydroxymethyl) oxan-2-yl]oxy}phenoxy}-5-(hydroxymethyl) oxane-2,3,4-triol, (2S,3S,4R,5R)-6-{2-[(2E)-3,7-dimethylocta-2,6-dien-1-yl]-5-(3-methylpentyl)-3-{[(3R,4R,5S,6S)-4,5,6-trihydroxy-3-(hydroxymethyl) oxan-2-yl]oxy}phenoxy}-5-(hydroxymethyl) oxane-2,3,4-triol, (2S,3S,4R,5R)-6-{2-[(2E)-3,7-dimethylocta-2,6-dien-1-yl]-5-(pent-4-en-1-yl)-3-{[(3R,4R,5S,6S)-4,5,6-trihydroxy-3-(hydroxymethyl) oxan-2-yl]oxy}phenoxy}-5-(hydroxymethyl) oxane-2,3,4-triol, and (2S,3S,4R,5R)-6-{2-[(2E)-3,7-dimethylocta-2,6-dien-1-yl]-5-(hex-5-yn-1-yl)-3-{[(3R,4R,5S,6S)-4,5,6-trihydroxy-3-(hydroxymethyl) oxan-2-yl]oxy}phenoxy}-5-(hydroxymethyl) oxane-2,3,4-triol.

Examples of compounds with the formula (I) to be produced in the presence of the plant extract having prenyltransferase activity according to the present invention are preferably the following compounds:

3-[(2E)-3,7-dimethylocta-2,6-dien-1-yl]-2,4-dihydroxy-6-pentylbenzoic acid, 6-butyl-3-[(2E)-3,7-dimethylocta-2,6-dien-1-yl]-2,4-dihydroxybenzoic acid, 3-[(2E)-3,7-dimethylocta-2,6-dien-1-yl]-6-hexyl-2,4-dihydroxybenzoic acid, 3-[(2E)-3,7-dimethylocta-2,6-dien-1-yl]-2,4-dihydroxy-6-(3-methylpentyl)benzoic acid, 3-[(2E)-3,7-dimethylocta-2,6-dien-1-yl]-2,4-dihydroxy-6-(pent-4-en-1-yl)benzoic acid, 3-[(2E)-3,7-dimethylocta-2,6-dien-1-yl]-6-(hex-5-yn-1-yl)-2,4-dihydroxybenzoic acid, CBG; 5-butyl-2-[(2E)-3,7-dimethylocta-2,6-dien-1-yl]benzene-1,3-diol; 2-[(2E)-3,7-dimethylocta-2,6-dien-1-yl]-5-hexylbenzene-1,3-diol; 2-[(2E)-3,7-dimethylocta-2,6-dien-1-yl]-5-(3-methylpentyl)benzene-1,3-diol; 2-[(2E)-3,7-dimethylocta-2,6-dien-1-yl]-5-(pent-4-en-1-yl) benzene-1,3-diol; 2-[(2E)-3,7-dimethylocta-2,6-dien-1-yl]-5-(hex-5-yn-1-yl)benzene-1,3-diol.

Even more preferably, examples of compounds with the formula (I) to be produced in the presence of the plant extract having prenyltransferase activity according to the present invention are the following compounds:

3-[(2E)-3,7-dimethylocta-2,6-dien-1-yl]-2,4-dihydroxy-6-pentylbenzoic acid, 6-butyl-3-[(2E)-3,7-dimethylocta-2,6-dien-1-yl]-2,4-dihydroxybenzoic acid, 3-[(2E)-3,7-dimethylocta-2,6-dien-1-yl]-6-hexyl-2,4-dihydroxybenzoic acid, 3-[(2E)-3,7-dimethylocta-2,6-dien-1-yl]-2,4-dihydroxy-6-(3-methylpentyl)benzoic acid, 3-[(2E)-3,7-dimethylocta-2,6-dien-1-yl]-2,4-dihydroxy-6-(pent-4-en-1-yl)benzoic acid, 3-[(2E)-3,7-dimethylocta-2,6-dien-1-yl]-6-(hex-5-yn-1-yl)-2,4-dihydroxybenzoic acid.

Most preferably, compound (I) is cannabigerolic acid (CBGA).

Luo et al. (Nature. (2019), 567:123-126) has proved that CBGA and corresponding cannabinoid analogues can be produced from the fatty acid precursors hexanoic acid, pentanoic acid, heptanoic acid, 4-methylhexanoic acid, 5-hexenoic acid and 6-heptynoic acid by isoenzyme CsPT4 (a prenyltransferase of *Cannabis sativa*). The data of Luo et al. render it plausible that the compounds with the formula (I), wherein $R^1$ is selected from linear or branched $C_{1-10}$ alkyl, linear $C_{2-10}$ alkenyl and linear $C_{2-10}$ alkynyl, and the preferred examples of compounds with the formula (I), can be produced in the presence of a plant extract having prenyltransferase activity as disclosed herein.

In the present invention, as shown in the appended Examples, a compound of Formula (I) is produced when a plant extract having prenyltransferase activity is reacted with a compound of Formula (II) and geranyl pyrophosphate (GPP).

A compound of Formula (II) is considered to have the following structure:

Formula (II)

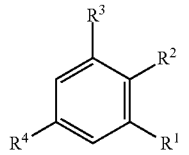

wherein $R^1$, $R^2$, $R^3$ and $R^4$ are as defined for Formula (I).

In the compound of formula (II), it is preferred that the following definitions apply, either independently or in any combination thereof: $R^1$ is preferably linear or branched $C_{4-6}$ alkyl, more preferably, $R^1$ is a $C_5$ alkyl, most preferably, $R^1$ is $C_5H_{11}$, $R^2$ is preferably —C(O)OH, $R^3$ is preferably-OH and $R^4$ is preferably-OH.

Examples of compounds with the formula (II) to be converted in the presence of the plant extract having prenyltransferase activity and GPP according to the present invention include the following compounds:

2,4-dihydroxy-6-propylbenzoic acid; olivetolic acid (OA); 2-butyl-4-hydroxy-6-methylbenzoic acid; 2-hexyl-4-hydroxy-6-methylbenzoic acid; 4-hydroxy-2-methyl-6-(3-methylpentyl)benzoic acid; 4-hydroxy-2-methyl-6-(pent-4-en-1-yl)benzoic acid; 2-(hex-5-yn-1-yl)-4-hydroxy-6-methylbenzoic acid; 2-hydroxy-6-propyl-4-{[(3R,4R,5S,6S)-4,5,6-trihydroxy-3-(hydroxymethyl) oxan-2-yl]oxy}benzoic acid; 2-hydroxy-6-pentyl-4-{[(3R,4R,5S,6S)-4,5,6-trihydroxy-3-(hydroxymethyl) oxan-2-yl]oxy}benzoic acid; 2-butyl-6-hydroxy-4-{[(3R,4R,5S,6S)-4,5,6-trihydroxy-3-(hydroxymethyl) oxan-2-yl]oxy}benzoic acid; 2-hexyl-6-hydroxy-4-{[(3R,4R,5S,6S)-4,5,6-trihydroxy-3-(hydroxymethyl) oxan-2-yl]oxy}benzoic acid; 2-hydroxy-6-(3-methylpentyl)-4-{[(3R,4R,5S,6S)-4,5,6-trihydroxy-3-(hydroxymethyl) oxan-2-yl]oxy}benzoic acid; 2-hydroxy-6-(pent-4-en-1-yl)-4-{[(3R,4R,5S,6S)-4,5,6-trihydroxy-3-(hydroxymethyl) oxan-2-yl]oxy}benzoic acid; 2-(hex-5-yn-1-yl)-6-hydroxy-4-{[(3R,4R,5S,6S)-4,5,6-trihydroxy-3-(hydroxymethyl) oxan-2-yl]oxy}benzoic acid; 4-hydroxy-2-propyl-6-{[(3R,4R,5S,6S)-4,5,6-trihydroxy-3-(hydroxymethyl) oxan-2-yl]oxy}benzoic acid; 4-hydroxy-2-pentyl-6-{[(3R,4R,5S,6S)-4,5,6-trihydroxy-3-(hydroxymethyl) oxan-2-yl]oxy}benzoic acid; 2-butyl-4-hydroxy-6-{[(3R,4R,5S,6S)-4,5,6-trihydroxy-3-(hydroxymethyl) oxan-2-yl]oxy}benzoic acid; 2-hexyl-4-hydroxy-6-{[(3R,4R,5S,6S)-4,5,6-trihydroxy-3-(hydroxymethyl) oxan-2-yl]oxy}benzoic acid; 4-hydroxy-2-(3-methylpentyl)-6-{[(3R,4R,5S,6S)-4,5,6-trihydroxy-3-(hydroxymethyl) oxan-2-yl]oxy}benzoic acid; 4-hydroxy-2-(pent-4-en-1-yl)-6-{[(3R,4R,5S,6S)-4,5,6-trihydroxy-3-(hydroxymethyl) oxan-2-yl]oxy}benzoic acid; 2-(hex-5-yn-1-yl)-4-hydroxy-6-{[(3R,4R,5S,6S)-4,5,6-trihydroxy-3-(hydroxymethyl) oxan-2-yl]oxy}benzoic acid; 2-propyl-4,6-bis({[(3R,4R,5S,6S)-4,5,6-trihydroxy-3-(hydroxymethyl) oxan-2-yl]oxy})benzoic acid; 2-pentyl-4,6-bis({[(3R,4R,5S,6S)-4,5,6-trihydroxy-3-(hydroxymethyl) oxan-2-yl]oxy})benzoic acid; 2-butyl-4,6-bis({[(3R,4R,5S,6S)-4,5,6-trihydroxy-3-(hydroxymethyl) oxan-2-yl]oxy})benzoic acid; 2-hexyl-4,6-bis({[(3R,4R,5S,6S)-4,5,6-trihydroxy-3-(hydroxymethyl) oxan-2-yl]oxy})benzoic acid; 2-(3-methylpentyl)-4,6-bis({[(3R,4R,5S,6S)-4,5,6-trihydroxy-3-(hydroxymethyl) oxan-2-yl]oxy})benzoic acid; 2-(pent-4-en-1-yl)-4,6-bis({[(3R,4R,5S,6S)-4,5,6-trihydroxy-3-(hydroxymethyl) oxan-2-yl]oxy})benzoic acid; and 2-(hex-5-yn-1-yl)-4,6-bis({[(3R,4R,5S,6S)-4,5,6-trihydroxy-3-(hydroxymethyl) oxan-2-yl]oxy})benzoic acid.

Examples of compounds with the formula (II) to be converted in the presence of the plant extract having prenyltransferase activity and GPP according to the present invention are preferably the following compounds:

2,4-dihydroxy-6-pentylbenzoic acid, 2-butyl-4,6-dihydroxybenzoic acid, 2-hexyl-4,6-dihydroxybenzoic acid, 2,4-dihydroxy-6-(3-methylpentyl)benzoic acid, 2,4-dihydroxy-6-(pent-4-en-1-yl)benzoic acid, 2-(hex-5-yn-1-yl)-4,6-dihydroxybenzoic acid.

Most preferably, compound (II) is olivetolic acid (OA).

In the context of the present invention, geranyl pyrophosphat (GPP) relates to a compound with the following structure (III):

Formula (III)

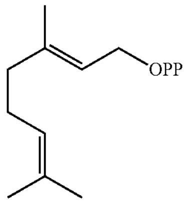

wherein PP represents pyrophosphate.

In the context of the present invention, the term "alkyl" refers to a monovalent saturated acyclic (i.e., non-cyclic) hydrocarbon group which may be linear or branched.

Accordingly, an "alkyl" group does not comprise any carbon-to-carbon double bond or any carbon-to-carbon triple bond. A "$C_{1-10}$ alkyl" denotes an alkyl group having 1 to 10 carbon atoms. A preferred "$C_{1-10}$ alkyl" group is a "$C_{4-6}$ alkyl" group. Exemplary alkyl groups are methyl, ethyl, propyl (e.g., n-propyl or isopropyl), or butyl (e.g., n-butyl, isobutyl, sec-butyl, or tert-butyl). Particularly preferred examples of "alkyl" in the present invention include n-propyl, n-butyl, n-pentyl, 3-methylpentyl and n-hexyl. Unless defined otherwise, the term "alkyl" preferably refers to $C_{1-10}$ alkyl, more preferably to pentyl. In the context of the present invention, the term "alkylene" refers to a divalent saturated acyclic (i.e., non-cyclic) hydrocarbon group which may be linear or branched, which preferably corresponds to an "alkyl" from which a hydrogen radical has been removed.

In the context of the present invention, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-10}$ alkenyl" denotes an alkenyl group having 2 to 10 carbon atoms. A preferred "$C_{2-10}$ alkenyl" group is a "$C_4$-6 alkenyl" group. Exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). A particularly preferred example of "alkenyl" in the present invention is pent-4-enyl. Unless defined otherwise, the term "alkenyl" preferably refers to $C_{2-10}$ alkenyl. In the context of the present invention, the term "alkenylene" refers to a monovalent unsaturated acyclic hydrocarbon group which may be linear or branched and comprises one or more (e.g., one or two) carbon-to-carbon double bonds while it does not comprise any carbon-to-carbon triple bond. The term "alkenylene" preferably corresponds to an "alkenyl" from which a hydrogen radical has been removed.

As used herein, the term "alkynyl" refers to a monovalent unsaturated acyclic hydrocarbon group which may be linear or branched and comprises one or more (e.g., one or two) carbon-to-carbon triple bonds and optionally one or more carbon-to-carbon double bonds. The term "$C_{2-10}$ alkynyl" denotes an alkynyl group having 2 to 10 carbon atoms. A preferred "$C_{2-10}$ alkynyl" group is a "$C_{4-6}$ alkynyl" group. Exemplary alkynyl groups are ethynyl, propynyl, or butynyl. A particularly preferred example of "alkynyl" in the present invention is hex-5-ynyl. As used herein, the term "alkynylene" refers to a monovalent unsaturated acyclic hydrocarbon group which may be linear or branched and comprises one or more (e.g., one or two) carbon-to-carbon triple bonds and optionally one or more carbon-to-carbon double bonds. The term "alkynylene" preferably corresponds to an "alkynyl" from which a hydrogen radical has been removed.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydronaphthyl), tetralinyl (i.e., 1,2,3,4-tetrahydronaphthyl), indanyl, or indenyl (e.g., 1H-indenyl). Unless defined otherwise, an "aryl" preferably has 6 to 10 ring atoms, more preferably refers to phenyl or naphthyl, and even more preferably refers to phenyl.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a $C_{3-10}$ cycloalkyl, and more preferably refers to a $C_{3-7}$ cycloalkyl. A particularly preferred "cycloalkyl" is a monocyclic saturated hydrocarbon ring having 3 to 7 ring members. Moreover, unless defined otherwise, the term "cycloalkyl" even more preferably refers to cyclohexyl or cyclopropyl, and yet even more preferably refers to cyclohexyl.

As used herein, the term "halogen" preferably refers to F, $C_1$, Br or I, more preferably to F, Cl or Br, even more preferably to F or Cl, still more preferably to F.

In the context of the present invention the term "plant" refers to any various photosynthetic, eukaryotic multicellular organisms of the kingdom Plantae, characteristically producing embryos, containing chloroplasts, having cellulose cell walls and lacking locomotion. As used herein, a "plant" includes any plant or part of a plant at any stage of development, including seeds, suspension cultures, plant cells, embryos, meristematic regions, callus tissue, leaves, roots, shoots, gametophytes, sporophytes, pollen, microspores, and progeny thereof. Also included are cuttings, and cell or tissue cultures. As used in conjunction with the present disclosure, plant tissue includes, without limitation, whole plants, plant cells, plant organs, e.g., leaves, stems, roots, meristems, plant seeds, protoplasts, callus, cell cultures, and any groups of plant cells organized into structural and/or functional units.

In the context of the present invention, the term "plant extract" refers to an extract of plant material in a solvent, or to a liquid plant cell culture. The plant material may be obtained from solid plant material or a plant cell culture. In the context of the present invention, the plant material or liquid cell culture used to provide the plant extract may be obtainable from a native or a transgenic plant. Transgenic plants or plant cells differ from naturally occurring ones due to genetic modification. Genetically modified plants or plant cells do not naturally occur, i.e., cannot be found in nature, and differ substantially from naturally occurring plants or plant cells due to the introduction of foreign genetic material, for example a foreign nucleic acid molecule. The nucleic acid molecule can be stably integrated into the genome or may be present in an extrachromosomal manner, e.g., on a plasmid if a microorganism is used. Plant transformation protocols as well as protocols for introducing recombinant nucleic acids into plants or plant cells may vary depending on the type of plant or plant cell, e.g., monocot or dicot, targeted for transformation. Suitable methods of introducing recombinant nucleic acids into plant cells and subsequent insertion into the plant genome include, without limitation, microinjection (Crossway et al., Biotechniques 4 (1986), 320-334), electroporation (Riggs et al., Proc. Natl. Acad Sci. USA 83 (1986), 5602-5606), *Agrobacterium*-mediated transformation (U.S. Pat. No. 5,563,055), direct gene transfer (Paszkowski et al., EMBO J. 3 (1984), 2717-2722), and ballistic particle acceleration (U.S. Pat. No. 4,945,050 and McCabe et al., Biotechnology 6 (1988) 6, 923-926). The liquid cell culture may be obtained from a native plant and may be subsequently genetically modified in vitro. Suitable techniques are known to those skilled in the art and include electroporation (Joersbo and Brunstedt, Electrical manipulation of cells (1996), 201-222), liposome-mediated transfection (Straubinger and Papahadjopoulos, Techniques in Somatic Cell Genetics (1982), 399-413), and polyethylene glycol-mediated transfection (Kofer et al., In Vitro Cell Dev Biol-Plant. (1998), 34:303-309).

The plant material or the liquid cell culture may be obtained from the whole plant or parts thereof as described herein. Specifically, it may be obtained from stems, flowers or fruits, but is preferably obtained from the leaves of the plant. In the present invention, a liquid cell culture is considered to be a plant cell culture, preferably a suspension culture, in a liquid medium. Methods to establish an in vitro plant cell culture from solid plant material are known to those skilled in the art and include callogenesis (Espinosa-Leal et al., Planta (2018), 248:1-18). The plant material or the liquid cell culture may also originate from established plant cell culture lines that endogenously express a prenyltransferase. Suitable in vitro conditions conducive for growth of the plant cell culture are known to the skilled artisan and are dependent on the plant cell to be cultured and its individual culture needs. Conditions to be adjusted include the type of culture media, pH and supply of nutrients, adequate temperature and proper gaseous and liquid environment (Leal et al., Planta (2018), 248:1-18). The plant cell culture can be further genetically modified in vitro as described herein.

In the context of the present invention, the plant material, and/or the plant cells obtained from the plant cell culture, as discussed herein, is/are mixed with an extraction reagent equal to the solvent to provide the plant extract of the present invention. The solvent can be any suitable solvent including organic solvents like methanol, ethanol, propanol, isopropanol, acetone, acetonitrile, ethyl acetate, dichlormethane or dimethylsulfoxide. Preferably, the organic solvent is used in a volume/volume (v/v) ratio of up to 14%. The solvent may also be an aqueous solution like a buffer such as TAPS, Bicine, Tricine, TAPSO, HEPES, TES, MOPS, PIPES, Cacodylate, MES, $Na_2HPO_4$, $NaH_2PO_4$, CHES, Acetic acid, Citric acid, Borate, $KH_2PO_4$ and mixtures thereof. Preferably, the solvent is an aqueous buffer. Most preferably, the solvent is a trisodium citrate or a Tris-HCl/NaCl buffer. The extraction process can be carried out at a temperature in the range of 4° C. to 40° C. but is preferably carried out at room temperature (RT). The solvent may have any pH between 3.5 and 8.5, preferably between 4.0 to 8.0 and most preferably between 5.5 and 7.5.

In the context of the present invention, the solid plant material may be fresh, freeze dried or frozen. Preferably, the solid plant material is mechanically comminuted prior or during mixing with the solvent. All comminution methods known to the person skilled in the art are suitable including milling, grinding, and chipping. Grinding in liquid nitrogen is being mentioned as a preferred example. The plant extracts according to the present invention can be crude extracts or can optionally be subjected to further customary steps, such as centrifugation, purification, and/or concentration prior to reacting it with a compound of Formula (II) and geranyl pyrophosphate (GPP) to produce the compound of Formula (I). The term "reacting" is considered as contacting the plant extract of the present invention with a compound of Formula (II) and GPP, for instance by addition of these compounds to the plant extract.

In the present invention, the term "prenyltransferase activity" refers to the activity of an enzyme which can catalyze the prenylation of a compound by transfer of a prenyl residue from a prenyl group donor molecule to a carbon, nitrogen or an oxygen atom of a prenyl group acceptor compound. The acceptor compound refers to the compound of the above defined formula (II) or any preferred embodiments thereof. The donor compound refers to the compound of the above defined formula (III).

The plant extract having prenyltransferase activity according to the present invention refers to a plant extract which endogenously exhibits the activity of an enzyme i.e. a prenyltransferase, to convert a compound of the formula (II) and geranyl pyrophosphate (GPP) having Formula (III) to a compound of Formula (I) as described herein. Even more preferably and as shown in the appended Examples, the term "prenyltransferase activity" refers in the context of the present invention to the activity of an enzyme to convert OA and GPP into CBGA. In the context of the present invention, the acceptor compound as described herein may be prenylated at any position of the carbon backbone. In case the acceptor compound as described herein is OA, prenylation by the prenyltransferase activity according to the present invention is preferably carried out in the 3-position of the aromatic ring structure.

The plant extract having prenyltransferase activity of the present invention may be obtained from any plant type which endogenously exhibits prenyltransferase activity but does not naturally produce cannabinoids. In the context of the present invention, naturally means that the plant or plant cell in its native state, as found in nature, does not build or produce cannabinoid, cannabinoid-like or cannabimimetic substances. Accordingly, in the context of the present invention, the plant extract as used in the process disclosed herein is not a plant extract obtained from a plant that naturally produces phytocannabinoids, phytocannabinoid-like substances or cannabimimetic compounds like *Acmella oleracea, Cannabis sativa, Echinaceae angustifolia, Echinaceae purpurea, Helichrysum umbraculigerum, Heliopsis helianthoides, Lepidium meyenii, Piper methysticum, Piper nigrum, Radula marginata, Radula perrottetii, Rhododendron anthopogonoides* and *Tuber melanosporum*. Specifically, in the context of the present invention, a plant that does not naturally produce cannabinoids is considered to be a native plant that does not show cannabinoid production, particularly CBGA, THCA, CBCA and CBDA production, when compared to *Cannabis sativa* by using standard methods to detect such products including HPLC-MS measurement as described in the appended Examples. Consequently, the plant extract having prenyltransferase activity of the present invention may be obtained from any plant type which endogenously exhibits prenyltransferase activity but does not build or produce cannabinoid, cannabinoid-like or cannabimimetic substances. Preferably, the plant extract is a not a *Cannabis sativa* plant extract. Preferably, the plant used to provide the plant extract according to the present invention is obtained from a plant selected from the group of *Lactuca sativa, Nepeta cataria, Nicotiana benthamiana, Nicotiana tabacum* and *Ocimum basilicum*. However, the teaching of the present invention is not restricted to the plant species which had been used in the appended Examples as model plants. The plants may be grown under suitable conditions allowing growth and biomass expansion. Suitable growth conditions are known to the person skilled in the art. Growth time period, temperature, humidity, irrigation and illumination settings as well as ventilation and fertilization may pe optimized dependent on the cultured plant species.

The prenyltransferase activity in the context of the present invention includes aromatic prenyltransferase activity. Enzymes exhibiting prenyltransferase activity in the context of the present invention may be present in membrane-bound or soluble form but are preferably soluble. Prenyltransferase activity as disclosed herein can be determined by the skilled person by using methods well established in the art. In the context of the present invention, the measurement of the level of the prenyltransferase activity may be done by measuring the decrease of the enzyme substrate but may be preferably done by measuring the amount of the corresponding reaction product. Corresponding methods are well known to the person skilled in the art and include analytical methods such as HPLC or HPLC-MS; see also Fellermeier and Zenk., FEBS Lett. (1998), 8; 427 (2): 283-5 and Gülck et al., J. Nat. Prod. (2020). As described in the appended Examples prenyltransferase activity of a plant extract may be measured by reacting the plant extract with OA and GPP and analyzing the reaction products via HPLC-MS. Detected metabolites then can be compared to a CBGA reference standard.

In case the plant extract is a liquid cell culture, without binding to any theory, it is considered that the herein defined substrates are taken up by the plant cells having prenyltransferase activity and converted intracellularly into the herein described products. As the enzymes having prenyltransferase activity remain intracellular, cell purification and cell lysis of the liquid cell culture might be performed prior to determining the enzyme activity. The person skilled in the art is familiar with suitable purification and cell lysis methods. Exemplarily, the cell lysis methods as described herein in the Examples could be used.

The present invention further relates to a process for the production of a compound of Formula (IV), wherein the process comprises producing a compound of Formula (I) as described herein and converting the compound of Formula (I) to the compound of Formula (IV), in the presence of any enzyme capable of mediating the conversion. Conversion of the compound of Formula (I) to the compound of Formula (IV) can be mediated by tetrahydrocannabinolic acid synthase (THCAS; EC 1.21.3.7, GenBank accession AB057805, GenBank version AB057805.1, SEQ ID NO: 1). In the context of the present invention, conversion of the compound of Formula (I) to the compound of Formula (IV) can also be mediated by an enzyme with an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of THCAS (EC 1.21.3.7, GenBank accession AB057805, GenBank version AB057805.1, SEQ ID NO: 1) and which is characterized by having the activity to convert the compound of Formula (I) to the compound of Formula (IV). In the context of the present invention, conversion of the compound of Formula (I) to the compound of Formula (IV) can also be mediated by (an) enzyme(s) which is/are obtained from (a) naturally occurring enzyme(s), e.g., by the introduction of mutations or other alterations which, e.g., alter or improve the enzymatic activity, the stability and which is characterized by having the activity to convert the compound of Formula (I) to the compound of Formula (IV).

In the present invention, a compound of Formula (IV) is considered to have the following structure:

Formula (IV)

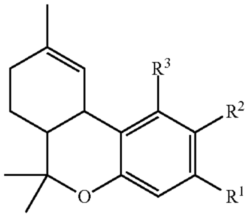

wherein $R^1$, $R^2$ and $R^3$ are as defined for Formula (I).

In the compound of formula (IV), it is preferred that the following definitions apply, either independently or in any combination thereof: $R^1$ is preferably linear or branched $C_{4-6}$ alkyl, more preferably, $R^1$ is a $C_5$ alkyl, most preferably, $R^1$ is $C_5H_{11}$, $R^2$ is preferably —C(O)OH and $R^3$ is preferably-OH.

Examples of compounds with the formula (IV) to be produced according to the process as described herein include the following compounds:

tetrahydrocannabivarinic acid (THCVA); delta-9-tetrahydrocannabinolic acid (THCA); (6aR,10aR)-3-butyl-1-hydroxy-6,6,9-trimethyl-6H,6aH,7H,8H,10aH-benzo[c]isochromene-2-carboxylic acid; (6aR,10aR)-3-hexyl-1-hydroxy-6,6,9-trimethyl-6H,6aH, 7H,8H, 10aH-benzo[c]isochromene-2-carboxylic acid; (6aR, 10aR)-1-hydroxy-6,6,9-trimethyl-3-(3-methylpentyl)-6H,6aH, 7H,8H, 10aH-benzo[c]isochromene-2-carboxylic acid; (6aR,10aR)-1-hydroxy-6,6,9-trimethyl-3-(pent-4-en-1-yl)-6H,6aH,7H,8H, 10aH-benzo[c]

isochromene-2-carboxylic acid; (6aR,10aR)-6,6,9-trimethyl-3-propyl-1-{[(3R,4R,5S,6S)-4,5,6-trihydroxy-3-(hydroxymethyl) oxan-2-yl]oxy}-6H, 6aH,7H,8H, 10aH-benzo[c]isochromene-2-carboxylic acid; (6aR,10aR)-6,6,9-trimethyl-3-pentyl-1-{[(3R,4R, 5S,6S)-4,5,6-trihydroxy-3-(hydroxymethyl) oxan-2-yl] oxy}-6H,6aH, 7H, 8H, 10aH-benzo[c]isochromene-2-carboxylic acid; (6aR,10aR)-3-butyl-6,6,9-trimethyl-1-{[(3R,4R,5S,6S)-4,5,6-trihydroxy-3-(hydroxymethyl) oxan-2-yl]oxy}-6H,6aH,7H, 8H, 10aH-benzo[c]isochromene-2-carboxylic acid; 3-hexyl-6,6,9-trimethyl-1-{[(2S,3R,4R,5S,6S)-4,5,6-trihydroxy-3-(hydroxymethyl) oxan-2-yl]oxy}-6H,6aH,7H,8H, 10aH-benzo[c] isochromene-2-carboxylic Acid; (6aR,10aR)-6,6,9-trimethyl-3-(3-methylpentyl)-1-{[(3R,4R,5S,6S)-4,5, 6-trihydroxy-3-(hydroxymethyl) oxan-2-yl]oxy}-6H, 6aH,7H,8H, 10aH-benzo[c]isochromene-2-carboxylic acid; (6aR,10aR)-6,6,9-trimethyl-3-(pent-4-en-1-yl)-1-{[(3R,4R,5S,6S)-4,5,6-trihydroxy-3-(hydroxymethyl) oxan-2-yl]oxy}-6H,6aH,7H,8H, 10aH-benzo[c]isochromene-2-carboxylic acid and (6aR,10aR)-3-(hex-5-yn-1-yl)-6,6,9-trimethyl-1-{[(3R,4R,5S,6S)-4,5,6-trihydroxy-3-(hydroxymethyl) oxan-2-yl]oxy}-6H,6aH, 7H,8H, 10aH-benzo[c]isochromene-2-carboxylic acid;

Examples of compounds with the formula (IV) to be produced according to the process as described herein alternatively include the following compounds:

tetrahydrocannabivarinic acid (THCVA); delta-9-tetrahydrocannabinolic acid (THCA); 6-butyl-2,4-dihydroxy-3-[(1R,6R)-3-methyl-6-(prop-1-en-2-yl)cyclohex-2-en-1-yl]benzoic acid; 6-hexyl-2,4-dihydroxy-3-[(1R, 6R)-3-methyl-6-(prop-1-en-2-yl)cyclohex-2-en-1-yl] benzoic acid; 2,4-dihydroxy-3-[(1R,6R)-3-methyl-6-(prop-1-en-2-yl)cyclohex-2-en-1-yl]-6-(3-methylpentyl)benzoic acid; 2,4-dihydroxy-3-[(1R,6R)-3-methyl-6-(prop-1-en-2-yl)cyclohex-2-en-1-yl]-6-(pent-4-en-1-yl)benzoic acid; 6-(hex-5-yn-1-yl)-2,4-dihydroxy-3-[(1R,6R)-3-methyl-6-(prop-1-en-2-yl) cyclohex-2-en-1-yl]benzoic acid; 6,6,9-trimethyl-3-propyl-1-{[(2S,3R,4R,5S,6S)-4,5,6-trihydroxy-3-(hydroxymethyl) oxan-2-yl]oxy}-6H,6aH, 7H,8H, 10aH-benzo[c]isochromene-2-carboxylic acid; 6,6,9-trimethyl-3-pentyl-1-{[(2S,3R,4R,5S,6S)-4,5,6-trihydroxy-3-(hydroxymethyl) oxan-2-yl]oxy}-6H,6aH, 7H,8H, 10aH-benzo[c]isochromene-2-carboxylic acid; 3-butyl-6,6,9-trimethyl-1-{[(2S,3R,4R,5S,6S)-4,5,6-trihydroxy-3-(hydroxymethyl) oxan-2-yl]oxy}-6H, 6aH,7H,8H, 10aH-benzo[c]isochromene-2-carboxylic acid; 3-hexyl-6,6,9-trimethyl-1-{[(2S,3R,4R,5S,6S)-4, 5,6-trihydroxy-3-(hydroxymethyl) oxan-2-yl]oxy}-6H, 6aH,7H,8H, 10aH-benzo[c]isochromene-2-carboxylic acid; 6,6,9-trimethyl-3-(3-methylpentyl)-1-{[(2S,3R, 4R,5S,6S)-4,5,6-trihydroxy-3-(hydroxymethyl) oxan-2-yl]oxy}-6H,6aH, 7H, 8H, 10aH-benzo[c]isochromene-2-carboxylic acid; 6,6,9-trimethyl-3-(pent-4-en-1-yl)-1-{[(2S,3R,4R,5S,6S)-4,5,6-trihydroxy-3-(hydroxymethyl) oxan-2-yl]oxy}-6H,6aH,7H, 8H, 10aH-benzo[c]isochromene-2-carboxylic acid; and 3-(hex-5-yn-1-yl)-6,6,9-trimethyl-1-{[(2S,3R,4R,5S, 6S)-4,5,6-trihydroxy-3-(hydroxymethyl) oxan-2-yl] oxy}-6H,6aH,7H,8H, 10aH-benzo[c]isochromene-2-carboxylic acid.

Examples of compounds with the formula (IV) to be produced according to the process as described herein are preferably the following compounds:

(6aR,10aR)-1-hydroxy-6,6,9-trimethyl-3-pentyl-6H,6aH, 7H,8H, 10aH-benzo[c]isochromene-2-carboxylic acid, (6aR,10aR)-3-butyl-1-hydroxy-6,6,9-trimethyl-6H, 6aH,7H,8H, 10aH-benzo[c]isochromene-2-carboxylic acid, (6aR,10aR)-3-hexyl-1-hydroxy-6,6,9-trimethyl-6H,6aH,7H, 8H, 10aH-benzo[c]isochromene-2-carboxylic acid, (6aR,10aR)-1-hydroxy-6,6,9-trimethyl-3-(3-methylpentyl)-6H,6aH,7H,8H, 10aH-benzo[c] isochromene-2-carboxylic acid, (6aR,10aR)-1-hydroxy-6,6,9-trimethyl-3-(pent-4-en-1-yl)-6H,6aH, 7H,8H, 10aH-benzo[c]isochromene-2-carboxylic acid, (6aR,10aR)-3-(hex-5-yn-1-yl)-1-hydroxy-6,6,9-trimethyl-6H,6aH,7H, 8H, 10aH-benzo[c]isochromene-2-carboxylic acid.

Most preferably, compound (IV) is delta-9-tetrahydrocannabinolic acid (THCA).

In the present invention, a compound of Formula (IV) produced as described herein, is further decarboxylated to a compound of Formula (VII). As will be understood, the compound to be decarboxylated preferably has a —C(O)OH group as $R^2$. A compound of Formula (VII) is considered to have the following structure:

Formula (VII)

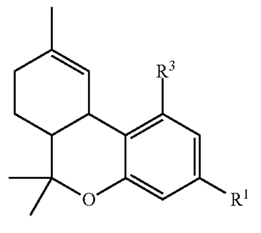

wherein $R^1$ and $R^3$ are as defined for Formula (I).

In the compound of formula (VII), it is preferred that the following definitions apply, either independently or in any combination thereof: $R^1$ is preferably linear or branched $C_{4-6}$ alkyl, more preferably, $R^1$ is a $C_5$ alkyl, most preferably, $R^1$ is $C_5H_{11}$, and $R^3$ is preferably-OH.

Examples of compounds with the formula (VII) according to the present invention include the following compounds:

tetrahydrocannabivarine (THCV); delta-9-tetrahydrocannabinol (THC); (6aR,10aR)-3-butyl-6,6,9-trimethyl-6H,6aH,7H,8H, 10aH-benzo[c]isochromen-1-ol; (6aR, 10aR)-3-hexyl-6,6,9-trimethyl-6H,6aH,7H, 8H, 10aH-benzo[c]isochromen-1-ol; (6aR,10aR)-6,6,9-trimethyl-3-(3-methylpentyl)-6H,6aH,7H,8H, 10aH-benzo[c] isochromen-1-ol; (6aR,10aR)-6,6,9-trimethyl-3-(pent-4-en-1-yl)-6H,6aH, 7H, 8H, 10aH-benzo[c] isochromen-1-ol; (6aR,10aR)-3-(hex-5-yn-1-yl)-6,6,9-trimethyl-6H,6aH,7H,8H, 10aH-benzo[c]isochromen-1-ol; (2S,3S,4R,5R)-6-{[(6aR,10aR)-6,6,9-trimethyl-3-propyl-6H,6aH, 7H, 8H, 10aH-benzo[c]isochromen-1-yl]oxy}-5-(hydroxymethyl) oxane-2,3,4-triol; (2S, 3S,4R,5R)-6-{[(6aR,10aR)-6,6,9-trimethyl-3-pentyl-6H,6aH, 7H,8H, 10aH-benzo[c]isochromen-1-yl]oxy}-5-(hydroxymethyl) oxane-2,3,4-triol; (2S,3S,4R,5R)-6-{[(6aR,10aR)-3-butyl-6,6,9-trimethyl-6H,6aH, 7H, 8H, 10aH-benzo[c]isochromen-1-yl]oxy}-5-(hydroxymethyl) oxane-2,3,4-triol; (2S,3S,4R,5R)-6-{[(6aR,10aR)-3-hexyl-6,6,9-trimethyl-6H,6aH,7H,8H, 10aH-benzo[c]isochromen-1-yl]oxy}-5-(hydroxymethyl) oxane-2,3,4-triol; (2S,3S,4R,5R)-6-{[(6aR, 10aR)-6,6,9-trimethyl-3-(3-methylpentyl)-6H,6aH, 7H,8H, 10aH-benzo[c]isochromen-1-yl]oxy}-5-(hydroxymethyl) oxane-2,3,4-triol; (2S,3S,4R,5R)-6-{[(6aR,10aR)-6,6,9-trimethyl-3-(pent-4-en-1-yl)-6H, 6aH, 7H, 8H, 10aH-benzo[c]isochromen-1-yl]oxy}-5-(hydroxymethyl) oxane-2,3,4-triol; and (2S,3S,4R,5R)-6-{[(6aR,10aR)-3-(hex-5-yn-1-yl)-6,6,9-trimethyl-6H,6aH,7H,8H, 10aH-benzo[c]isochromen-1-yl]oxy}-5-(hydroxymethyl) oxane-2,3,4-triol.

Examples of compounds with the formula (VII) according to the present invention alternatively include the following compounds:

tetrahydrocannabivarine (THCV); delta-9-tetrahydrocannabinol (THC); 5-butyl-2-[(1R,6R)-3-methyl-6-(prop-1-en-2-yl)cyclohex-2-en-1-yl]benzene-1,3-diol; 5-hexyl-2-[(1R,6R)-3-methyl-6-(prop-1-en-2-yl)cyclohex-2-en-1-yl]benzene-1,3-diol; 2-[(1R,6R)-3-methyl-6-(prop-1-en-2-yl)cyclohex-2-en-1-yl]-5-(3-methylpentyl)benzene-1,3-diol; 2-[(1R,6R)-3-methyl-6-(prop-1-en-2-yl)cyclohex-2-en-1-yl]-5-(pent-4-en-1-yl)benzene-1,3-diol; 5-(hex-5-yn-1-yl)-2-[(1R,6R)-3-methyl-6-(prop-1-en-2-yl)cyclohex-2-en-1yl]benzene-1,3-diol; (2S,3S,4R,5R,6S)-5-(hydroxymethyl)-6-({6,6,9-trimethyl-3-propyl-6H,6aH,7H,8H, 10aH-benzo[c]isochromen-1-yl}oxy) oxane-2,3,4-triol; (2S,3S,4R,5R,6S)-5-(hydroxymethyl)-6-({6,6,9-trimethyl-3-pentyl-6H,6aH,7H, 8H, 10aH-benzo[c]isochromen-1-yl}oxy) oxane-2,3,4-triol; (2S,3S,4R,5R,6S)-6-({3-butyl-6,6,9-trimethyl-6H,6aH,7H,8H, 10aH-benzo[c]isochromen-1-yl}oxy)-5-(hydroxymethyl) oxane-2,3,4-triol; (2S,3S,4R,5R,6S)-6-({3-hexyl-6,6,9-trimethyl-6H,6aH,7H,8H, 10aH-benzo[c]isochromen-1-yl}oxy)-5-(hydroxymethyl) oxane-2,3,4-triol; (2S,3S,4R,5R,6S)-5-(hydroxymethyl)-6-{[6,6,9-trimethyl-3-(3-methylpentyl)-6H,6aH,7H, 8H, 10aH-benzo[c]isochromen-1-yl]oxy}oxane-2,3,4-triol; (2S,3S,4R,5R,6S)-5-(hydroxymethyl)-6-{[6,6,9-trimethyl-3-(pent-4-en-1-yl)-6H,6aH,7H,8H, 10aH-benzo[c]isochromen-1-yl]oxy}oxane-2,3,4-triol; and (2S,3S,4R,5R,6S)-6-{[3-(hex-5-yn-1-yl)-6,6,9-trimethyl-6H,6aH, 7H, 8H, 10aH-benzo[c]isochromen-1-yl]oxy}-5-(hydroxymethyl) oxane-2,3,4-triol.

Examples of compounds with the formula (VII) according to the present invention are preferably the following compounds:

(6aR,10aR)-6,6,9-trimethyl-3-pentyl-6a,7,8,10a-tetrahydro-6H-benzo[c]chromen-1-ol, (6aR,10aR)-3-butyl-6,6,9-trimethyl-6H,6aH,7H, 8H, 10aH-benzo[c]isochromen-1-ol, (6aR,10aR)-3-hexyl-6,6,9-trimethyl-6H,6aH,7H,8H, 10aH-benzo[c]isochromen-1-ol, (6aR, 10aR)-6,6,9-trimethyl-3-(3-methylpentyl)-6H,6aH,7H, 8H, 10aH-benzo[c]isochromen-1-ol, (6aR,10aR)-6,6,9-trimethyl-3-(pent-4-en-1-yl)-6H,6aH,7H,8H, 10aH-benzo[c]isochromen-1-ol, (6aR,10aR)-3-(hex-5-yn-1-yl)-6,6,9-trimethyl-6H,6aH, 7H,8H, 10aH-benzo[c]isochromen-1-ol.

Most preferably, compound (VII) is delta-9-tetrahydrocannabinol (THC).

The present invention further relates to a process for the production of a compound of Formula (V), wherein the process comprises producing a compound of Formula (I) as described herein and converting the compound of Formula (I) to the compound of Formula (V) in the presence of any enzyme capable of mediating the conversion.

Conversion of the compound of Formula (I) to the compound of Formula (V) can be mediated by tetrahydrocannabinolic acid synthase (THCAS; EC 1.21.3.7, GenBank accession AB057805, GenBank version AB057805.1, SEQ ID NO: 1). In the context of the present invention, conversion of the compound of Formula (I) to the compound of Formula (V) can also be mediated by an enzyme with an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of THCAS (EC 1.21.3.7, GenBank accession AB057805, GenBank version AB057805.1, SEQ ID NO: 1) and which is characterized by having the activity to convert the compound of Formula (I) to the compound of Formula (V). In the context of the present invention, conversion of the compound of Formula (I) to the compound of Formula (V) can also be mediated by (an) enzyme(s) which is/are obtained from (a) naturally occurring enzyme(s), e.g., by the introduction of mutations or other alterations which, e.g., alter or improve the enzymatic activity, the stability and which is characterized by having the activity to convert the compound of Formula (I) to the compound of Formula (V). Conversion of the compound of Formula (I) to the compound of Formula (V) can also be mediated by cannabidiolic acid synthase (CBDAS; EC 1.21.3.8, GenBank accession no: AB292682, GenBank version no: AB292682.1, SEQ ID NO: 2). In the context of the present invention, conversion of the compound of Formula (I) to the compound of Formula (V) can also be mediated by an enzyme with an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of CBDAS (EC 1.21.3.8, GenBank accession no: AB292682, GenBank version no: AB292682.1, SEQ ID NO: 2) and which is characterized by having the activity to convert the compound of Formula (I) to the compound of Formula (V). In the context of the present invention, conversion of the compound of Formula (I) to the compound of Formula (V) can also be mediated by (an) enzyme(s) which is/are obtained from (a) naturally occurring enzyme(s), e.g., by the introduction of mutations or other alterations which, e.g., alter or improve the enzymatic activity, the stability and which is characterized by having the activity to convert the compound of Formula (I) to the compound of Formula (V). Conversion of the compound of Formula (I) to the compound of Formula (V) can also be mediated by cannabichromenic acid synthase (CBCAS; EC 1.3.3.-, sequence as published in WO 2015/196275 A1 (SEQ 5), SEQ ID NO: 3). In the context of the present invention, conversion of the compound of Formula (I) to the compound of Formula (V) can also be mediated by an enzyme with an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of CBCAS (EC 1.3.3.-, sequence as published in WO 2015/196275 A1 (SEQ 5), SEQ ID NO: 3) and which is characterized by having the activity to convert the compound of Formula (I) to the compound of Formula (V). In the context of the present invention, conversion of the compound of Formula (I) to the compound of Formula (V) can also be mediated by (an) enzyme(s) which is/are obtained from (a) naturally occurring enzyme(s), e.g., by the introduction of mutations or other alterations which, e.g., alter or improve the enzymatic activity, the stability and which is characterized by having the activity to convert the compound of Formula (I) to the compound of Formula (V).

In the present invention, a compound of Formula (V) is considered to have the following structure:

Formula (V)

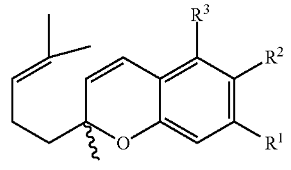

wherein $R^1$, $R^2$ and $R^3$ are as defined for Formula (I).

In the compound of formula (V), it is preferred that the following definitions apply, either independently or in any combination thereof: $R^1$ is preferably linear or branched $C_{4-6}$ alkyl, more preferably, $R^1$ is a $C_5$ alkyl, most preferably, $R^1$ is $C_5H_{11}$, $R^2$ is preferably-C(O) OH and $R^3$ is preferably-OH.

Examples of compounds with the formula (V) to be produced in the presence of the plant extract having prenyltransferase activity according to the present invention include the following compounds:

cannabichrovarinic acid (CBCVA); cannabichromenic acid (CBCA); 7-butyl-5-hydroxy-2-methyl-2-(4-methylpent-3-en-1-yl)-2H-chromene-6-carboxylic acid; 7-hexyl-5-hydroxy-2-methyl-2-(4-methylpent-3-en-1-yl)-2H-chromene-6-carboxylic acid; 5-hydroxy-2-methyl-2-(4-methylpent-3-en-1-yl)-7-(3-methylpentyl)-2H-chromene-6-carboxylic acid; 5-hydroxy-2-methyl-2-(4-methylpent-3-en-1-yl)-7-(pent-4-en-1-yl)-2H-chromene-6-carboxylic acid; 7-(hex-5-yn-1-yl)-5-hydroxy-2-methyl-2-(4-methylpent-3-en-1-yl)-2H-chromene-6-carboxylic acid; 2-methyl-2-(4-methylpent-3-en-1-yl)-7-propyl-5-{[(3R,4R,5S,6S)-4,5,6-trihydroxy-3-(hydroxymethyl) oxan-2-yl]oxy}-2H-chromene-6-carboxylic acid; 2-methyl-2-(4-methylpent-3-en-1-yl)-7-pentyl-5-{[(3R,4R,5S,6S)-4,5,6-trihydroxy-3-(hydroxymethyl) oxan-2-yl]oxy}-2H-chromene-6-carboxylic acid; 7-butyl-2-methyl-2-(4-methylpent-3-en-1-yl)-5-{[(3R,4R,5S,6S)-4,5,6-trihydroxy-3-(hydroxymethyl) oxan-2-yl]oxy}-2H-chromene-6-carboxylic acid; 7-hexyl-2-methyl-2-(4-methylpent-3-en-1-yl)-5-{[(3R,4R,5S,6S)-4,5,6-trihydroxy-3-(hydroxymethyl) oxan-2-yl]oxy}-2H-chromene-6-carboxylic acid; 2-methyl-2-(4-methylpent-3-en-1-yl)-7-(3-methylpentyl)-5-{[(3R,4R,5S,6S)-4,5,6-trihydroxy-3-(hydroxymethyl) oxan-2-yl]oxy}-2H-chromene-6-carboxylic acid; 2-methyl-2-(4-methylpent-3-en-1-yl)-7-(pent-4-en-1-yl)-5-{[(3R,4R,5S,6S)-4,5,6-trihydroxy-3-(hydroxymethyl) oxan-2-yl]oxy}-2H-chromene-6-carboxylic acid; and 7-(hex-5-en-1-yl)-2-methyl-2-(4-methylpent-3-en-1-yl)-5-{[(3R,4R,5S,6S)-4,5,6-trihydroxy-3-(hydroxymethyl) oxan-2-yl]oxy}-2H-chromene-6-carboxylic acid.

Examples of compounds with the formula (V) to be produced in the presence of the plant extract having prenyltransferase activity according to the present invention are preferably the following compounds:

5-hydroxy-2-methyl-2-(4-methylpent-3-enyl)-7-pentyl-chromene-6-carboxylic acid, 7-butyl-5-hydroxy-2-methyl-2-(4-methylpent-3-en-1-yl)-2H-chromene-6-carboxylic acid, 7-hexyl-5-hydroxy-2-methyl-2-(4-methylpent-3-en-1-yl)-2H-chromene-6-carboxylic acid, 5-hydroxy-2-methyl-2-(4-methylpent-3-en-1-yl)-7-(3-methylpentyl)-2H-chromene-6-carboxylic acid, 5-hydroxy-2-methyl-2-(4-methylpent-3-en-1-yl)-7-(pent-4-en-1-yl)-2H-chromene-6-carboxylic acid, 7-(hex-5-yn-1-yl)-5-hydroxy-2-methyl-2-(4-methylpent-3-en-1-yl)-2H-chromene-6-carboxylic acid.

Most preferably, compound (IV) is cannabichromenic acid (CBCA).

In the present invention, a compound of Formula (V) produced as described herein, is further decarboxylated to a compound of Formula (VIII). As will be understood, the compound to be decarboxylated preferably has a —C(O)OH group as $R^2$. A compound of Formula (VIII) is considered to have the following structure:

Formula (VIII)

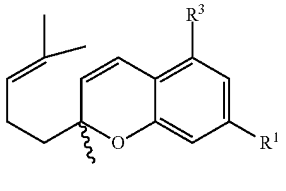

wherein $R^1$ and $R^3$ are as defined for Formula (I).

In the compound of formula (VIII), it is preferred that the following definitions apply, either independently or in any combination thereof: $R^1$ is preferably linear or branched $C_{4-6}$ alkyl, more preferably, $R^1$ is a $C_5$ alkyl, most preferably, $R^1$ is $C_5H_{11}$, and $R^3$ is preferably —OH.

Examples of compounds with the formula (VIII) according to the present invention include the following compounds:

cannabichrovarin (CBCV); cannabichromene (CBC); 7-butyl-2-methyl-2-(4-methylpent-3-en-1-yl)-2H-chromen-5-ol; 7-hexyl-2-methyl-2-(4-methylpent-3-en-1-yl)-2H-chromen-5-ol; 2-methyl-2-(4-methylpent-3-en-1-yl)-7-(3-methylpentyl)-2H-chromen-5-ol; 2-methyl-2-(4-methylpent-3-en-1-yl)-7-(pent-4-en-1-yl)-2H-chromen-5-ol; 7-(hex-5-yn-1-yl)-2-methyl-2-(4-methylpent-3-en-1-yl)-2H-chromen-5-ol; (2S,3S,4R,5R)-5-(hydroxymethyl)-6-{[2-methyl-2-(4-methylpent-3-en-1-yl)-7-propyl-2H-chromen-5-yl]oxy}oxane-2,3,4-triol; (2S,3S,4R,5R)-5-(hydroxymethyl)-6-{[2-methyl-2-(4-methylpent-3-en-1-yl)-7-pentyl-2H-chromen-5-yl]oxy}oxane-2,3,4-triol; (2S,3S,4R,5R)-6-{[7-butyl-2-methyl-2-(4-methylpent-3-en-1-yl)-2H-chromen-5-yl]oxy}-5-(hydroxymethyl) oxane-2,3,4-triol; (2S,3S,4R,5R)-6-{[7-hexyl-2-methyl-2-(4-methylpent-3-en-1-yl)-2H-chromen-5-yl]oxy}-5-(hydroxymethyl) oxane-2,3,4-triol; (2S,3S,4R,5R)-5-(hydroxymethyl)-6-{[2-methyl-2-(4-methylpent-3-en-1-yl)-7-(3-methylpentyl)-2H-chromen-5-yl]oxy}oxane-2,3,4-triol; (2S,3S,4R,5R)-5-(hydroxymethyl)-6-{[2-methyl-2-(4-methylpent-3-en-1-yl)-7-(pent-4-en-1-yl)-2H-chromen-5-yl]oxy}oxane-2,3,4-triol; and (2S,3S,4R,5R)-6-{[7-(hex-5-yn-1-yl)-2-methyl-2-(4-methylpent-3-en-1-yl)-2H-chromen-5-yl]oxy}-5-(hydroxymethyl) oxane-2,3,4-triol.

Examples of compounds with the formula (VIII) according to the present invention are preferably the following compounds:

2-methyl-2-(4-methylpent-3-enyl)-7-pentyl-5-chromen-5-ol, 7-butyl-2-methyl-2-(4-methylpent-3-en-1-yl)-2H-chromen-5-ol, 7-hexyl-2-methyl-2-(4-methylpent-3-en-1-yl)-2H-chromen-5-ol, 2-methyl-2-(4-methylpent-3-en-1-yl)-7-(3-methylpentyl)-2H-chromen-5-ol, 2-methyl-2-(4-methylpent-3-en-1-yl)-7-(pent-4-en-1-yl)-2H-chromen-5-ol, 7-(hex-5-yn-1-yl)-2-methyl-2-(4-methylpent-3-en-1-yl)-2H-chromen-5-ol.

Most preferably, compound (VIII) is cannabichromene (CBC).

The present invention further relates to a process for the production of a compound of Formula (VI), wherein the process comprises producing a compound of Formula (I) as described herein and converting the compound of Formula (I) to the compound of Formula (VI) in the presence of any enzyme capable of mediating the conversion.

Conversion of the compound of Formula (I) to the compound of Formula (VI) can be mediated by cannabidiolic acid synthase (CBDAS; EC 1.21.3.8, GenBank accession no: AB292682, GenBank version no: AB292682.1, SEQ ID NO: 2). In the context of the present invention, conversion of the compound of Formula (I) to the compound of Formula (VI) can also be mediated by an enzyme with an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of CBDAS (EC 1.21.3.8, GenBank accession no: AB292682, GenBank version no: AB292682.1, SEQ ID NO: 2) and which is characterized by having the activity to convert the compound of Formula (I) to the compound of Formula (VI). In the context of the present invention, conversion of the compound of Formula (I) to the compound of Formula (VI) can also be mediated by (an) enzyme(s) which is/are obtained from (a) naturally occurring enzyme(s), e.g., by the introduction of mutations or other alterations which, e.g., alter or improve the enzymatic activity, the stability and which is characterized by having the activity to convert the compound of Formula (I) to the compound of Formula (VI).

In the present invention, a compound of Formula (VI) is considered to have the following structure:

Formula (VI)

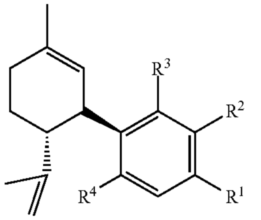

wherein $R^1$, $R^2$, $R^3$ and $R^4$ are as defined for Formula (I).

In the compound of formula (VI), it is preferred that the following definitions apply, either independently or in any combination thereof: $R^1$ is preferably linear or branched $C_{4-6}$ alkyl, more preferably, $R^1$ is a $C_5$ alkyl, most preferably, $R^1$ is $C_5H_{11}$, $R^2$ is preferably-C(O) OH, $R^3$ is preferably —OH and $R^4$ is preferably-OH.

Examples of compounds with the formula (VI) to be produced according to the process of the present invention include the following compounds:

cannabidivarinic acid (CBDVA); cannabidiolic acid (CBDA); 6-butyl-2,4-dihydroxy-3-[(1R,6R)-3-methyl-6-(prop-1-en-2-yl)cyclohex-2-en-1-yl]benzoic acid; 6-hexyl-2,4-dihydroxy-3-[(1R,6R)-3-methyl-6-(prop-1-en-2-yl)cyclohex-2-en-1-yl]benzoic acid; 2,4-dihydroxy-3-[(1R,6R)-3-methyl-6-(prop-1-en-2-yl)cyclohex-2-en-1-yl]-6-(3-methylpentyl)benzoic acid; 2,4-dihydroxy-3-[(1R,6R)-3-methyl-6-(prop-1-en-2-yl) cyclohex-2-en-1-yl]-6-(pent-4-en-1-yl)benzoic acid; 6-(hex-5-yn-1-yl)-2,4-dihydroxy-3-[(1R,6R)-3-methyl-6-(prop-1-en-2-yl)cyclohex-2-en-1-yl]benzoic acid; 4-hydroxy-3-[(1R,6R)-3-methyl-6-(prop-1-en-2-yl)cyclohex-2-en-1-yl]-6-propyl-2-{[(3R,4R,5S,6S)-4,5,6-trihydroxy-3-(hydroxymethyl) oxan-2-yl]oxy}benzoic acid; 4-hydroxy-3-[(1R,6R)-3-methyl-6-(prop-1-en-2-yl)cyclohex-2-en-1-yl]-6-pentyl-2-{[(3R,4R,5S,6S)-4,5,6-trihydroxy-3-(hydroxymethyl) oxan-2-yl]oxy}benzoic acid; 6-butyl-4-hydroxy-3-[(1R,6R)-3-methyl-6-(prop-1-en-2-yl)cyclohex-2-en-1-yl]-2-{[(3R,4R,5S,6S)-4,5,6-trihydroxy-3-(hydroxymethyl) oxan-2-yl]oxy}benzoic acid; 6-hexyl-4-hydroxy-3-[(1R,6R)-3-methyl-6-(prop-1-en-2-yl)cyclohex-2-en-1-yl]-2-{[(3R,4R,5S,6S)-4,5,6-trihydroxy-3-(hydroxymethyl) oxan-2-yl]oxy}benzoic acid; 4-hydroxy-3-[(1R,6R)-3-methyl-6-(prop-1-en-2-yl)cyclohex-2-en-1-yl]-6-(3-methylpentyl)-2-{[(3R,4R,5S,6S)-4,5,6-trihydroxy-3-(hydroxymethyl) oxan-2-yl]oxy}benzoic acid; 4-hydroxy-3-[(1R,6R)-3-methyl-6-(prop-1-en-2-yl)cyclohex-2-en-1-yl]-6-(pent-4-en-1-yl)-2-{[(3R,4R,5S,6S)-4,5,6-trihydroxy-3-(hydroxymethyl) oxan-2-yl]oxy}benzoic acid; and 6-(hex-5-yn-1-yl)-4-hydroxy-3-[(1R,6R)-3-methyl-6-(prop-1-en-2-yl)cyclohex-2-en-1-yl]-2-{[(3R,4R,5S,6S)-4,5,6-trihydroxy-3-(hydroxymethyl) oxan-2-yl]oxy}benzoic acid.

Examples of compounds with the formula (VI) to be produced according to the process of the present invention are preferably the following compounds:

2,4-dihydroxy-3-[(1R,6R)-3-methyl-6-prop-1-en-2-ylcyclohex-2-en-1-yl]-6-pentylbenzoic acid, 6-butyl-2,4-dihydroxy-3-[(1R,6R)-3-methyl-6-(prop-1-en-2-yl)cyclohex-2-en-1-yl]benzoic acid, 6-hexyl-2,4-dihydroxy-3-[(1R,6R)-3-methyl-6-(prop-1-en-2-yl)cyclohex-2-en-1-yl]benzoic acid, 2,4-dihydroxy-3-[(1R,6R)-3-methyl-6-(prop-1-en-2-yl)cyclohex-2-en-1-yl]-6-(3-methylpentyl)benzoic acid, 2,4-dihydroxy-3-[(1R,6R)-3-methyl-6-(prop-1-en-2-yl)cyclohex-2-en-1-yl]-6-(pent-4-en-1-yl)benzoic acid, 6-(hex-5-yn-1-yl)-2,4-dihydroxy-3-[(1R,6R)-3-methyl-6-(prop-1-en-2-yl) cyclohex-2-en-1-yl]benzoic acid.

Most preferably, compound (VI) is cannabidiolic acid (CBDA).

In the present invention, a compound of Formula (VI) produced as described herein, is further decarboxylated to a compound of Formula (IX). As will be understood, the compound to be decarboxylated preferably has a —C(O)OH group as $R^2$. A compound of Formula (IX) is considered to have the following structure:

Formula (IX)

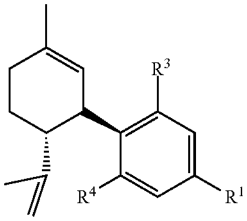

wherein $R^1$, $R^3$ and $R^4$ are as defined for Formula (I).

In the compound of formula (IX), it is preferred that the following definitions apply, either independently or in any combination thereof: $R^1$ is preferably linear or branched $C_{4-6}$ alkyl, more preferably, $R^1$ is a $C_5$ alkyl, most preferably, $R^1$ is $C_5H_{11}$, $R^3$ is preferably-OH and $R^4$ is preferably-OH.

Examples of compounds with the formula (IX) according to the present invention include the following compounds:

cannabidivarin (CBDV); cannabidiol (CBD); 5-butyl-2-[(1R,6R)-3-methyl-6-(prop-1-en-2-yl)cyclohex-2-en-1-yl]benzene-1,3-diol; 5-hexyl-2-[(1R,6R)-3-methyl-6-(prop-1-en-2-yl)cyclohex-2-en-1-yl]benzene-1,3-diol; 2-[(1R,6R)-3-methyl-6-(prop-1-en-2-yl) cyclohex-2-en-1-yl]-5-(3-methylpentyl)benzene-1,3-diol; 2-[(1R,6R)-3-methyl-6-(prop-1-en-2-yl) cyclohex-2-en-1-yl]-5-(pent-4-en-1-yl)benzene-1,3-diol; 5-(hex-5-yn-1-yl)-2-[(1R,6R)-3-methyl-6-(prop-1-en-2-yl)cyclohex-2-en-1yl]benzene-1,3-diol; (2S,3S,4R,5R)-6-{3-hydroxy-2-[(1R,6R)-3-methyl-6-(prop-1-en-2-yl)cyclohex-2-en-1-yl]-5-propylphenoxy}-5-(hydroxymethyl) oxane-2,3,4-triol; (2S,3S,4R,5R)-6-{3-hydroxy-2-[(1R,6R)-3-methyl-6-(prop-1-en-2-yl) cyclohex-2-en-1-yl]-5-pentylphenoxy}-5-(hydroxymethyl) oxane-2,3,4-triol; (2S,3S,4R,5R)-6-{5-butyl-3-hydroxy-2-[(1R,6R)-3-methyl-6-(prop-1-en-2-yl)cyclohex-2-en-1-yl]phenoxy}-5-(hydroxymethyl) oxane-2,3,4-triol; (2S,3S,4R,5R)-6-{5-hexyl-3-hydroxy-2-[(1R,6R)-3-methyl-6-(prop-1-en-2-yl)cyclohex-2-en-1-yl]phenoxy}-5-(hydroxymethyl) oxane-2,3,4-triol; (2S,3S,4R,5R)-6-{3-hydroxy-2-[(1R,6R)-3-methyl-6-(prop-1-en-2-yl) cyclohex-2-en-1-yl]-5-(3-methylpentyl) phenoxy}-5-(hydroxymethyl) oxane-2,3,4-triol; ((2S,3S,4R,5R)-6-{3-hydroxy-2-[(1R,6R)-3-methyl-6-(prop-1-en-2-yl) cyclohex-2-en-1-yl]-5-(pent-4-en-1-yl) phenoxy}-5-(hydroxymethyl) oxane-2,3,4-triol; and (2S,3S,4R,5R)-6-[5-(hex-5-yn-1-yl)-3-hydroxy-2-[(1R,6R)-3-methyl-6-(prop-1-en-2-yl)cyclohex-2-en-1-yl] phenoxy]-5-(hydroxymethyl) oxane-2,3,4-triol.

Examples of compounds with the formula (IX) according to the present invention are preferably the following compounds:

2-[(1R,6R)-3-methyl-6(-prop-1-en-2-yl)cyclohex-2-en-1-yl]-5-pentylbenzene-1,3-diol, 5-butyl-2-[(1R,6R)-3-methyl-6-(prop-1-en-2-yl)cyclohex-2-en-1-yl]benzene-1,3-diol, 5-hexyl-2-[(1R,6R)-3-methyl-6-(prop-1-en-2-yl)cyclohex-2-en-1-yl]benzene-1,3-diol, 2-[(1R,6R)-3-methyl-6-(prop-1-en-2-yl)cyclohex-2-en-1-yl]-5-(3-methylpentyl)benzene-1,3-diol, 2-[(1R,6R)-3-methyl-6-(prop-1-en-2-yl)cyclohex-2-en-1-yl]-5-(pent-4-en-1-yl)benzene-1,3-diol, 5-(hex-5-yn-1-yl)-2-[(1R,6R)-3-methyl-6-(prop-1-en-2-yl)cyclohex-2-en-1yl]benzene-1,3-diol.

Most preferably, compound (VIII) is cannabidiol (CBD).

Luo et al. (Nature. (2019), 567:123-126) has proved that CBGA and corresponding cannabinoid analogues can be produced from the fatty acid precursors hexanoic acid, pentanoic acid, heptanoic acid, 4-methylhexanoic acid, 5-hexenoic acid and 6-heptynoic acid by isoenzyme CsPT4 (a prenyltransferase of *Cannabis sativa*). The data of Luo et al. render it plausible that the compounds with the formula (I) and (IV) to (IX), wherein $R^1$ is selected from linear or branched $C_{1-10}$ alkyl, linear $C_{2-10}$ alkenyl and linear $C_{2-10}$ alkynyl, can be produced in the presence of a plant extract having prenyltransferase activity as disclosed herein.

In the present invention, production of compounds of the formula (VII), (VIII) and (IX) by the process as described herein is accomplished by decarboxylation reaction. As will be understood, the compound to be decarboxylated preferably has a —C(O)OH group as $R^2$. Such reaction is typically a result of nonenzymatic decarboxylation during storage or induced by heat or sunlight. In the context of the present invention, the reaction is induced by heat with a minimum temperature of 80° C., 85° C., 90° C. or 100° C., preferably at a temperature between 80° C. and 250° C., more preferably between 120° C. and 250° C., most preferably between 150° C. and 250° C.

The term "conversion" as used herein can be accomplished by an exogenous stimulus or can be accomplished endogenously. Exogenously, suitable enzymes, preferably THCAS, CBDAS and/or CBCAS as described herein, might be added to the plant extract having prenyltransferase activity prior to or following production of a compound of Formula (I) to mediate conversion of the compound of Formula (I) to the compound of Formula (IV), (V) and/or (VI). In this context, the enzyme/s may be in any suitable form allowing the enzymatic reaction to take place. They may be purified or partially purified or in the form of crude cellular extracts or partially purified extracts. It is also possible that the enzymes are immobilized on a suitable carrier.

It is preferred that suitable enzymes, preferably THCAS, CBDAS and/or CBCAS as described herein, are endogenously produced by the plant extract having prenyltransferase activity to mediate conversion of the compound of Formula (I) to the compound of Formula (IV), (V) and/or (VI). Such heterologous production can be achieved by genetically modifying the plant, plant cell or liquid cell culture used to provide the plant extract by methods already described herein. In case the plant extract is obtained from solid plant material, introduction of a foreign nucleic acid molecule ensuring heterologous expression of an enzyme converting the compound of Formula (I) to the compound of Formula (IV), (V) and/or (VI), preferably THCAS, CBDAS and/or CBCAS as described herein, may be performed by *Agrobacterium*-mediated transformation of a transgenic construct encoding the respective enzyme/s. The method of *Agrobacterium*-mediated transformation is known by the person skilled in the art and is furthermore described in the appended examples. Expression of the enzyme/s may occur constitutively or in an induced or regulated manner. Expression further comprises transcription of the heterologous DNA sequence, preferably into a translatable mRNA. Regulatory elements ensuring expression in plants, are well known to those skilled in the art. They encompass promoters, enhancers, termination signals, targeting signals and the like. For example, the transgenic construct may include a targeting sequence to ensure specific subcellular e.g. cytosolic, chloroplast or endoplasmatic reticulum (ER) localization of the enzyme. The importance of subcellular localization for enzyme functionality has been reported in a previous study (Geissler et al., Biotechnol Lett. (2018), 40 (6): 981-987). In the context of the present invention, ER/apoplast or vacuolar targeting are preferred. Suitable cloning techniques are well-known and are described, for instance, in Sambrook and Russell, Cold Spring Harbor Laboratory Press (2001), Vol. 1, $4^{th}$ edition.

As disclosed herein, enzymes, preferably THCAS, CBDAS and/or CBCAS, mediating conversion of the compound of Formula (I) to the compound of Formula (IV), (V) and/or (VI) may be endogenously produced by the plant extract having prenyltransferase activity. Accordingly, the plant, plant cell or liquid cell culture used to provide the plant extract may be obtained from any plant or plant cell culture having prenyltransferase activity as defined herein above except for those naturally building phytocannabinoid substances. As such, *Cannabis sativa* and other plant species naturally producing phytocannabinoids, phytocannabinoid-like substances or cannabimimetic substances as described herein are excluded.

In the present invention, product specificity of the process for the production of a compound of Formula IV, V and/or VI comprising producing a compound of Formula (I) according to the present invention and converting the compound of Formula (I) to the compound of Formula IV, V and/or VI as described herein, may be dependent on pH and solvent composition of the reaction medium. The reaction medium is considered to be a liquid medium, in which the enzymatic reaction, i.e. the conversion of Formula (I) to the compound of Formula (IV), (V) and/or (VI) takes place. The reaction medium may be the native plant extract according to the present invention or the plant extract may be modified by changing its composition, i.e. by changing the pH or by adding one or more solvents in a preferred concentration.

Accordingly, prior to or after reacting the plant extract having prenyltransferase activity with compounds having the formula (II) or (III) as described herein, the plant extract may further be pH-adjusted or may be mixed with a solvent. Dependency of product specificity of THCAS, CBCAS and CBDAS on pH has been described previously (Zirpel et al., J. Biotechnol (2018), 20; 284:17-26). The study by Zirpel et al. discloses that product specificity of THCAS was changed by a pH shift from pH 4.5 to pH 7.0 from THCA as produced main product to CBCA as produced main product. In the context of the present invention, pH can be shifted in any way suitable to change product specificity of the enzymes capable of mediating the conversion of the compound of Formula (I) to the compound of Formula (IV), (V) and/or (VI) as disclosed herein. The solvent can be any non-aqueous solvent but is preferably an organic solvent.

Examples thereof include 1-propanol, tetrahydrofuran, 1,4-dioxane, dimethyl formamide, methanol, ethanol, dichlormethane, dimethylsulfoxide (DMSO), isopropanol, acetone and acetonitrile but are not limited thereto. More preferably, the solvent is selected from the group of methanol, ethanol, dichlormethane, dimethylsulfoxide (DMSO), isopropanol, acetone and acetonitrile. The solvent can be added to the plant extract or the assay medium to a final amount of between 0.5% vol and 14% vol but is preferably added to a final amount of between 1.8% vol and 7.2% vol. As shown in the appended examples, addition of non-aqueous solvents, specifically in higher amounts, changed product specificity of THCAS and CBCAS as described herein from THCA to CBCA production. Most preferably, solvent and/or pH are chosen in such way, that product ratios are shifted to production of non-psychotropic phytocannabinoids.

Specifically, the present invention relates to the following items:

[1] A process for the production of a compound of Formula (I)

Formula (I)

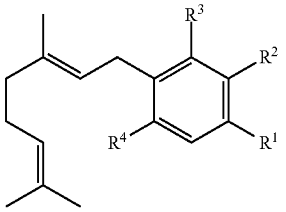

wherein $R^1$ is selected from -hydrogen, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl), -(optionally substituted linear or branched $C_{2-10}$ alkynyl), -(optionally substituted $C_{3-10}$ cycloalkyl), -(optionally substituted $C_{6-10}$ aryl), -(optionally substituted linear or branched $C_{1-10}$ alkylene)-(optionally substituted $C_{6-10}$ aryl), -(optionally substituted linear or branched $C_{2-10}$ alkenylene)-(optionally substituted $C_{6-10}$ aryl) and -(optionally substituted linear or branched $C_{2-10}$ alkynylene)-(optionally substituted $C_{6-10}$ aryl); $R^2$ is selected from -hydrogen, —C(O)OH, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl), -(optionally substituted linear or branched $C_{2-10}$ alkynyl), -(optionally substituted $C_{3-10}$ cycloalkyl), -(optionally substituted $C_{6-10}$ aryl), -(optionally substituted linear or branched $C_{1-10}$ alkylene)-(optionally substituted $C_{6-10}$ aryl), -(optionally substituted linear or branched $C_{2-10}$ alkenylene)-(optionally substituted $C_{6-10}$ aryl) and -(optionally substituted linear or branched $C_{2-10}$ alkynylene)-(optionally substituted $C_{6-10}$ aryl); $R^3$ is selected from —OH, —O-glycosyl, —O($C_{1-6}$ alkyl), -halogen, —SH, —S($C_{1-6}$ alkyl), —$NH_2$, —NH($C_{1-6}$ alkyl), —N($C_{1-6}$ alkyl)$_2$, -piperidyl and -morpholinyl; $R^4$ is selected from —OH, —O-glycosyl, —O($C_{1-6}$ alkyl), -halogen, —SH, —S($C_{1-6}$ alkyl), —$NH_2$, —NH($C_{1-6}$ alkyl), —N($C_{1-6}$ alkyl)$_2$, -piperidyl and -morpholinyl;

wherein the one or more optional substituents of alkyl, alkenyl, alkynyl, alkylene, alkenylene and alkynylene are preferably independently selected from -halogen, —OH, —O—$C_{1-6}$ alkyl and —CN, and wherein the one or more optional substituents of cycloalkyl and aryl are preferably independently selected from —$C_{1-6}$, -halogen, —OH, —O—$C_{1-6}$ alkyl and —CN;

wherein the process comprises the step of reacting a plant extract having prenyltransferase activity with a compound of Formula (II)

Formula (II)

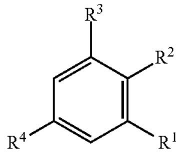

wherein $R^1$, $R^2$, $R^3$ and $R^4$ are as defined above, and geranyl pyrophosphate (GPP) having the following Formula (III)

Formula (III)

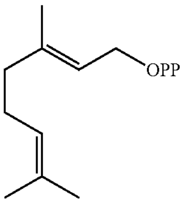

wherein PP represents pyrophosphate, to produce the compound of Formula (I), wherein the plant extract is not a *Cannabis sativa, Acmella olera-*

*cea, Echinaceae* angustifolia, *Echinaceae purpurea, Helichrysum umbraculigerum, Heliopsis helianthoides, Piper nigrum, Radula marginata*, and/or *Radula perrottetii* plant extract.

[2] A process for the production of a compound of the following Formula (IV)

Formula (IV)

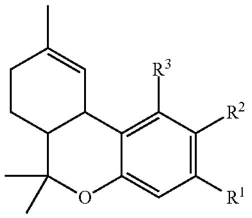

wherein $R^1$ is selected from -hydrogen, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl), -(optionally substituted linear or branched $C_{2-10}$ alkynyl), -(optionally substituted $C_{3-10}$ cycloalkyl), -(optionally substituted $C_{6-10}$ aryl), -(optionally substituted linear or branched $C_{1-10}$ alkylene)-(optionally substituted $C_{6-10}$ aryl), -(optionally substituted linear or branched $C_{2-10}$ alkenylene)-(optionally substituted $C_{6-10}$ aryl) and -(optionally substituted linear or branched $C_{2-10}$ alkynylene)-(optionally substituted $C_{6-10}$ aryl); $R^2$ is selected from -hydrogen, —C(O)OH, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl), -(optionally substituted linear or branched $C_{2-10}$ alkynyl), -(optionally substituted $C_{3-10}$ cycloalkyl), -(optionally substituted $C_{6-10}$ aryl), -(optionally substituted linear or branched $C_{1-10}$ alkylene)-(optionally substituted $C_{6-10}$ aryl), -(optionally substituted linear or branched $C_{2-10}$ alkenylene)-(optionally substituted $C_{6-10}$ aryl) and -(optionally substituted linear or branched $C_{2-10}$ alkynylene)-(optionally substituted $C_{6-10}$ aryl);

$R^3$ is selected from —OH, —O-glycosyl, —O($C_{1-6}$ alkyl), -halogen, —SH, —S($C_{1-6}$ alkyl), —$NH_2$, —NH($C_{1-6}$ alkyl), —N($C_{1-6}$ alkyl)$_2$, -piperidyl and -morpholinyl;

wherein the one or more optional substituents of alkyl, alkenyl, alkynyl, alkylene, alkenylene and alkynylene are preferably independently selected from -halogen, —OH, —O—$C_{1-6}$ alkyl and —CN, and wherein the one or more optional substituents of cycloalkyl and aryl are preferably independently selected from —$C_{1-6}$, -halogen, —OH, —O—$C_{1-6}$ alkyl and —CN.

wherein the process comprises producing a compound of Formula (I), wherein $R^4$ is —OH, by the process of [1] and converting the compound of Formula (I) to the compound of Formula (IV) in the presence of the tetrahydrocannabinolic acid synthase (THCAS; EC 1.21.3.7).

[3] The process of [2], wherein the compound of Formula (IV), wherein $R^2$ is —C(O)OH, is decarboxylated to a compound of Formula (VII)

Formula (VII)

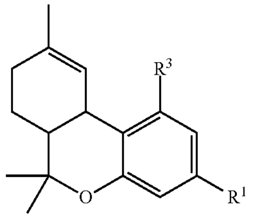

wherein $R^1$ and $R^3$ are as defined in [2].

[4] A process for the production of a compound of Formula (V)

Formula (V)

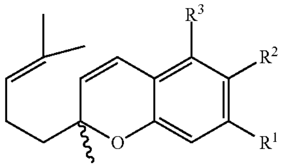

wherein $R^1$ is selected from -hydrogen, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl), -(optionally substituted linear or branched $C_{2-10}$ alkynyl), -(optionally substituted $C_{3-10}$ cycloalkyl), -(optionally substituted $C_{6-10}$ aryl), -(optionally substituted linear or branched $C_{1-10}$ alkylene)-(optionally substituted $C_{6-10}$ aryl), -(optionally substituted linear or branched $C_{2-10}$ alkenylene)-(optionally substituted $C_{6-10}$ aryl) and -(optionally substituted linear or branched $C_{2-10}$ alkynylene)-(optionally substituted $C_{6-10}$ aryl); $R^2$ is selected from -hydrogen, —C(O)OH, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl), -(optionally substituted linear or branched $C_{2-10}$ alkynyl), -(optionally substituted $C_{3-10}$ cycloalkyl), -(optionally substituted $C_{6-10}$ aryl), -(optionally substituted linear or branched $C_{1-10}$ alkylene)-(optionally substituted $C_{6-10}$ aryl), -(optionally substituted linear or branched $C_{2-10}$ alkenylene)-(optionally substituted $C_{6-10}$ aryl) and -(optionally substituted linear or branched $C_{2-10}$ alkynylene)-(optionally substituted $C_{6-10}$ aryl);

$R^3$ is selected from —OH, —O-glycosyl, —O($C_{1-6}$ alkyl), -halogen, —SH, —S($C_{1-6}$ alkyl), —$NH_2$, —NH($C_{1-6}$ alkyl), —N($C_{1-6}$ alkyl)$_2$, -piperidyl and -morpholinyl;

wherein the one or more optional substituents of alkyl, alkenyl, alkynyl, alkylene, alkenylene and alkynylene are preferably independently selected from -halogen, —OH, —O—$C_{1-6}$ alkyl and —CN, and wherein the one or more optional substituents of cycloalkyl and aryl are preferably independently selected from —$C_{1-6}$, -halogen, —OH, —O—$C_{1-6}$ alkyl and —CN;

wherein the process comprises producing a compound of Formula (I), wherein $R^4$ is —OH, by the process of [1] and converting the compound of Formula (I) to a compound of Formula (V) in the presence of the THCAS (EC 1.21.3.7), cannabidiolic acid synthase (CBDAS; EC 1.21.3.8) and/or cannabichromenic acid synthase (CBCAS; EC 1.3.3.-).

[5] The process of [4], wherein the compound of Formula (V), wherein $R^2$ is —C(O)OH, is decarboxylated to a compound of Formula (VIII)

Formula (VIII)

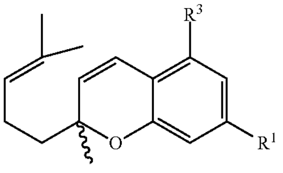

wherein $R^1$ and $R^3$ are as defined in [4].

[6] A process for the production of a compound of Formula (VI)

Formula (VI)

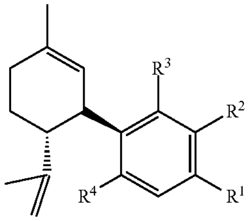

wherein $R^1$ is selected from -hydrogen, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl), -(optionally substituted linear or branched $C_{2-10}$ alkynyl), -(optionally substituted $C_{3-10}$ cycloalkyl), -(optionally substituted $C_{6-10}$ aryl), -(optionally substituted linear or branched $C_{1-10}$ alkylene)-(optionally substituted $C_{6-10}$ aryl), -(optionally substituted linear or branched $C_{2-10}$ alkenylene)-(optionally substituted $C_{6-10}$ aryl) and -(optionally substituted linear or branched $C_{2-10}$ alkynylene)-(optionally substituted $C_{6-10}$ aryl);

$R^2$ is selected from -hydrogen, —C(O)OH, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl), -(optionally substituted linear or branched $C_{2-10}$ alkynyl), -(optionally substituted $C_{3-10}$ cycloalkyl), -(optionally substituted $C_{6-10}$ aryl), -(optionally substituted linear or branched $C_{1-10}$ alkylene)-(optionally substituted $C_{6-10}$ aryl), -(optionally substituted linear or branched $C_{2-10}$ alkenylene)-(optionally substituted $C_{6-10}$ aryl) and -(optionally substituted linear or branched $C_{2-10}$ alkynylene)-(optionally substituted $C_{6-10}$ aryl);

$R^3$ is selected from —OH, —O-glycosyl, —O($C_{1-6}$ alkyl), -halogen, —SH, —S($C_{1-6}$ alkyl), —$NH_2$, —NH($C_{1-6}$ alkyl), —N($C_{1-6}$ alkyl)$_2$, -piperidyl and -morpholinyl;

$R^4$ is selected from —OH, —O-glycosyl, —O($C_{1-6}$ alkyl), -halogen, —SH, —S($C_{1-6}$ alkyl), —$NH_2$, —NH($C_{1-6}$ alkyl), —N($C_{1-6}$ alkyl)$_2$, -piperidyl and -morpholinyl;

wherein the one or more optional substituents of alkyl, alkenyl, alkynyl, alkylene, alkenylene and alkynylene are preferably independently selected from -halogen, —OH, —O—$C_{1-6}$ alkyl and —CN, and wherein the one or more optional substituents of cycloalkyl and aryl are preferably independently selected from —$C_{1-6}$, -halogen, —OH, —O—$C_{1-6}$ alkyl and —CN, wherein the process comprises producing a compound of Formula (I) by the process of claim [1] and converting the compound of Formula (I) to a compound of Formula (VI) in the presence of the CBDAS (EC 1.21.3.8).

[7] The process of [6], wherein the compound of Formula (VI), wherein $R^2$ is —C(O)OH, is decarboxylated to a compound of Formula (IX)

Formula (IX)

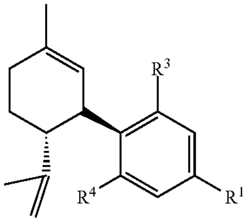

wherein $R^1$, $R^3$ and $R^4$ are as defined in [6].

[8] The process of any one of [1] to [7], wherein the plant extract is obtained from a plant which expresses an endogenous prenyltransferase.

[9] The process of [8], wherein the plant is a genetically modified plant expressing a heterologous THCAS (EC 1.21.3.7), CBDAS (EC 1.21.3.8) and/or CBCAS (EC 1.3.3.-).

[10] The process of any one of [1] to [9], wherein the plant extract is obtained from solid plant material with an extraction agent to obtain an extraction liquid containing the plant extract dissolved in said extraction liquid.

[11] The process of [10], wherein the extraction agent is an aqueous buffer selected from the group of TAPS, Bicine, Tricine, TAPSO, HEPES, TES, MOPS, PIPES, Cacodylate, MES, $Na_2HPO_4$, $NaH_2PO_4$, CHES, Acetic acid, Citric acid, Borate and $KH_2PO_4$.

[12] The process of any one of [1] to [9], wherein the plant extract is a liquid cell culture.

[13] The process of any one of [1] to [12], wherein the plant extract is obtained from a plant selected from the group consisting of *Lactuca sativa, Nepeta cataria, Nicotiana benthamiana, Nicotiana tabacum* and *Ocimum basilicum.*

[14] The process according to any of [1] to [13], wherein $R^1$ is selected from linear or branched $C_{1-10}$ alkyl, linear $C_{2-10}$ alkenyl and linear $C_{2-10}$ alkynyl, wherein the linear $C_{2-10}$ alkenyl contains not more than one C═C double bond, which is preferably a terminal C═C double bond, and the linear $C_{2-10}$ alkynyl contains not more than one C≡C triple bond, which is preferably a terminal C≡C triple bond, preferably, wherein $R^1$ is selected from n-pentyl, n-butyl, n-hexyl, 3-methylpentyl, 4-pentenyl and 5-hexynyl, more preferably, wherein $R^1$ is n-pentyl.

[15] The process according to any of to [14], wherein $R^2$ is selected from -hydrogen, —C(O)OH, -(optionally substituted linear or branched $C_{1-10}$ alkyl), —O-(optionally substituted linear or branched $C_{1-10}$ alkyl), —C(O)-(optionally substituted linear or branched $C_{1-10}$ alkyl), —C(O)—O-(optionally substituted linear or branched $C_{1-10}$ alkyl), -(optionally substituted linear or branched $C_{2-10}$ alkenyl) and -(optionally substituted linear or branched $C_{2-10}$ alkynyl); preferably, $R^2$ is selected from —C(O)OH, —C(O)-(optionally substituted linear or branched $C_{1-10}$ alkyl) and —C(O)—O-(optionally substituted linear or branched $C_{1-10}$ alkyl); more preferably, $R^2$ is selected from —C(O)OH and —C(O)—O-(optionally substituted linear or branched $C_{1-10}$ alkyl); most preferably, $R^2$ is —C(O)OH.

[16] The process according to any of [15], wherein $R^3$ is selected from —OH, —O-glycosyl, —O($C_{1-6}$ alkyl) and -halogen; preferably, $R^3$ is selected from —OH and —O-glycosyl; more preferably, $R^3$ is selected from —OH and —O-glucosyl; most preferably, $R^3$ is —OH.

[17] The process according to any of [16], wherein $R^4$ is selected from —OH, —O-glycosyl, —O($C_{1-6}$ alkyl) and -halogen; preferably, $R^4$ is selected from —OH and —O-glycosyl; more preferably, $R^4$ is selected from —OH and —O-glucosyl; most preferably, $R^4$ is —OH.

[18] The process according to any of [1] to [17], wherein the compound of Formula (I) is selected from the group consisting of cannabigerovarinic acid (CBGVA); cannabigerolic acid (CBGA); 6-butyl-3-[(2E)-3,7-dimethylocta-2,6-dien-1-yl]-2,4-dihydroxybenzoic acid 3-[(2E)-3,7-dimethylocta-2,6-dien-1-yl]-6-hexyl-2,4-dihydroxybenzoic acid; 3-[(2E)-3,7-dimethylocta-2,6-dien-1-yl]-2,4-dihydroxy-6-(3-methylpentyl)benzoic acid; 3-[(2E)-3,7-dimethylocta-2,6-dien-1-yl]-2,4-dihydroxy-6-(pent-4-en-1-yl)benzoic acid; 3-[(2E)-3,7-dimethylocta-2,6-dien-1-yl]-6-(hex-5-yn-1-yl)-2,4-dihydroxybenzoic acid; 3-[(2E)-3,7-dimethylocta-2,6-dien-1-yl]-2-hydroxy-6-propyl-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-2-hydroxy-6-pentyl-4-{[(3R,4R,5S,6S)-4,5,6-trihydroxy-3-(hydroxymethyl) oxan-2-yl]oxy}benzoic acid; 6-butyl-3-[(2E)-3,7-dimethylocta-2,6-dien-1-yl]-2-hydroxy-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-6-hexyl-2-hydroxy-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-2-hydroxy-6-(3-methylpentyl)-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-2-hydroxy-6-(pent-4-en-1-yl)-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-6-(hex-5-yn-1-yl)-2-hydroxy-4-{[(3R,4R,5S,6S)-4,5,6-trihydroxy-3-(hydroxymethyl) oxan-2-yl]oxy}benzoic acid; 3-[(2E)-3,7-dimethylocta-2,6-dien-1-yl]-4-hydroxy-6-propyl-2-{[(3S,4R,5S,6S)-4,5,6-trihydroxyoxan-3-yl]methoxy}benzoic acid; 3-[(2E)-3,7-dimethylocta-2,6-dien-1-yl]-4-hydroxy-6-pentyl-2-{[(3S,4R,5S,6S)-4,5,6-trihydroxyoxan-3-yl] methoxy}benzoic acid; 6-butyl-3-[(2E)-3,7-dimethylocta-2,6-dien-1-yl]-4-hydroxy-2-{[(3S,4R,5S,6S)-4,5,6-trihydroxyoxan-3-yl]methoxy}benzoic acid; 3-[(2E)-3,7-dimethylocta-2,6-dien-1-yl]-6-hexyl-4-hydroxy-2-{[(3S,4R,5S,6S)-4,5,6-trihydroxyoxan-3-yl]methoxy}benzoic acid; 3-[(2E)-3,7-dimethylocta-2,6-dien-1-yl]-4-hydroxy-6-(3-methylpentyl)-2-{[(3S,4R,5S,6S)-4,5,6-trihydroxyoxan-3-yl]methoxy}benzoic acid; 3-[(2E)-3,7-dimethylocta-2,6-dien-1-yl]-4-hydroxy-6-(pent-4-en-1-yl)-2-{[(3S,4R,5S,6S)-4,5,6-trihydroxyoxan-3-yl]methoxy}benzoic acid; 3-[(2E)-3,7-dimethylocta-2,6-dien-1-yl]-6-(hex-5-yn-1-yl)-4-hydroxy-2-{[(3S,4R,5S,6S)-4,5,6-trihydroxyoxan-3-yl] methoxy}benzoic acid; 3-[(2E)-3,7-dimethylocta-2,6-dien-1-yl]-6-propyl-4-{[(3R,4R,5S,6S)-4,5,6-trihydroxy-3-(hydroxymethyl) oxan-2-yl]oxy}-2-{[(3S,4R,5S,6S)-4,5,6-trihydroxyoxan-3-yl]methoxy}benzoic acid; 3-[(2E)-3,7-dimethylocta-2,6-dien-1-yl]-6-pentyl-4-{[(3R,4R,5S,6S)-4,5,6-trihydroxy-3-(hydroxymethyl) oxan-2-yl]oxy}-2-{[(3S,4R,5S,6S)-4,5,6-trihydroxyoxan-3-yl]methoxy}benzoic acid; 6-butyl-3-[(2E)-3,7-dimethylocta-2,6-dien-1-yl]-4-{[(3R,4R,5S,6S)-4,5,6-trihydroxy-3-(hydroxymethyl) oxan-2-yl]oxy}-2-{[(3S,4R,5S,6S)-4,5,6-trihydroxyoxan-3-yl] methoxy}benzoic acid; 3-[(2E)-3,7-dimethylocta-2,6-dien-1-yl]-6-hexyl-4-{[(3R,4R,5S,6S)-4,5,6-trihydroxy-3-(hydroxymethyl) oxan-2-yl]oxy}-2-{[(3S,4R,5S,6S)-4,5,6-trihydroxyoxan-3-yl]methoxy}benzoic acid; 3-[(2E)-3,7-dimethylocta-2,6-dien-1-yl]-6-(3-methylpentyl)-4-{[(3R,4R,5S,6S)-4,5,6-trihydroxy-3-(hydroxymethyl) oxan-2-yl] oxy}-2-{[(3S,4R,5S,6S)-4,5,6-trihydroxyoxan-3-yl] methoxy}benzoic acid; 3-[(2E)-3,7-dimethylocta-2,6-dien-1-yl]-6-(pent-4-en-1-yl)-4-{[(3R,4R,5S,6S)-4,5,6-trihydroxy-3-(hydroxymethyl) oxan-2-yl]oxy}-2-{[(3S,4R,5S,6S)-4,5,6-trihydroxyoxan-3-yl]methoxy}benzoic acid; and 3-[(2E)-3,7-dimethylocta-2,6-dien-1-yl]-6-(hex-5-yn-1-yl)-4-{[(3R,4R,5S,6S)-4,5,6-trihydroxy-3-(hydroxymethyl) oxan-2-yl]oxy}-2-{[(3S,4R,5S,6S)-4,5,6-trihydroxyoxan-3-yl]methoxy}benzoic acid, and wherein the compound of Formula (I) is preferably selected from the group consisting of 3-[(2E)-3,7-dimethylocta-2,6-dien-1-yl]-2,4-dihydroxy-6-pentylbenzoic acid, 6-butyl-3-[(2E)-3,7-dimethylocta-2,6-dien-1-yl]-2,4-dihydroxybenzoic acid, 3-[(2E)-3,7-dimethylocta-2,6-dien-1-yl]-6-hexyl-2,4-dihydroxybenzoic acid, 3-[(2E)-3,7-dimethylocta-2,6-dien-1-yl]-2,4-dihydroxy-6-(3-methylpentyl)benzoic acid, 3-[(2E)-3,7-dimethylocta-2,6-dien-1-yl]-2,4-dihydroxy-6-(pent-4-en-1-yl)benzoic acid, 3-[(2E)-3,7-dimethylocta-2,6-dien-1-yl]-6-(hex-5-yn-1-yl)-2,4-dihydroxybenzoic acid.

[19] The process according to any of [1] to [17], wherein the compound of Formula (II) is selected from the group consisting of 2,4-dihydroxy-6-propylbenzoic acid; olivetolic acid (OA); 2-butyl-4-hydroxy-6-methylbenzoic acid; 2-hexyl-4-hydroxy-6-methylbenzoic acid; 4-hydroxy-2-methyl-6-(3-methylpentyl)benzoic acid; 4-hydroxy-2-methyl-6-(pent-4-en-1-yl)benzoic acid; 2-(hex-5-yn-1-yl)-4-hydroxy-6-methylbenzoic acid; 2-hydroxy-6-propyl-4-{[(3R,4R,5S,6S)-4,5,6-trihydroxy-3-(hydroxymethyl) oxan-2-yl]oxy}benzoic acid; 2-hydroxy-6-pentyl-4-{[(3R,4R,5S,6S)-4,5,6-trihydroxy-3-(hydroxymethyl) oxan-2-yl] oxy}benzoic acid; 2-butyl-6-hydroxy-4-{[(3R,4R,5S,6S)-4,5,6-trihydroxy-3-(hydroxymethyl) oxan-2-yl]oxy}benzoic acid; 2-hexyl-6-hydroxy-4-{[(3R,4R,5S,6S)-4,5,6-trihydroxy-3-(hydroxymethyl) oxan-2-yl]oxy}benzoic acid; 2-hydroxy-6-(3-methylpentyl)-4-{[(3R,4R,5S,6S)-4,5,6-trihydroxy-3-(hydroxymethyl) oxan-2-yl]oxy}benzoic acid; 2-hydroxy-6-(pent-4-en-1-yl)-4-{[(3R,4R,5S,6S)-4,5,6-trihydroxy-3-(hydroxymethyl) oxan-2-yl]oxy}benzoic acid; 2-(hex-5-yn-1-yl)-6-hydroxy-4-{[(3R,4R,5S,6S)-4,5,6-trihydroxy-3-(hydroxymethyl) oxan-2-yl]oxy}benzoic acid; 4-hydroxy-2-propyl-6-{[(3R,4R,5S,6S)-4,5,6-trihydroxy-3-(hydroxymethyl) oxan-2-yl]oxy}benzoic acid; 4-hydroxy-2-pentyl-6-{[(3R,4R,5S,6S)-4,5,6-trihydroxy-3-(hydroxymethyl) oxan-2-yl]oxy}benzoic acid; 2-butyl-4-hydroxy-6-{[(3R,4R,5S,6S)-4,5,6-trihydroxy-3-(hydroxymethyl) oxan-2-yl]oxy}benzoic acid; 2-hexyl-4-hydroxy-6-{[(3R,4R,5S, 6S)-4,5,6-trihydroxy-3-(hydroxymethyl) oxan-2-yl] oxy}benzoic acid; 4-hydroxy-2-(3-methylpentyl)-6-{[(3R, 4R,5S,6S)-4,5,6-trihydroxy-3-(hydroxymethyl) oxan-2-yl] oxy}benzoic acid; 4-hydroxy-2-(pent-4-en-1-yl)-6-{[(3R, 4R,5S,6S)-4,5,6-trihydroxy-3-(hydroxymethyl) oxan-2-yl] oxy}benzoic acid; 2-(hex-5-yn-1-yl)-4-hydroxy-6-{[(3R, 4R,5S,6S)-4,5,6-trihydroxy-3-(hydroxymethyl) oxan-2-yl] oxy}benzoic acid; 2-propyl-4,6-bis({[(3R,4R,5S,6S)-4,5,6-trihydroxy-3-(hydroxymethyl) oxan-2-yl]oxy})benzoic acid; 2-pentyl-4,6-bis({[(3R,4R,5S,6S)-4,5,6-trihydroxy-3-(hydroxymethyl) oxan-2-yl]oxy})benzoic acid; 2-butyl-4,6-bis({[(3R,4R,5S,6S)-4,5,6-trihydroxy-3-(hydroxymethyl) oxan-2-yl]oxy})benzoic acid; 2-hexyl-4,6-bis({[(3R,4R,5S, 6S)-4,5,6-trihydroxy-3-(hydroxymethyl) oxan-2-yl]oxy}) benzoic acid; 2-(3-methylpentyl)-4,6-bis({[(3R,4R,5S,6S)-4,5,6-trihydroxy-3-(hydroxymethyl) oxan-2-yl]oxy}) benzoic acid; 2-(pent-4-en-1-yl)-4,6-bis({[(3R,4R,5S,6S)-4, 5,6-trihydroxy-3-(hydroxymethyl) oxan-2-yl]oxy})benzoic acid; and 2-(hex-5-yn-1-yl)-4,6-bis({[(3R,4R,5S,6S)-4,5,6-trihydroxy-3-(hydroxymethyl) oxan-2-yl]oxy})benzoic acid, and wherein the compound of Formula (II) is preferably selected from the group consisting of 2,4-dihydroxy-6-pentylbenzoic acid, 2-butyl-4,6-dihydroxybenzoic acid, 2-hexyl-4,6-dihydroxybenzoic acid, 2,4-dihydroxy-6-(3-methylpentyl)benzoic acid, 2,4-dihydroxy-6-(pent-4-en-1-yl)benzoic acid, 2-(hex-5-yn-1-yl)-4,6-dihydroxybenzoic acid.

[20] The process according to any of [1] to [17], wherein the compound of Formula (I) is cannabigerolic acid (CBGA), the compound of Formula (II) is olivetolic acid (OA), the compound of Formula (IV) is delta-9-tetrahydrocannabinolic acid (THCA), the compound of Formula (V) is cannabichromenic acid (CBCA), the compound of Formula (VI) is cannabidiolic acid (CBDA), the compound of Formula (VII) is tetrahydrocannabinol (THC), the compound of Formula (VIII) is cannabichromene (CBC), and the compound of Formula (IX) is cannabidiol (CBD).

In the context of the present invention, it is preferred that $R^2$ be —C(O)OH, $R^3$ be —OH and $R^4$ be —OH while for $R^1$ the definitions provided herein above apply. Preferably, $R^1$ is selected from linear or branched $C_{4-6}$ alkyl, linear or branched $C_{4-6}$ alkenyl and linear or branched $C_{4-6}$ alkynyl. Accordingly, in the context of the present invention, the above disclosed list of items preferably may read as follows:

[1] A process for the production of a compound of Formula (I')

Formula (I')

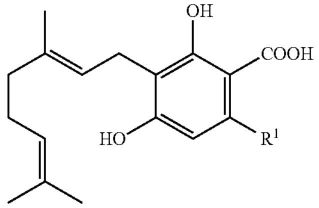

wherein $R^1$ is selected from linear or branched $C_{4-6}$ alkyl, linear or branched $C_{4-6}$ alkenyl and linear or branched $C_{4-6}$ alkynyl, wherein the process comprises the step of reacting a plant extract having prenyltransferase activity with a compound of Formula (II')

Formula (II')

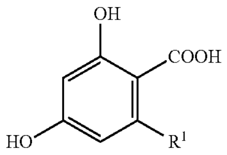

wherein $R^1$ is selected from linear or branched $C_{4-6}$ alkyl, linear or branched $C_{4-6}$ alkenyl and linear or branched $C_{4-6}$ alkynyl, and geranyl pyrophosphate (GPP) having the following Formula (III')

Formula (III')

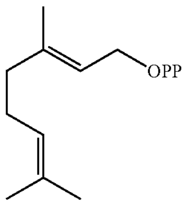

wherein PP represents pyrophosphate, to produce the compound of Formula (I'), wherein the plant extract is not a *Cannabis sativa, Acmella oleracea, Echinaceae* angustifolia, *Echinaceae purpurea, Helichrysum umbraculigerum, Heliopsis helianthoides, Piper nigrum, Radula marginata*, and/or *Radula perrottetii* plant extract.

[2] A process for the production of a compound of the following Formula (IV')

Formula (IV')

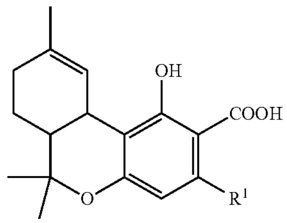

wherein $R^1$ is selected from linear or branched $C_{4-6}$ alkyl, linear or branched $C_{4-6}$ alkenyl and linear or branched $C_{4-6}$ alkynyl, wherein the process comprises producing a compound of Formula (I') by the process of [1] and converting the compound of Formula (I') to the compound of Formula (IV') in the presence of the tetrahydrocannabinolic acid synthase (THCAS; EC 1.21.3.7).

[3] The process of [2], wherein the compound of Formula (IV') is decarboxylated to a compound of Formula (VII')

Formula (VII')

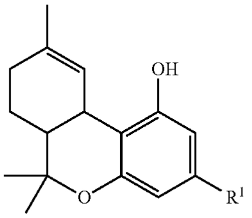

wherein $R^1$ is selected from linear or branched $C_{4-6}$ alkyl, linear or branched $C_{4-6}$ alkenyl and linear or branched $C_{4-6}$ alkynyl.

[4] A process for the production of a compound of Formula (V')

Formula (V')

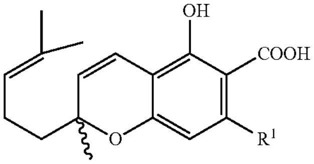

wherein $R^1$ is selected from linear or branched $C_{4-6}$ alkyl, linear or branched $C_{4-6}$ alkenyl and linear or branched $C_{4-6}$ alkynyl, wherein the process comprises producing a compound of Formula (I') by the process of [1] and converting the compound of Formula (I') to a compound of Formula (V') in the presence of the THCAS (EC 1.21.3.7), cannabidiolic acid synthase (CBDAS; EC 1.21.3.8) and/or cannabichromenic acid synthase (CBCAS; EC 1.3.3.-).

[5] The process of [4], wherein the compound of Formula (V') is decarboxylated to a compound of Formula (VIII')

Formula (VIII')

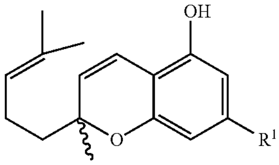

wherein $R^1$ is selected from linear or branched $C_{4-6}$ alkyl, linear or branched $C_{4-6}$ alkenyl and linear or branched $C_{4-6}$ alkynyl.

[6] A process for the production of a compound of Formula (VI')

Formula (VI')

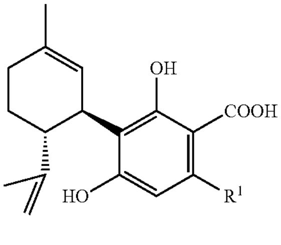

wherein $R^1$ is selected from linear or branched $C_{4-6}$ alkyl, linear or branched $C_{4-6}$ alkenyl and linear or branched $C_{4-6}$ alkynyl, wherein the process comprises producing a compound of Formula (I') by the process of claim [1] and converting the compound of Formula (I') to a compound of Formula (VI') in the presence of the CBDAS (EC 1.21.3.8).

[7] The process of [6], wherein the compound of Formula (VI') is decarboxylated to a compound of Formula (IX')

Formula (IX')

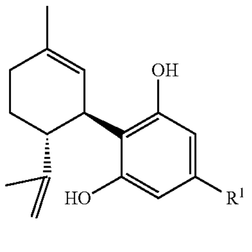

wherein $R^1$ is selected from linear or branched $C_{4-6}$ alkyl, linear or branched $C_{4-6}$ alkenyl and linear or branched $C_{4-6}$ alkynyl.

[8] The process of any one of [1] to [7], wherein the plant extract is obtained from a plant which expresses an endogenous prenyltransferase.

[9] The process of [8], wherein the plant is a genetically modified plant expressing a heterologous THCAS (EC 1.21.3.7), CBDAS (EC 1.21.3.8) and/or CBCAS (EC 1.3.3.-).

[10] The process of any one of [1] to [9], wherein the plant extract is obtained from solid plant material with an extraction agent to obtain an extraction liquid containing the plant extract dissolved in said extraction liquid.

[11] The process of [10], wherein the extraction agent is an aqueous buffer selected from the group of TAPS, Bicine, Tricine, TAPSO, HEPES, TES, MOPS, PIPES, Cacodylate, MES, $Na_2HPO_4$, $NaH_2PO_4$, CHES, Acetic acid, Citric acid, Borate and $KH_2PO_4$.

[12] The process of any one of [1] to [9], wherein the plant extract is a liquid cell culture.

[13] The process of any one of [1] to [12], wherein the plant extract is obtained from a plant selected from the group consisting of *Lactuca sativa, Nepeta cataria, Nicotiana benthamiana, Nicotiana tabacum* and *Ocimum basilicum.*

[14] The process according to any of [1] to [13], wherein $R^1$ is selected from linear or branched $C_{4-6}$ alkyl, linear $C_{4-6}$ alkenyl and linear $C_{4-6}$ alkynyl, wherein the linear $C_{4-6}$ alkenyl contains not more than one C=C double bond, which is preferably a terminal C=C double bond, and the linear $C_{4-6}$ alkynyl contains not more than one C≡C triple bond, which is preferably a terminal C≡C triple bond, preferably, wherein $R^1$ is selected from n-pentyl, n-butyl, n-hexyl, 3-methylpentyl, 4-pentenyl and 5-hexynyl, more preferably, wherein $R^1$ is n-pentyl.

[15] The process according to any of [1] to [14], wherein the compound of Formula (I') is cannabigerolic acid (CBGA), the compound of Formula (II') is olivetolic acid (OA), the compound of Formula (IV') is delta-9-tetrahydrocannabinolic acid (THCA), the compound of Formula (V') is cannabichromenic acid (CBCA), the compound of Formula (VI') is cannabidiolic acid (CBDA), the compound of Formula (VII') is tetrahydrocannabinol (THC), the compound of Formula (VIII') is cannabichromene (CBC), and the compound of Formula (IX') is cannabidiol (CBD).

What is exemplarily shown for $R^1$, can be applied to the other residues as defined herein above.

BRIEF DESCRIPTION OF THE DRAWING FIGURES

The present invention is further described by reference to the following non-limiting figures and examples.

The Figures show:

FIG. 1: Schematic depiction of the cannabinoid biosynthesis pathway in *Cannabis sativa* (modified according to Zirpel et al., J Biotechnol. (2017), 259:204-212). In general, the pathway can be separated into the geranyl pyrophosphate (GPP) producing part deriving from the 2-C-methyl-D-erythritol-4-phosphate (MEP) pathway, the olivetolic acid (OA) producing part (starting from fatty acid synthesis) and the actual cannabinoid producing part. Hexanoic acid originating from the fatty acid metabolism is first converted to the active CoA thioester (hexanoyl-CoA) by the acyl-activating enzyme 1 (AAE1). OA is then formed from three molecules of malonyl-CoA and one molecule of hexanoyl-CoA by aldol condensation, catalyzed by the enzymes olivetol synthase (OLS) and olivetolic acid cyclase (OAC). Subsequently, the alkylation of OA with GPP is catalyzed by cannabigerolic acid synthase (CBGAS), forming cannabigerolic acid (CBGA), which is the direct precursor of cannabinoids. Delta-9-tetrahydrocannabinolic acid (THCA), cannabichromenic acid (CBCA) and cannabidiolic acid (CBDA) are then produced by the oxidocyclases delta-9-tetrahydrocannabinolic acid synthase (THCAS) and cannabichromenic acid synthase (CBCAS), respectively. Finally, the aforementioned acids are non-enzymatically decarboxylated to THC, CBC and CBD.

Figure 2:
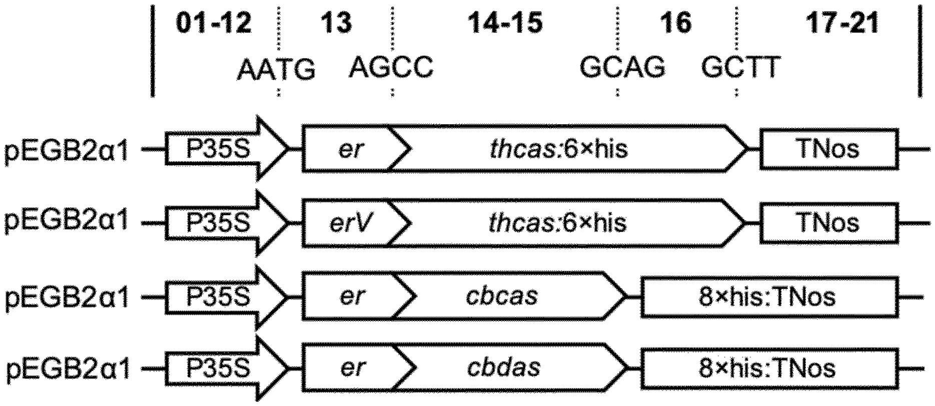

FIG. 2: Schematic representation of the generated expression constructs utilizing the GoldenBraid cloning technique. The capital letters show the four-nucleotide overhangs ensuring correct final orientation within the transcriptional unit (TU), while the numbers above the scheme represent standard GoldenBraid classes within the TU structure (Sarrion-Perdigones et al., 2013, Plant Physiol. 162 (3): 1618-1631). P35S, cauliflower mosaic virus (CaMV) 35S promoter. TNos, nopaline synthase terminator. Er, ER signal peptide. ErV, vacuolar target peptide. Arrows not drawn to scale.

Figure 3:
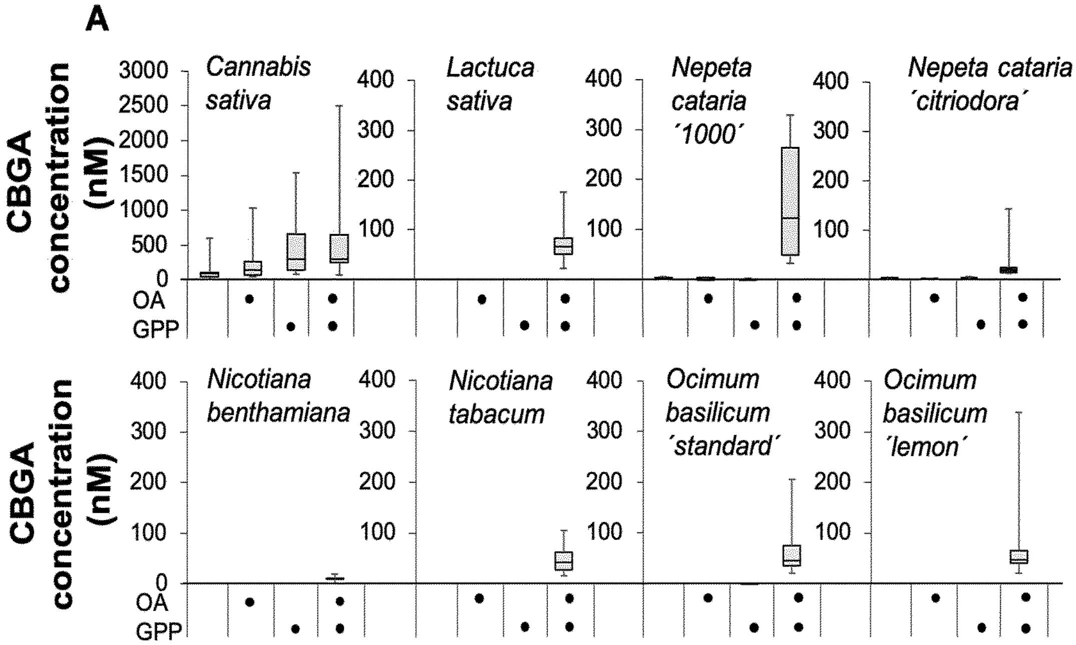
Figure 3:
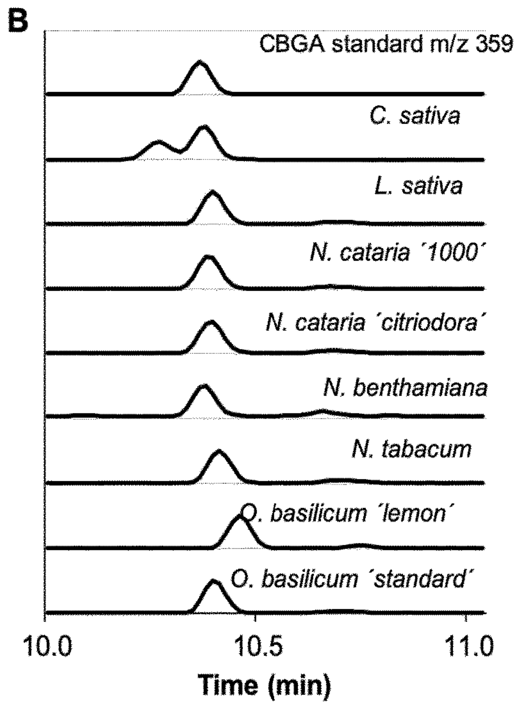

FIG. 3: Cannabigerolic acid (CBGA) production in total soluble protein (TSP) extracts. (A) CBGA yields from TSP extracts of the indicated wild-type plant species were determined after prenyltransferase activity assays were performed, in which either both, one or none of the two substrates olivetolic acid (OA) and geranyl pyrophosphate (GPP) were deficient. (B) shows selected ion monitoring (SIM) chromatograms with selected m/z of m/z 359 (CBGA) of the obtained assay products and CBGA standard. Normalized HPLC-MS analysis N=1, n=9.

Figure 4:
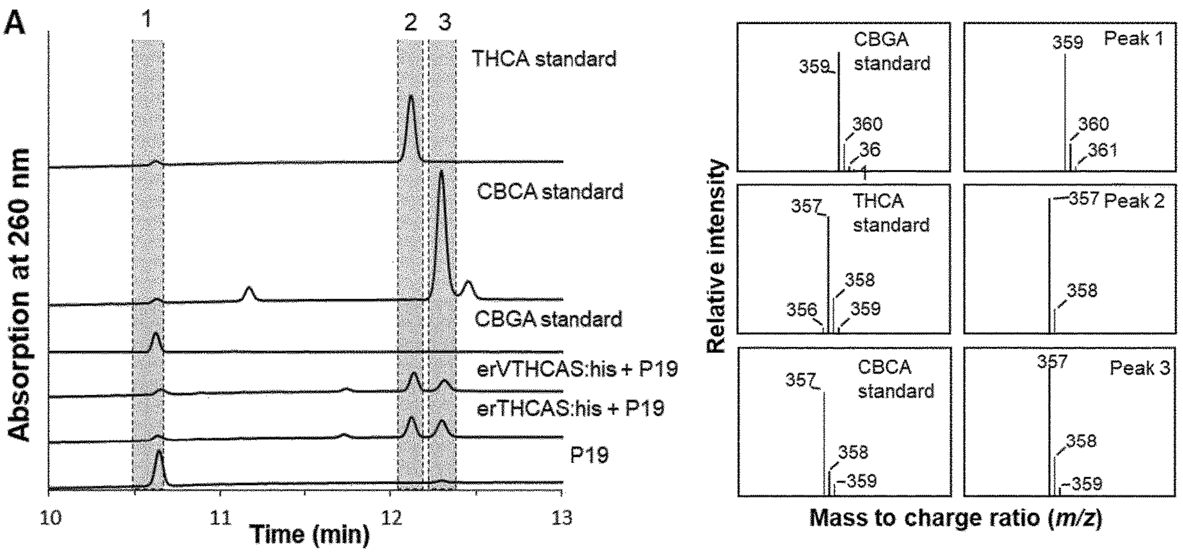
Figure 4:
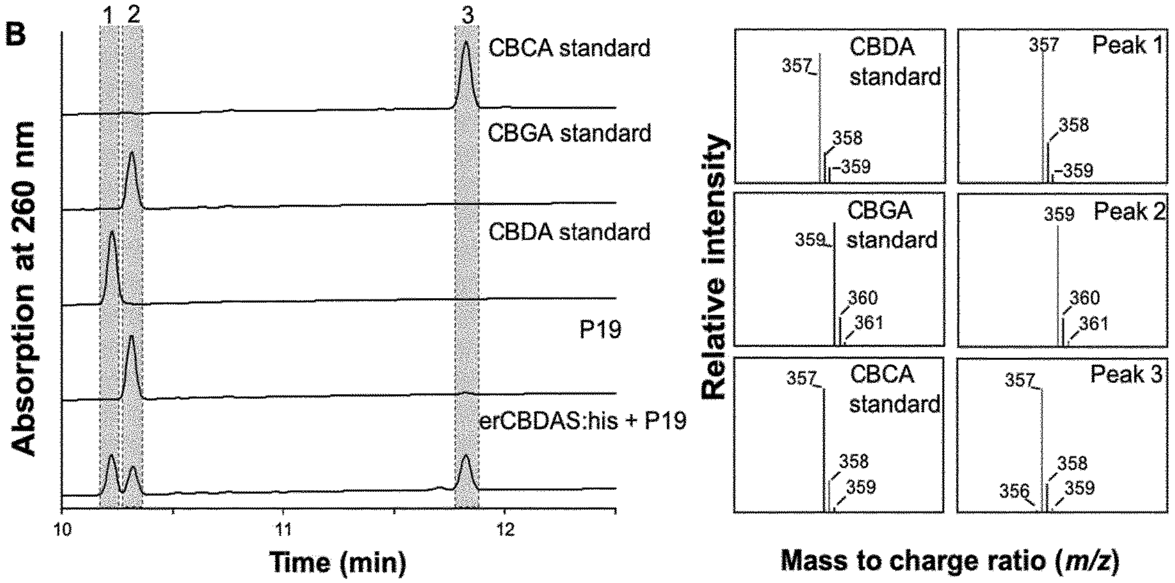
Figure 4:
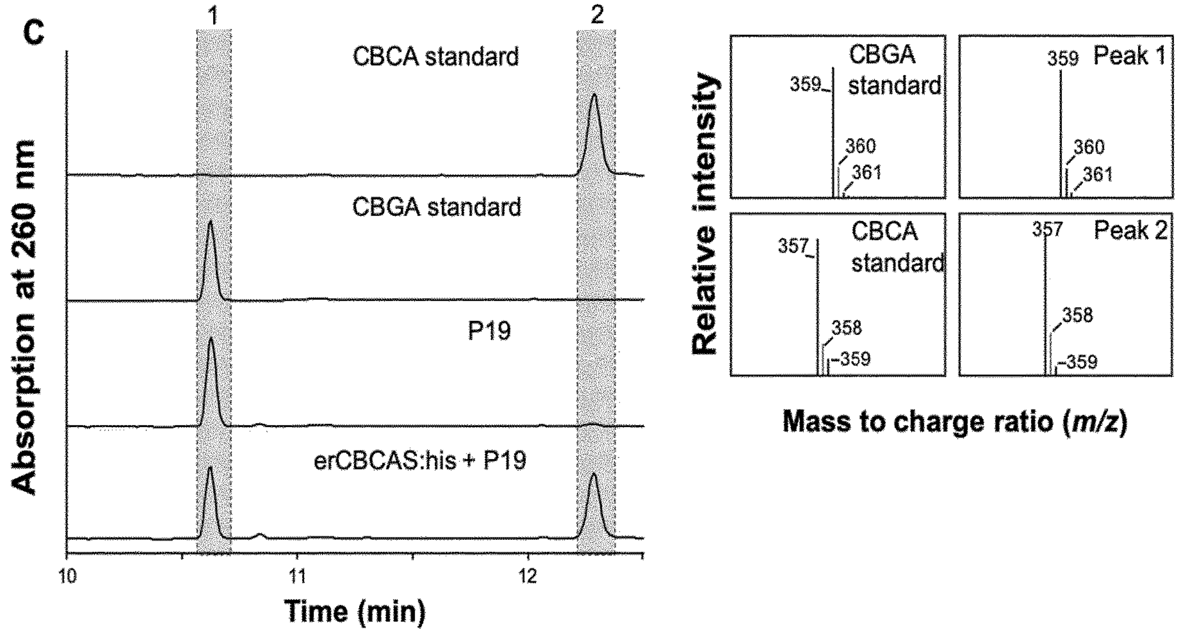

FIG. 4: Production of delta-9-tetrahydrocannabinolic acid (THCA), cannabichromenic acid (CBCA) and cannabidiolic acid (CBDA) from plant extracts of *N. benthamiana* plants transiently transformed with er:THCAS and P19, erV:THCAS and P19, er:CBDAS and P19, or er:CBCAS and P19. (A) reports the production of THCA and CBCA by er:THCAS and erV:THCAS in *N. benthamiana* detected by HPLC-MS. Peaks (1-3) correspond to references (left panel) with given reference fragmentation (right panel). (B) reports the production of CBCA and CBDA by cannabidiolic acid synthase (CBDAS) with ER/apoplast targeting (er:CBDAS) in *N. benthamiana* detected by HPLC-MS. Peaks (1-3) correspond to references (left panel) with given reference fragmentation (right panel). (C) shows production of CBCA by cannabichromenic acid synthase (CBCAS) with ER/apoplast targeting (er:CBCAS) in *N. benthamiana* detected by HPLC-MS. Peaks (1-3) correspond to references (left panel) with given reference fragmentation (right panel).

Figure 5:
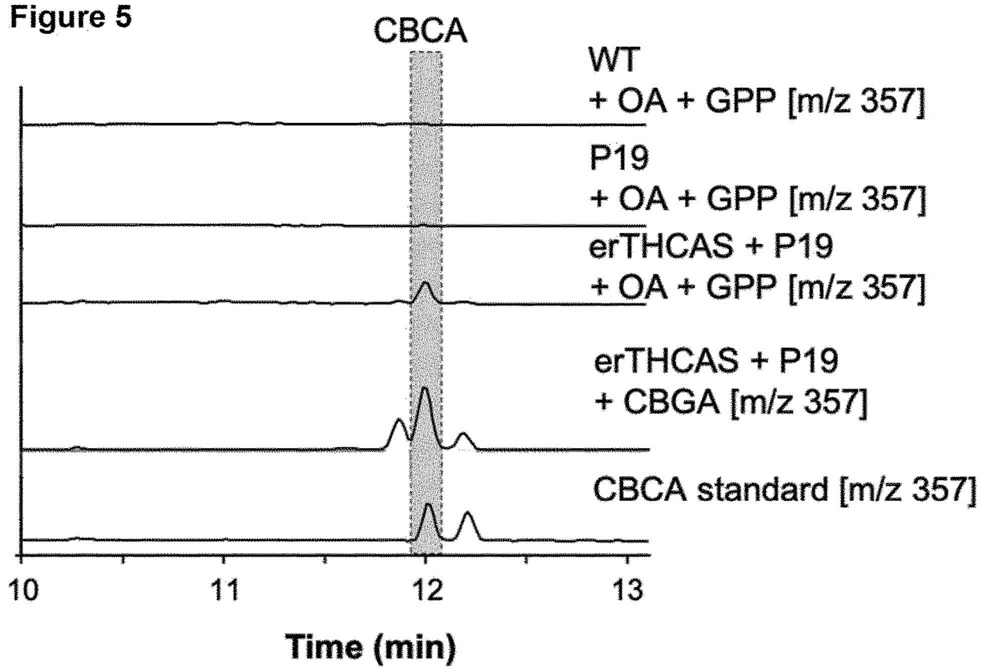
Figure 6:
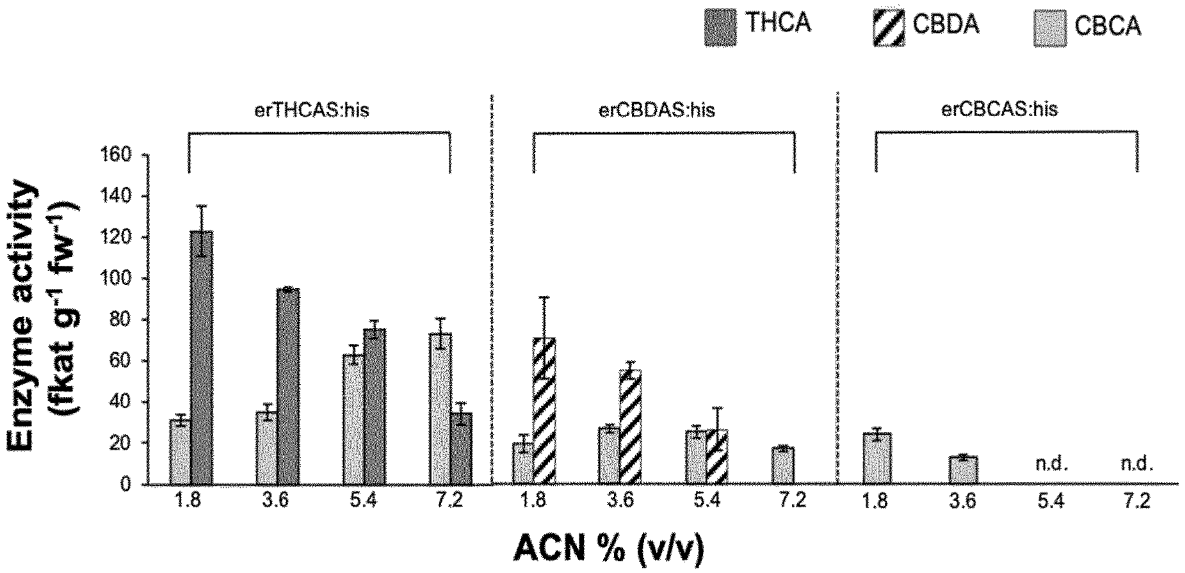

FIG. 5: Production of cannabichromenic acid (CBCA) from leaf extracts of transiently transformed *N. benthamiana* plants. FIG. 5 reports the HPLC-MS analysis of total soluble protein extracts supplemented with OA and GPP or CBGA of *N. benthamiana* plants transiently transformed with plasmids harboring the genetic information for the tetrahydrocannabinolic acid synthase (THCAS) with ER/apoplast targeting (er:THCAS) and for the P19 suppressor of gene silencing (p19). As controls, wildtype (WT) plants or plants solely transformed with P19 were used. Screening for CBCA was performed in negative SIM mode for an m/z of 357. Endogenously produced CBGA can serve as substrate for heterologous produced tetrahydrocannabinolic acid synthase (THCAS).

FIG. 6: In vitro assays with crude extracts of transiently transformed *N. benthamiana* plants with addition of various amounts of acetonitrile. For quantification of er:THCAS, er:CBDAS and er:CBCAS enzyme activity, the amount of formed product was quantified by peak integration at the wavelength of 260 nm and subsequent conversion from area counts into fkat $$g_{FW}^{-1}$$

by means of serial standard dilutions (THCA 800 nM-0.05 mM; CBDA 800 nM-0.05 mM; CBCA 6.0 nM-0.05 mM).

Figure 7:
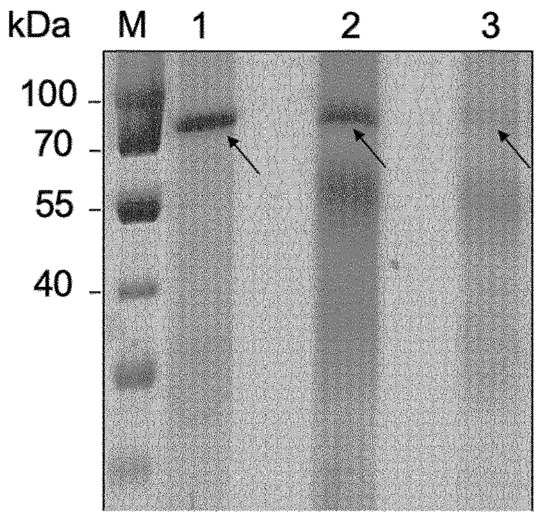

FIG. 7: Detection of er:THCAS, er:CBDAS and er:CBCAS produced in transiently transformed *N. benthamiana* plants. FIG. 7 shows SDS-PAGE of purified er:THCAS (1), er:CBDAS (2) and er:CBCAS (3) visualized by silver nitrate staining. Arrows indicate the desired proteins with the expected size of approximately 80 kDA. Numbers to the left indicate molecular mass of marker proteins (M).

FIG. 8: Detection of enzyme activity of purified er:THCAS, er:CBDAS and er:CBCAS produced in transiently transformed *N. benthamiana* plants. FIG. 8 (A) shows in vitro assays of purified er:THCAS with addition of different solvents. Enzyme activity was measured towards production of THCA (upper panel) and CBCA (lower panel). (B) shows in vitro assays of purified er:CBDAS with addition of different solvents. Enzyme activity was measured towards production of CBDA (upper panel) and CBCA (lower panel). (C) shows in vitro assays of purified er:CBCAS with addition of different solvents. Enzyme activity was measured towards production of CBCA. THCA, CBCA and CBDA were quantified by HPLC-MS through peak integration at the wavelength of 260 nm and subsequent conversion from area counts into pkat $mg^{-1}$ purified protein by means of serial dilutions of each cannabinoid.

FIG. 9: Evaluation of prenyltransferase activity in samples obtained by ultracentrifugation at 38,000×g. The assays were performed with total soluble proteins (TSP) from wild-type (WT) *N. benthamiana* plants in which either none or one of the two substrates olivetolic acid (OA) and geranyl pyrophosphate (GPP) were deficient. Additionally, the pellet obtained after centrifugation was resolved in buffer and also subjected to prenyltransferase activity assays. The products were analyzed in selected ion monitoring (SIM) mode with selected m/z of 359 (CBGA) of the obtained assay products and CBGA standard.

EXAMPLES

The following Examples illustrate the invention:

Example 1 Cloning of Tetrahydrocannabinolic Acid Synthase (THCAS), Cannabidiolic Acid Synthase (CBDAS) and Cannabichromenic Acid Synthase (CBCAS) and Generation of *A. tumefaciens* EHA105

Plasmids and Nucleic Acid Sequences:

The basic GoldenBraid (GB) parts, encompassing the pUPD harboring cauliflower mosaic virus (CaMV) 35S promoter (P35S, GB0030), the pUPD containing nopaline synthase terminator (TNos, GB0037) and the pDGB2α1, have been described previously (Sarrion-Perdigones et al., Plant Physiol. (2013), 162 (3): 1618-1631). Moreover, the pBIN61 plasmid harboring the P19 suppressor of gene silencing has been disclosed in Lakatos et al., Embo J. (2004), 23:876-884. The signaling peptide sequence of calreticulin (er) from *Nicotiana* sp. (GenBank accession XM_009806292, version XM_009806292.1, SEQ ID NO: 4) derived from pICH17620 plasmid (ICONGenetics, Halle, Germany), while vacuolar target peptide sequence (erV) of strictosidine synthase derived from *Rauvolfia serpentina* (GenBank accession X62334, version X62334.1, SEQ ID NO: 5).

For introduction of the thcas:6× his without the first 84 bp (native signal peptide) into the GoldenBraid (GB) system, the pET15b (+) plasmid (Merck Millipore, Burlington, MA, USA, Cat. no. 69661) harboring the coding sequence of native THCAS (GenBank accession AB057805, version AB057805.1, SEQ ID NO: 1) was used. Therefore, the thcas:6× his was amplified by PCR using the primer pair (pTHCAS fw, 5'-GCG CCG TCT CAC TCG AGC CAA TCC TCG AGA AAA CT-3' (SEQ ID NO: 6) and pTHCAS: his rev, 5'-GCG CCG TCT CGC TCG AAG CTT AGT GAT GGT GAT GAT GAT G CG GTG GAA GAG GTG GG ATA C-3' (SEQ ID NO: 7)) directed against THCAS from *Cannabis sativa*, ascertaining addition of BsmBI recognition sites and appropriate fusion overhangs (AGCC at the 5'-end and GCTT at the 3'-end of THCAS). thcas:6× his sequence without the first 84 bp, containing the appropriate overhangs for cloning into pUPD is shown in SEQ ID NO: 8). For introduction of cbdas (GenBank accession no: AB292682, version no: AB292682.1, SEQ ID NO: 2) and cbcas (sequence as published in WO 2015/196275 A1 under SEQ ID NO: 5, SEQ ID NO: 3) without the native signal peptide, synthetic genes with BsmBI recognition sites and the appropriate fusion overhangs (AGCC at the 5'-end and GCAG at the 3'-end of both enzymes) were purchased from GenScript (Piscataway Township, NJ, USA) and used for GoldenBraid (GB) reactions. Cbdas sequence without the first 84 bp, containing the appropriate overhangs for cloning into pUPD is shown in SEQ ID NO: 9. Cbcas sequence without the first 84 bp, containing the appropriate overhangs for cloning into pUPD is shown in SEQ ID NO: 10.

Molecular Cloning Using Golden Braid Assembly

The GB assemblies were then performed as described by Sarrion-Perdigones et al., Plant Physiol. (2013), 162 (3): 1618-1631). In case of new domestications, the 10 μL of the GB reaction mixtures contained 75 ng of PCR products or synthesized DNA (thcas:6× his, cbdas, cbcas), 75 ng of the pUPD vector, 1× ligase buffer (Promega, Madison, Wisconsin, USA), 1 mM DTT (Carl Roth, Karlsruhe, Germany), 1 μL (3 u/μL) of T4 DNA ligase (Promega, Madison, Wisconsin, USA) and 1 μL (10 u/μL) of BsmBI (Thermo Fisher Scientific, Waltham, USA). In case of the assembly of transcriptional units, 75 ng of pUPDs harboring relevant DNA parts (P35S, er, erV, thcas:6× his, cbdas, cbcas, TNos and 8× his: TNos), 75 ng of the pDGB2α1 destination vector, 1× ligase buffer (Promega, Madison, Wisconsin, USA), 1 mM DTT (Carl Roth, Karlsruhe, Germany), 1 μL (3 u/μL) of T4 DNA ligase and 1 μL (10 u/L) of BsaI (New England Biolabs, Ipswich, MA, USA) were used for the reaction setup. The GB assemblies were performed in 25- or 50-cycle digestion and ligation reactions for 2 min at 37° C. and 5 min at 16° C., respectively. Afterwards, the reaction mixtures were transformed into chemically competent *E. coli* TOP10 cells (Thermo Fisher Scientific, Waltham, USA). Positive clones were selected on LB agar plates containing ampicillin (100 μg/mL) and kanamycin (50 μg/mL) as well as 40 μg/mL of 5-bromo-4-chloro-3-indolyl-β-D-galactopyranoside (X-Gal, VWR International GmbH, Darmstadt, DE, Cat. no. A1007.0001) for blue/white selection. Subsequently, positive clones were grown in liquid LB (Bertani et al., J Bacteriol. (1951), 62:293-300.), supplemented with supplemented with ampicillin (100 μg/mL) and kanamycin (50 μg/mL) under constant agitation (170 rpm) at 37° C. and 28° C., respectively. Plasmid DNA was extracted by means of the E.Z.N.A. Plasmid Mini Kit I (VWR International GmbH, Cat. no. D6942). The assemblies were verified by restriction analysis with EcoRI. The newly domesticated THCAS sequence were sequenced by Eurofins Genomics using M13 primers: M13 uni (−21), 5'-TGT AAA ACG ACG GCC AGT-3' (SEQ ID NO: 11) and M13 rev (−29), 5'-CAG GAA ACA GCT ATG ACC-3' (SEQ ID NO: 12). Finally, the desired α-level GB construct was transformed into chemically competent *Agrobacterium tumefaciens* EHA105 cells (ICON Genetics, Halle, Germany). EHA105 were cultivated in lysogeny broth (LB; Bertani et al., J Bacteriol. (1951), 62:293-300) supplemented with ampicillin (100 μg/mL), kanamycin (50 μg/mL), rifampicin (50 μg/mL) and 100 UM 3,5-dimethoxy-4-hydroxyacetophenone (acetosyringone, Sigma-Aldrich, St. Louis, MO, USA, Cat. no. D134406) under constant agitation (170 rpm) at 37° C. and 28° C. The transfer was confirmed by colony PCR using primer pairs (p35S-Cf3,5'-CCA CGT CTT CAA AGC AAG TGG-3' (SEQ ID NO: 13) and p35S-Cr4,5'-TCC TCT CCA AAT GAA ATG AAC TTC C-3' (SEQ ID NO: 14)) screening for the cauliflower mosaic virus 35S promoter (P35S). A scheme of the generated expression constructs is shown in FIG. 2.

Example 2 Transient Transformation of *Nicotiana benthamiana* Plants

Greenhouse-grown *N. benthamiana* plants (cultivated at 21±2° C. under 70% humidity and 16 h of illumination) were used for *Agrobacterium*-mediated transient transformation. Therefore, *A. tumefaciens* EHA105 cells harboring the appropriate expression construct as shown in the schematic representation of Example 1 and *A. tumefaciens* EHA105 harboring the P19 suppressor gene were utilized for co-infiltration. EHA105 cells carrying pBIN61-P19 were used as negative controls. Overnight cultures of *A. tumefaciens* EHA105 cells were centrifuged at 1,500×g for 5 min and the obtained cell pellet was resuspended in infiltration buffer (10 mM MES, 10 mM $MgSO_4$, 100 UM acetosyringone, pH 5.5) to a final $OD_{600}$ of 0.7. After an incubation period of 2 h at 28° C., the bacterial suspensions were infiltrated into the abaxial side of leaves of four-week-old plants using a syringe without a needle. When co-infiltrated, the individual *Agrobacterium* suspensions were mixed in equal ratios to keep the concentration of all relevant constructs constant within each experiment. After infiltration, the plants were incubated for 5-7 days at 21±2° C. in a climatic chamber under 60% humidity and 12/12 h day/night cycle. Infiltrations were performed in five biological replicates.

Example 3 Endogenous Prenyltransferase with Activity Towards CGBA Production can be Found in Various Wildtype Plants Olivetolic acid (OA) and geranyl pyrophosphate (GPP) are the natural substrates for the CBGA synthase to build the cannabinoid precursor cannabigerolic acid (CBGA). In the following experiment it was tested whether an endogenous prenyltransferase with activity towards CGBA production can be found in plants i.e. *Cannabis sativa, Lactuca sativa, Nepeta cataria, Nicotiana tabacum, Ocimum basilicum* other than *Nicotiana benthamiana* and whether it is reliant on OA and GPP as substrate. Plant extract of *Cannabis sativa*, a plant that naturally produces cannabinoids, was used as positive control.

Therefore, total soluble protein (TSP) were retrieved from different wildtype plant species by grinding from previously frozen leaf disks (100 mg plant material) in liquid nitrogen. For *N. benthamiana* and *N. tabacum*, the leaf powder was then mixed with 100 μL of CBGAS assay buffer (50 mM Tris/HCl, 10 mM NaCl, pH 7.5) at RT and centrifuged at 17,000×g for 30 min. For *C. sativa, N. cataria, O. basilicum* and *L. sativa*, the leaf powder was then mixed with 150 μL of CBGAS assay buffer (50 mM Tris/HCl, 10 mM NaCl, pH 7.5) at RT and centrifuged at 17,000×g for 30 min. Samples were subjected to prenyltransferase activity assays. Therefore, 87 μL of the prepared TSP samples were mixed with 10 μL (10 mM) geranyl pyrophosphate (GPP, Axon Medchem, Groningen, The Netherlands, Cat. no. Axon 1489), 1 μL (50 mM) olivetolic acid (OA, Santa Cruz Biotechnology, Heidelberg, Germany, Cat. no. sc-484998) and 2 μL (500 mM) $MgCl_2$ (VWR, Cat. no. SAFSM8266). Afterwards, the mixtures were incubated at 30° C. and 750 rpm for 24 h. Control tests were performed in parallel (see table 1). The assays were quenched by adding 275 μL of −20° C. acetonitrile (ACN), followed by incubation on ice for 30 min. Finally, the supernatants were purified two times from solid particles by centrifugation (17,000×g, 30 min, 4° C.).

CBGA was analyzed via HPLC-MS as depicted in FIG. 3. The Figure shows the CBGA yields from TSP extracts of the indicated wild-type plants after prenyltransferase assays were performed. *C. sativa* is the only of the here tested plants that is not reliant on additional OA and GPP within the prenyltransferase assay. The experiment was conducted by using the 1260 Infinity HPLC system (G4225A high performance degasser, G1312B binary pump, G1329B autosampler, G1316C column thermostat, G4212B diode array detector; Agilent, Santa Clara, CA, USA) connected to the 6120 Quadrupole mass spectrometer (Agilent). After the sample injection of 10 μL onto the column (Poroshell 120SB-C18, 3.0×150 mm, 2.7 μm; Agilent) a gradient of the mobile phase consisting of $ddH_2O$/0.1% formic acid (A) and acetonitrile/0.1% formic acid (B) was applied as following (% B): 0-2 min, 20; 2-8 min, 20 to 100; 8-12 min, 100. Subsequently the column was reequilibrated with 20% solvent B for 5 min. The flow rate was set constant to 0.5 mL/min. Cannabinoids were detected at the wavelength of 260 nm. Further investigation was done in negative selected ion monitoring (SIM) with selected m/z of 359. The amount of formed product was quantified by peak integration and subsequent conversion from area counts into nM by means of serial standard dilutions (CBGA 1.6-800 nM). Normalized HPLC-MS analysis N=1, n=9. CBGA standard was purchased from Sigma-Aldrich (Cat. no. C-142). The experiment shows that various wild-type plant species are in possession of their own endogenous prenyltransferases, which are capable of converting OA and GPP into CBGA.

Example 4 Heterologous Produced THCAS, CBDAS and CBCAS Show Overlapping Product Specificity It should be tested whether *N. benthamiana* is capable of producing THCA, CBDA and CBCA by heterologously expressed THCAS, CBDAS and CBCAS, respectively. Therefore, the genes for er:THCAS, erV:THCAS, er:CBDAS or er:CBCAS were introduced into *N. benthamiana* by using GoldenBraid technology and transient transformation as described in Examples 1 and 2. After 5 days post inoculation, 150 mg of frozen plant material was homogenized in 500 μL of THCAS/CBDAS/CBCAS reaction buffer (100 mM trisodium citrate, pH 5.5) at RT and centrifuged (17,000×g, 15 min). Subsequently, the supernatants were incubated with CBGA (final concentration 0.05 mM, 1.8% (v/v) ACN) for 2 h at 37° C. To terminate the reactions, 275 μl of ice-cold acetonitrile were added, followed by incubation on ice for 30 min. Finally, the supernatants were purified two times from solid particles by centrifugation (17,000×g, 30 min, 4° C.). THCA, CBCA and CBDA were then analyzed by using the HPLC-MS method described in Example 3 at the wavelength of 260 nm as well as in the negative electrospray ionization (ESI) mode with a full scan MS experiment (m/z 150-800). Analysis of pro-

TABLE 1

Control reactions.

| | TSP extract | Geranyl pyrophosphate (10 mM) | Olivetolic acid (50 mM) | $MgCl_2$ (500 mM) | Assay buffer | Cannabigerolic acid (2.79 mM) |
|---|---|---|---|---|---|---|
| Control 1 | 87 μl | — | — | 2 μl | 11 μl | — |
| Control 2 | 87 μl | — | 1 μl | 2 μl | 10 μl | — |
| Control 3 | 87 μl | 10 μl | — | 2 μl | 1 μl | — |
| Control 4 | 87 μl | — | — | — | 11.2 μl | 1.8 μl |

duced THCA, CBDA and CBCA is shown in FIG. 4. CBGA and CBCA (Sigma-Aldrich, Cat. no. C-142 and C-150, respectively) as well as THCA were used as standards (THC Pharm, Frankfurt am Main, Germany, Cat. no. THC-1298).

Er:THCAS, erV:THCAS and er:CBDAS heterologous produced in *N. benthamiana* are capable of producing more than one product. Since the CBDAS protein sequence share a high homology to the THCAS (83%) and the CBCAS (82%) (Page et al., (2015), (WO 2015/196275 A1), all known cannabinoid forming oxidoreductases might be derived from a common ancestor. Thus, it is not surprising that the enzymes exhibit an overlapping product specificity.

Example 5 Endogenously Produced CBGA Functions as a Substrate for THCA/CBCA Production After it had been shown that various plant species possess an endogenous prenyltransferase, which is capable of producing CBGA, the next step was to investigate whether endogenously produced CBGA also functions as a substrate for CBCA production. Therefore, *N. benthamiana* was co-transformed with *A. tumefaciens* strain EHA105, harboring THCA genes coding for a synthase (GB2α1_P35S:er:THCAS:6×:His:TNos) and P19. As negative controls, *N. benthamiana* wildtype (WT) plants or *N. benthamiana* solely transformed with *A. tumefaciens* strain EHA105, harboring the pBIN61-P19 plasmid were used. Transformation and co-transformation were carried out as described in Example 2. Total soluble proteins were extracted from plant leaves and subsequently subjected to prenyltransferase activity assays as described in Example 3. Furthermore, metabolites were analyzed via HPLC-MS as described in Example 3. Detected metabolites were screened in the negative SIM mode for a mass of 357 g/mol which corresponds to the masses of both THCA and CBCA (358 g/mol)—the two products formed by THCAS (Geissler et al., Biotechnol lett. (2018), 40 (6): 981-987.). CBCA standard was purchased from Sigma-Aldrich (Cat. no. C-150). The experimental results are shown in FIG. 5, revealing that heterologous produced THCAS is active in *N. benthamiana* and uses endogenously produced CBGA as its substrate.

Example 6 Impact of Solvent on Product Specificity

It was observed that heterologous produced er:THCAS and er:CBDAS are capable of producing more than one product (Example 4). It was assumed that this could be due to the presence of solvent in the assay mixture which may then alter the product specificity of the enzyme.

*N. benthamiana* plants were transiently transformed with *A. tumefaciens* strain EHA105, harboring genes coding either for er:THCAS, er:CBDAS or er:CBCAS as described in Example 2. After five days of incubation, plants were harvested, and TSP was extracted. Therefore, 150 mg of frozen transformed *N. benthamiana* plant material was homogenized in 500 μL of THCAS/CBDAS/CBCAS reaction buffer (100 mM trisodium citrate, pH 5.5) and centrifuged (17,000×g, 15 min). Thereupon, in vitro activity assays were performed with the addition of different amounts of acetonitrile into the mixture. The reaction mixtures contained 92.8 μL of TSP as well as 0.05 mM of cannabigerolic acid and the appropriate solvent in the range of 1.8-7.2% (v/v) in a total volume of 100 μL buffered in THCAS/CBDAS/CBCAS reaction buffer (100 mM trisodium citrate, pH 5.5). The reaction took place for 2 h at 37° C. To terminate the reaction, 275 μL of ice-cold acetonitrile was added, followed by incubation on ice for 30 min. Finally, the supernatants were purified two times from solid particles by centrifugation (17,000×g, 30 min, 4° C.). Assays were performed in four replicates. THCA, CBCA and CBDA were analyzed by using the HPLC-MS method described in Example 3. For quantification of enzyme activity, the amount of formed product was quantified by peak integration at the wavelength of 260 nm and subsequent conversion from area counts into fkat $$g_{FW}^{-1}$$

by means of serial standard dilutions (THCA 800 nM-0.05 mM; CBDA 800 nM-0.05 mM; CBCA 6.0 nM-0.05 mM).

Production of THCA, CBDA and CBCA in crude plant extract dependent on assay mixture is shown in FIG. 6. In case of er:THCAS and er:CBDAS, increasing amounts of acetonitrile from 1.8% (v/v) up to 7.2% (v/v) changed the product specificity of the aforementioned enzymes from THCA to CBCA.

Example 7 Product Specificity is Dependent on Solvent and not Protein Artifacts in Plant Extract To further examine whether the change in product specificity was indeed catalyzed by the addition of the solvent and not an artifact due to other tobacco proteins still present in the crude extract, THCAS, CBDAS and CBCAS were heterologous produced in *N. benthamiana* as described in Example 2 and isolated via IMAC. Therefore, leaves were cut from plants 4-7 days post transformation and homogenized with 2.5 mL Buffer A (50 mM $NaH_2PO_4$, 10 mM Tris/HCl PH 8.0, 200 mM NaCl per gram leaf material. Subsequently, 1 mM 4-(2-aminoethyl)benzenesulfonyl fluoride hydrochloride (AEBSF, Sigma-Aldrich, Cat. no. A8456) was added to the buffer. After two times 15 min centrifugation and one centrifugation step of 30 min at 14,600×g and 4° C., the supernatant was filtered through a ROTILABO® syringe filter (PVDF, 0.45 μm; Carl Roth, Cat. no. P667.1). Afterwards, it could be used for protein purification by immobilized metal ion affinity chromatography (IMAC).

Protino Columns (Macherey-Nagel GmbH & Co. KG, Düren, Germany, Cat. no. 745250.10) containing 1.5 g Ni-TED Resin (Macherey-Nagel GmbH & Co. KG, Cat. no. 745200.5) were used and gravity-purification was performed. The Column was equilibrated with 12 ml of Buffer A. Afterwards, the crude lysate was applied onto the column. Flow through was collected and stored till analysis at 4° C. After binding, the resin was washed two times with 12 ml Buffer A. The elution of polyhistidine-tagged proteins took place in three steps using 9 mL Buffer A containing increasing concentrations of imidazole (50 mM, 150 mM and 250 mM). All collected fractions were analyzed for the presence of the proteins of interest by SDS-PAGE and subsequent Coomassie Brilliant Blue staining (Saambrook and Russell, 2001).

After the protein purification corresponding elution fractions were combined, desalted and concentrated with Vivaspin® Turbo 15 ultrafiltration device (Sartorius AG, Göttingen, Germany, Cat. no. VS15T21). The protein solution was concentrated to a total volume of 2 mL, followed by three times washing with 9 ml of THCAS/CBCAS/CBDAS buffer (100 mM trisodium citrate, pH 5.5). After the final concentration of the sample to 500-1,000 μL, protein quantity was determined with 'BCA Protein Assay Kit' (Thermo Fisher Scientific, Waltham, MA, USA, Cat. no. 23227) using bovine serum albumin (BSA) as a standard in the range of 0.025-2 mg/mL. The purified proteins were analyzed by SDS-PAGE and visualized by silver nitrate staining as shown in FIG. 7, proving the successful purification of the approximately 80 kDA sized oxidocyclases.

The purified proteins were then used for activity assays with addition of different non-aqueous solvents. Reaction mixtures contained 1.25 μg of er:THCAS, 2.5 μg of er:CBDAS or 2.5 μg of er:CBCAS as well as 0.05 mM of CBGA (Sigma Aldrich, Cat. no. C-142) and an appropriate solvent in the range of 1.8-7.2% (v/v) in a total volume of 100 μL buffered in THCAS/CBDAS/CBCAS reaction buffer (100 mM trisodium citrate, pH 5.5). The reaction took place for 2 h at 37° C. To terminate the reactions, 275 μL of ice-cold acetonitrile was added, followed by incubation on ice for 30 min. Finally, the supernatants were purified two times from solid particles by centrifugation (17,000×g, 30 min, 4° C.). Assays were performed in four replicates. THCA, CBCA and CBDA were analyzed by using the HPLC-MS method described in Example 3. For quantification of enzyme activity, the amount of formed product was quantified by peak integration at the wavelength of 260 nm and subsequent conversion from area counts into pkat $mg^{-1}$ of purified protein by means of serial standard dilutions (THCA 800 nM-0.05 mM; CBDA 800 nM-0.05 mM; CBCA 6.0 nM-0.05 mM).

The production of THCA, CBCA and CBDA by purified er:THCAS, er:CBDAS or er:CBCAS depending on addition of different solvents is shown in FIG. 8. Also with purified er:THCAS and er:CBDAS, the addition of different non-aqueous solvents changed the product specificity from THCA to CBCA. A quantification of the ratios between THCA and CBCA production can be derived from Table 2-3.

Example 8 CBGA Production by Endogenous Prenyltransferases of *N. benthamiana* Seems to be Catalyzed by Soluble as Well as Membrane-Bound Enzymes To examine whether the prenyltransferases are soluble proteins or fragments of membranes which have not sedimented at the centrifugation speed of 17,000×g used in the previous experiments, density gradient centrifugation with higher speed was performed. Therefore, 2.5 g of wild-type *N. benthamiana* leaf material were homogenized in 25 mL of CBGA assay buffer (50 mM Tris/HCl, 10 mM NaCl, pH 7.5) utilizing an ULTRA-TURRAX T 18 basic (IKA-Werke, Staufen in Breisgau, Germany). The homogenate was filtered through one layer of miracloth (Merck Millipore, Cat. no. 475855) and centrifuged at 4° C. for 1 h and 38,000×g. After centrifugation, the supernatant was transferred into a new tube and the pellet was resuspended in 10 mL of CBGA assay buffer. Both, the supernatant and the resolved pellet were then used for prenyltransferase activity assays and subjected to HPLC-MS analysis as described in Example 3. As shown in FIG. 9, production of CBGA could be confirmed in prenyltransferase assays utilizing the supernatant and the resolved pellet, indicating that there could be both soluble as well as membrane-bound enzymes present, which can catalyze the prenylation of olivetolic acid to yield CBGA.

TABLE 2

Alteration of the ratios of THCA to CBCA produced by er:THCAS with non-aqueous solvents applied to the assay mixtures.
er:THCAS

| Solvent | ACN THCA:CBCA | Aceton THCA:CBCA | DCM THCA:CBCA | Isopropanol THCA:CBCA | EtOH THCA:CBCA | DMSO THCA:CBCA | MeOH THCA:CBCA |
|---|---|---|---|---|---|---|---|
| 1.8% (v/v) | 5.7:1 | 11:1 | Only THCA | 13.7:1 | 15.8:1 | 15.4:1 | 13.8:1 |
| 3.6% (v/v) | 3:1 | 7:1 | 4.5:1 | 7.8:1 | 10.7:1 | 11.6:1 | 11:1 |
| 5.4% (v/v) | 1.6:1 | 3.1:1 | 2.6:1 | 5.4:1 | 7.8:1 | 8.2:1 | 9:1 |
| 7.2% (v/v) | 1:1.5 | 1.6:1 | 2.9:1 | 3.8:1 | 5.7:1 | 5.8:1 | 6.8:1 |

TABLE 3

Alteration of the ratios of CBDA to CBCA produced by er:CBDAS with non-aqueous solvents applied to the assay mixtures.
er:CBDAS

| Solvent | ACN CBDA:CBCA | Aceton CBDA:CBCA | DCM CBDA:CBCA | Isopropanol CBDA:CBCA | EtOH CBDA:CBCA | DMSO CBDA:CBCA | MeOH CBDA:CBCA |
|---|---|---|---|---|---|---|---|
| 1.8% (v/v) | 3.5:1 | 2.7:1 | 3.8:1 | 2.3:1 | 3.4:1 | 2.4:1 | 2.8:1 |
| 3.6% (v/v) | 2.3:1 | 1.3:1 | 3.9:1 | 1:1 | 2.6:1 | 1:1 | 2.7:1 |
| 5.4% (v/v) | 1:1 | 1:6.5 | 2.6:1 | 1:2.3 | 1.7:1 | 1:9 | 2.5:1 |
| 7.2% (v/v) | Only CBCA | Only CBCA | 2.3:1 | Only CBCA | 1.2:1 | Only CBCA | 1.8:1 |

The invention claimed is:

1. A process for the production of cannabigerolic acid (CBGA), comprising reacting a plant extract having prenyltransferase activity with olivetolic acid (OA), and geranyl pyrophosphate (GPP) having the following Formula (III)

Formula (III)

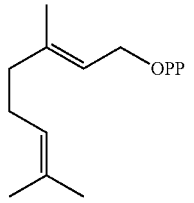

wherein PP represents pyrophosphate, to produce the CBGA, wherein the plant extract is not a *Cannabis sativa* plant extract, and wherein the plant extract is obtained from a plant which expresses an endogenous prenyltransferase.

2. The process of claim 1, wherein the plant is a genetically modified plant expressing a heterologous tetrahydrocannabinolic acid synthase (THCAS; EC 1.21.3.7), cannabidiolic acid synthase (CBDAS; EC 1.21.3.8), and/or cannabichromenic acid synthase (CBCAS; EC 1.3.3.-).

3. The process of claim 1, wherein the plant extract is obtained from solid plant material with an extraction agent to obtain an extraction liquid containing the plant extract dissolved in said extraction liquid.

4. The process of claim 3, wherein the extraction agent is an aqueous buffer selected from the group of TAPS, Bicine, Tricine, TAPSO, HEPES, TES, MOPS, PIPES, Cacodylate, MES, $Na_2HPO_4$, $NaH_2PO_4$, CHES, Acetic acid, Citric acid, Borate, and $KH_2PO_4$.

5. The process of claim 1, wherein the plant extract is a liquid cell culture.

6. The process of claim 1, wherein the plant extract is obtained from a plant selected from the group consisting of *Lactuca sativa, Nepeta cataria, Nicotiana benthamiana, Nicotiana tabacum* and *Ocimum basilicum.*

7. The process of claim 1, further comprising converting the CBGA in the presence of tetrahydrocannabinolic acid synthase (THCAS; EC 1.21.3.7) to delta-9-tetrahydrocannabinolic acid (THCA).

8. The process of claim 7, further comprising decarboxylating the THCA to tetrahydrocannabinol (THC).

9. The process of claim 1, further comprising converting the CBGA in the presence of tetrahydrocannabinolic acid synthase (THCAS; EC 1.21.3.7), cannabidiolic acid synthase (CBDAS; EC 1.21.3.8) and/or cannabichromenic acid synthase (CBCAS; EC 1.3.3.-), to cannabichromenic acid (CBCA).

10. The process of claim 9, further comprising decarboxylating the CBCA to cannabichromene (CBC).

11. The process of claim 1, further comprising converting the CBGA in the presence of cannabidiolic acid synthase (CBDAS; EC 1.21.3.8) to cannabidiolic acid (CBDA).

12. The process of claim 11, further comprising decarboxylating the CBDA to cannabidiol (CBD).

* * * * *

SEQUENCE LISTING

<160> NUMBER OF SEQ ID NOS: 14

<210> SEQ ID NO 1
<211> LENGTH: 1638
<212> TYPE: DNA
<213> ORGANISM: Cannabis sativa
<220> FEATURE:
<223> OTHER INFORMATION: THCAS; EC 1.21.3.7
<300> PUBLICATION INFORMATION:
<308> DATABASE ACCESSION NUMBER: GenBank accession AB057805
<310> PATENT DOCUMENT NUMBER: GenBank version AB057805.1

<400> SEQUENCE: 1

```
atgaattgct cagcattttc cttttggttt gtttgcaaaa taatattttt ctttctctca     60
ttccatatcc aaatttcaat agctaatcct cgagaaaact tccttaaatg cttctcaaaa    120
catattccca acaatgtagc aaatccaaaa ctcgtataca ctcaacacga ccaattgtat    180
atgtctatcc tgaattcgac aatacaaaat cttagattca tctctgatac aaccccaaaa    240
ccactcgtta ttgtcactcc ttcaaataac tcccatatcc aagcaactat tttatgctct    300
aagaaagttg gcttgcagat tcgaactcga agcggtggcc atgatgctga gggtatgtcc    360
tacatatctc aagtcccatt tgttgtagta gacttgagaa acatgcattc gatcaaaata    420
gatgttcata gccaaactgc gtgggttgaa gccggagcta cccttggaga agtttattat    480
tggatcaatg agaagaatga gaatcttagt tttcctggtg ggtattgccc tactgttggc    540
gtaggtggac actttagtgg aggaggctat ggagcattga tgcgaaatta tggccttgcg    600
gctgataata ttattgatgc acacttagtc aatgttgatg gaaaagttct agatcgaaaa    660
tccatgggag aagatctgtt ttgggctata cgtggtggtg gaggagaaaa ctttggaatc    720
attgcagcat ggaaaatcaa actggttgct gtcccatcaa agtctactat attcagtgtt    780
aaaaagaaca tggagataca tgggcttgtc aagttattta acaaatggca aaatattgct    840
tacaagtatg acaaagattt agtactcatg actcacttca taacaaagaa tattacagat    900
aatcatggga agaataagac tacagtacat ggttacttct cttcaatttt tcatggtgga    960
gtggatagtc tagtcgactt gatgaacaag agctttcctg agttgggtat taaaaaaact   1020
gattgcaaag aatttagctg gattgataca accatcttct acagtggtgt tgtaaatttt   1080
aacactgcta attttaaaaa ggaaattttg cttgatagat cagctgggaa gaagacggct   1140
ttctcaatta agttagacta tgttaagaaa ccaattccag aaactgcaat ggtcaaaatt   1200
ttggaaaaat tatatgaaga agatgtagga gctgggatgt atgtgttgta cccttacggt   1260
ggtataatgg aggagatttc agaatcagca attccattcc ctcatcgagc tggaataatg   1320
tatgaacttt ggtacactgc ttcctgggag aagcaagaag ataatgaaaa gcatataaac   1380
tgggttcgaa gtgtttataa ttttacgact ccttatgtgt cccaaaatcc aagattggcg   1440
tatctcaatt atagggacct tgatttagga aaaactaatc atgcgagtcc taataattac   1500
acacaagcac gtatttgggg tgaaaagtat tttggtaaaa attttaacag gttagttaag   1560
gtgaaaacta aagttgatcc caataatttt tttagaaacg aacaaagtat cccacctctt   1620
ccaccgcatc atcattaa                                                 1638
```

<210> SEQ ID NO 2
<211> LENGTH: 1635
<212> TYPE: DNA
<213> ORGANISM: Cannabis sativa
<220> FEATURE:
<223> OTHER INFORMATION: CBDAS; EC 1.21.3.8
<300> PUBLICATION INFORMATION:

<308> DATABASE ACCESSION NUMBER: GenBank accession no: AB292682
<310> PATENT DOCUMENT NUMBER: GenBank version no: AB292682.1

<400> SEQUENCE: 2

```
atgaagtgct caacattctc cttttggttt gtttgcaaga taatattttt ctttttctca     60

ttcaatatcc aaacttccat tgctaatcct cgagaaaact tccttaaatg cttctcgcaa    120

tatattccca ataatgcaac aaatctaaaa ctcgtataca ctcaaaacaa cccattgtat    180

atgtctgtcc taaattcgac aatacacaat cttagattca gctctgacac aaccccaaaa    240

ccacttgtta tcgtcactcc ttcacatgtc tctcatatcc aaggcactat tctatgctcc    300

aagaaagttg gcttgcagat tcgaactcga agtggtggtc atgattctga gggcatgtcc    360

tacatatctc aagtcccatt tgttatagta gacttgagaa acatgcgttc aatcaaaata    420

gatgttcata gccaaactgc atgggttgaa gccggagcta cccttggaga agtttattat    480

tgggttaatg agaaaaatga gagtcttagt ttggctgctg ggtattgccc tactgtttgc    540

gcaggtggac actttggtgg aggaggctat ggaccattga tgagaagcta tggcctcgcg    600

gctgataata tcattgatgc acacttagtc aacgttcatg gaaaagtgct agatcgaaaa    660

tctatggggg aagatctctt ttgggcttta cgtggtggtg gagcagaaag cttcggaatc    720

attgtagcat ggaaaattag actggttgct gtcccaaagt ctactatgtt tagtgttaaa    780

aagatcatgg agatacatga gcttgtcaag ttagttaaca aatggcaaaa tattgcttac    840

aagtatgaca aagatttatt actcatgact cacttcataa ctaggaacat tacagataat    900

caagggaaga ataagacagc aatacacact tacttctctt cagttttcct tggtggagtg    960

gatagtctag tcgacttgat gaacaagagt tttcctgagt tgggtattaa aaaaacggat   1020

tgcagacaat tgagctggat tgatactatc atcttctata gtggtgttgt aaattacgac   1080

actgataatt ttaacaagga aattttgctt gatagatccg ctgggcagaa cggtgctttc   1140

aagattaagt tagactacgt taagaaacca attccagaat ctgtatttgt ccaaattttg   1200

gaaaaattat atgaagaaga tataggagct gggatgtatg cgttgtaccc ttacggtggt   1260

ataatggatg agatttctga atcagcaatt ccattccctc atcgagctgg aatcttgtat   1320

gagttatggt acatatgtag ctgggagaag caagaagata acgaaaagca tctaaactgg   1380

attagaaata tttataactt catgactcct tatgtgtccc aaaatccaag attggcatat   1440

ctcaattata gagaccttga tataggaata aatgatccca agaatccaaa taattacaca   1500

caagcacgta tttggggtga gaagtatttt ggtaaaaatt ttgacaggct agtaaaagtg   1560

aaaaccctgg ttgatcccaa taattttttt agaaacgaac aaagcatccc acctcttcca   1620

cggcatcgtc attaa                                                     1635
```

<210> SEQ ID NO 3
<211> LENGTH: 1638
<212> TYPE: DNA
<213> ORGANISM: Cannabis sativa
<220> FEATURE:
<223> OTHER INFORMATION: CBCAS; EC 1.3.3.-

<400> SEQUENCE: 3

```
atgaattgct caacattctc cttttggttt gtttgcaaaa taatattttt ctttctctca     60

ttcaatatcc aaatttcaat agctaatcct caagaaaact tccttaaatg cttctcggaa    120

tatattccta acaatccagc aaatccaaaa ttcatataca ctcaacacga ccaattgtat    180

atgtctgtcc tgaattcgac aatacaaaat cttagattca cctctgatac aaccccaaaa    240
```

ccactcgtta ttgtcactcc ttcaaatgtc tcccatatcc aggccagtat tctctgctcc 300
aagaaagttg gtttgcagat tcgaactcga agcggtggcc atgatgctga gggtttgtcc 360
tacatatctc aagtcccatt tgctatagta gacttgagaa acatgcatac ggtcaaagta 420
gatattcata gccaaactgc gtgggttgaa gccggagcta cccttggaga agtttattat 480
tggatcaatg agatgaatga gaattttagt tttcctggtg ggtattgccc tactgttggc 540
gtaggtggac actttagtgg aggaggctat ggagcattga tgcgaaatta tggccttgcg 600
gctgataata tcattgatgc acacttagtc aatgttgatg gaaaagttct agatcgaaaa 660
tccatgggag aagatctatt ttgggctata cgtggtggag gaggagaaaa ctttggaatc 720
attgcagcat gtaaaatcaa acttgttgtt gtcccatcaa aggctactat attcagtgtt 780
aaaaagaaca tggagataca tgggcttgtc aagttattta acaaatggca aaatattgct 840
tacaagtatg acaaagattt aatgctcacg actcacttca gaactaggaa tattacagat 900
aatcatggga agaataagac tacagtacat ggttacttct cttccatttt tcttggtgga 960
gtggatagtc tagttgactt gatgaacaag agctttcctg agttgggtat taaaaaaact 1020
gattgcaaag aattgagctg gattgataca accatcttct acagtggtgt tgtaaattac 1080
aacactgcta attttaaaaa ggaaattttg cttgatagat cagctgggaa gaagacggct 1140
ttctcaatta agttagacta tgttaagaaa ctaatacctg aaactgcaat ggtcaaaatt 1200
ttggaaaaat tatatgaaga agaggtagga gttgggatgt atgtgttgta cccttacggt 1260
ggtataatgg atgagatttc agaatcagca attccattcc ctcatcgagc tggaataatg 1320
tatgaacttt ggtacactgc tacctgggag aagcaagaag ataacgaaaa gcatataaac 1380
tgggttcgaa gtgtttataa tttcacaact ccttatgtgt cccaaaatcc aagattggcg 1440
tatctcaatt atagggacct tgatttagga aaaactaatc ctgagagtcc taataattac 1500
acacaagcac gtatttgggg tgaaaagtat tttggtaaaa attttaacag gttagttaag 1560
gtgaaaacca aagctgatcc caataatttt tttagaaacg aacaaagtat cccacctctt 1620
ccaccgcgtc atcattaa 1638

<210> SEQ ID NO 4
<211> LENGTH: 86
<212> TYPE: DNA
<213> ORGANISM: Nicotiana sp.
<220> FEATURE:
<223> OTHER INFORMATION: Er target sequence: endogenous targeting signal of calreticulin from Nicotiana sp
<300> PUBLICATION INFORMATION:
<308> DATABASE ACCESSION NUMBER: GenBank accession XM_009806292
<310> PATENT DOCUMENT NUMBER: version XM_009806292.1

<400> SEQUENCE: 4
gctactcaac gaagggcaaa ccctagctct ctccatctaa ttactgtatt ctctctgctc 60
gtcgctgtcg tatccgccga agtagg 86

<210> SEQ ID NO 5
<211> LENGTH: 95
<212> TYPE: DNA
<213> ORGANISM: Rauvolfia serpentina
<220> FEATURE:
<223> OTHER INFORMATION: ErV target sequence: endogenous targeting signal of strictosidine synthase from Rauvolfia serpentina
<300> PUBLICATION INFORMATION:
<308> DATABASE ACCESSION NUMBER: GenBank accession X62334
<310> PATENT DOCUMENT NUMBER: version X62334.1

<400> SEQUENCE: 5

```
gccaaacttt ctgattcgca aactatggca ctgttcaccg tgttccttct tttcctctcc     60

tcttcgctcg ctctctcctc tccaatcttg aaaga                                95


<210> SEQ ID NO 6
<211> LENGTH: 35
<212> TYPE: DNA
<213> ORGANISM: Artificial Sequence
<220> FEATURE:
<223> OTHER INFORMATION: Forward primer against THCAS from Cannabis
      sativa

<400> SEQUENCE: 6

gcgccgtctc actcgagcca atcctcgaga aaact                                35


<210> SEQ ID NO 7
<211> LENGTH: 60
<212> TYPE: DNA
<213> ORGANISM: Artificial Sequence
<220> FEATURE:
<223> OTHER INFORMATION: Reverse primer against THCAS from Cannabis
      sativa

<400> SEQUENCE: 7

gcgccgtctc gctcgaagct tagtgatggt gatgatgatg cggtggaaga ggtgggatac     60


<210> SEQ ID NO 8
<211> LENGTH: 1601
<212> TYPE: DNA
<213> ORGANISM: Artificial Sequence
<220> FEATURE:
<223> OTHER INFORMATION: thcas:6xhis sequence without the first 84 bp
      and containing the appropriate overhangs for cloning into pUPD

<400> SEQUENCE: 8

gcgccgtctc actcgagcca atcctcgaga aaacttcctt aaatgcttct caaaacatat     60

tcccaacaat gtagcaaatc caaaactcgt atacactcaa cacgaccaat tgtatatgtc    120

tatcctgaat tcgacaatac aaaatcttag attcatctct gatacaaccc caaaaccact    180

cgttattgtc actccttcaa ataactccca tatccaagca actattttat gctctaagaa    240

agttggcttg cagattcgaa ctcgaagcgg tggccatgat gctgagggta tgtcctacat    300

atctcaagtc ccatttgttg tagtagactt gagaaacatg cattcgatca aaatagatgt    360

tcatagccaa actgcgtggg ttgaagccgg agctaccctt ggagaagttt attattggat    420

caatgagaag aatgagaatc ttagttttcc tggtgggtat tgccctactg ttggcgtagg    480

tggacacttt agtggaggag gctatggagc attgatgcga aattatggcc ttgcggctga    540

taatattatt gatgcacact tagtcaatgt tgatggaaaa gttctagatc gaaaatccat    600

gggagaagat ctgttttggg ctatacgtgg tggtggagga gaaaactttg gaatcattgc    660

agcatggaaa atcaaactgg ttgctgtccc atcaaagtct actatattca gtgttaaaaa    720

gaacatggag atacatgggc ttgtcaagtt atttaacaaa tggcaaaata ttgcttacaa    780

gtatgacaaa gatttagtac tcatgactca cttcataaca aagaatatta cagataatca    840

tgggaagaat aagactacag tacatggtta cttctcttca atttttcatg gtggagtgga    900

tagtctagtc gacttgatga acaagagctt tcctgagttg ggtattaaaa aaactgattg    960

caaagaattt agctggattg atacaaccat cttctacagt ggtgttgtaa attttaacac   1020

tgctaatttt aaaaaggaaa ttttgcttga tagatcagct gggaagaaga cggctttctc   1080

aattaagtta gactatgtta agaaaccaat tccagaaact gcaatggtca aaattttgga   1140
```

-continued aaaattatat gaagaagatg taggagctgg gatgtatgtg ttgtaccctt acggtggtat 1200
aatggaggag atttcagaat cagcaattcc attccctcat cgagctggaa taatgtatga 1260
actttggtac actgcttcct gggagaagca agaagataat gaaaagcata taaactgggt 1320
tcgaagtgtt tataatttta cgactcctta tgtgtcccaa aatccaagat tggcgtatct 1380
caattatagg gaccttgatt taggaaaaac taatcatgcg agtcctaata attacacaca 1440
agcacgtatt tggggtgaaa agtattttgg taaaaatttt aacaggttag ttaaggtgaa 1500
aactaaagtt gatcccaata attttttag aaacgaacaa agtatcccac ctcttccacc 1560
gcatcatcat caccatcact aagcttcgag cgagacggcg c 1601

<210> SEQ ID NO 9
<211> LENGTH: 1592
<212> TYPE: DNA
<213> ORGANISM: Artificial Sequence
<220> FEATURE:
<223> OTHER INFORMATION: Cbdas sequence without the first 84 bp and containing the appropriate overhangs for cloning into pUPD

<400> SEQUENCE: 9
ttagtccgtc tcactcgagc caatcctcga gaaaacttcc ttaaatgctt ctcgcaatat 60
attcccaata atgcaacaaa tctaaaactc gtatacactc aaaacaaccc attgtatatg 120
tctgtcctaa attcgacaat acacaatctt agattcacct ctgacacaac cccaaaacca 180
cttgttatcg tcactccttc acatgtctct catatccaag gcactattct atgctccaag 240
aaagttggct tgcagattcg aactcgaagt ggtggtcatg attctgaggg catgtcctac 300
atatctcaag tcccatttgt tatagtagac ttgagaaaca tgcgttcaat caaaatagat 360
gttcatagcc aaactgcatg ggttgaagcc ggagctaccc ttggagaagt ttattattgg 420
gttaatgaga aaaatgagaa tcttagtttg gcggctgggt attgccctac tgtttgcgca 480
ggtggacact ttggtggagg aggctatgga ccattgatga gaaactatgg cctcgcggct 540
gataatatca ttgatgcaca cttagtcaac gttcatggaa aagtgctaga tcgaaaatct 600
atgggggaag atctcttttg ggctttacgt ggtggtggag cagaaagctt cggaatcatt 660
gtagcatgga aaattagact ggttgctgtc ccaaagtcta ctatgtttag tgttaaaaag 720
atcatggaga tacatgagct tgtcaagtta gttaacaaat ggcaaaatat tgcttacaag 780
tatgacaaag atttattact catgactcac ttcataacta ggaacattac agataatcaa 840
gggaagaata agacagcaat acacacttac ttctcttcag ttttccttgg tggagtggat 900
agtctagtcg acttgatgaa caagagtttt cctgagttgg gtattaaaaa aacggattgc 960
agacaattga gctggattga tactatcatc ttctatagtg gtgttgtaaa ttacgacact 1020
gataatttta acaaggaaat tttgcttgat agatccgctg ggcagaacgg tgctttcaag 1080
attaagttag actacgttaa gaaaccaatt ccagaatctg tatttgtcca aattttggaa 1140
aaattatatg aagaagatat aggagctggg atgtatgcgt tgtaccctta cggtggtata 1200
atggatgaga tttcagaatc agcaattcca ttccctcatc gagctggaat cttgtatgag 1260
ttatggtaca tatgtagttg ggagaagcaa gaagataacg aaaagcatct aaactggatt 1320
agaaatattt ataacttcat gactccttat gtgtccaaaa atccaagatt ggcatatctc 1380
aattataggg accttgatat aggaataaat gatcccaaga atccaaataa ttacacacaa 1440
gcacgtattt ggggtgagaa gtattttggt aaaaattttg acaggctagt aaaagtgaaa 1500
accctggttg atcccaataa ctttttaga aacgaacaaa gcatcccacc tcttccacgg 1560
catcgtcatg cagcgagtga gacggttatg at 1592

<210> SEQ ID NO 10
<211> LENGTH: 1595
<212> TYPE: DNA
<213> ORGANISM: Artificial Sequence
<220> FEATURE:
<223> OTHER INFORMATION: Cbcas sequence without the first 84 bp and
containing the appropriate overhangs for cloning into pUPD

<400> SEQUENCE: 10
ttagtccgtc tcactcgagc caatcctcaa gaaaacttcc ttaaatgctt ctcggaatat 60
attcctaaca atccagcaaa tccaaaattc atatacactc aacacgacca attgtatatg 120
tctgtcctga attcgacaat acaaaatctt agattcacct ctgatacaac cccaaaacca 180
ctcgttattg tcactccttc aaatgtctcc catatccagg ccagtattct ctgctccaag 240
aaagttggtt tgcagattcg aactcgaagc ggtggccatg atgctgaggg tttgtcctac 300
atatctcaag tcccatttgc tatagtagac ttgagaaaca tgcatacggt caaagtagat 360
attcatagcc aaactgcgtg ggttgaagcc ggagctaccc ttggagaagt ttattattgg 420
atcaatgaga tgaatgagaa ttttagtttt cctggtgggt attgccctac tgttggcgta 480
ggtggacact ttagtggagg aggctatgga gcattgatgc gaaattatgg ccttgcggct 540
gataatatca ttgatgcaca cttagtcaat gttgatggaa aagttctaga tcgaaaatcc 600
atgggagaag atctattttg ggctatacgt ggtggaggag gagaaaactt tggaatcatt 660
gcagcatgta aaatcaaact tgttgttgtc ccatcaaagg ctactatatt cagtgttaaa 720
aagaacatgg agatacatgg gcttgtcaag ttatttaaca aatggcaaaa tattgcttac 780
aagtatgaca aagatttaat gctcacgact cacttcagaa ctaggaatat tacagataat 840
catgggaaga ataagactac agtacatggt tacttctctt ccatttttct tggtggagtg 900
gatagtctag ttgacttgat gaacaagagc tttcctgagt tgggtattaa aaaaactgat 960
tgcaaagaat tgagctggat tgatacaacc atcttctaca gtggtgttgt aaattacaac 1020
actgctaatt ttaaaaagga aattttgctt gatagatcag ctgggaagaa gacggctttc 1080
tcaattaagt tagactatgt taagaaacta atacctgaaa ctgcaatggt caaaattttg 1140
gaaaaattat atgaagaaga ggtaggagtt gggatgtatg tgttgtaccc ttacggtggt 1200
ataatggatg agatttcaga atcagcaatt ccattccctc atcgagctgg aataatgtat 1260
gaactttggt acactgctac ctgggagaag caagaagata acgaaaagca tataaactgg 1320
gttcgaagtg tttataattt cacaactcct tatgtgtccc aaaatccaag attggcgtat 1380
ctcaattata gggaccttga tttaggaaaa actaatcctg agagtcctaa taattacaca 1440
caagcacgta tttggggtga aaagtatttt ggtaaaaatt ttaacaggtt agttaaggtg 1500
aaaaccaaag ctgatcccaa taattttttt agaaacgaac aaagtatccc acctcttcca 1560
ccgcgtcatc atgcagcgag tgagacggtt atgat 1595

<210> SEQ ID NO 11
<211> LENGTH: 18
<212> TYPE: DNA
<213> ORGANISM: Artificial Sequence
<220> FEATURE:
<223> OTHER INFORMATION: M13 uni THCAS sequencing primer

<400> SEQUENCE: 11
tgtaaaacga cggccagt 18

-continued

```
<210> SEQ ID NO 12
<211> LENGTH: 18
<212> TYPE: DNA
<213> ORGANISM: Artificial Sequence
<220> FEATURE:
<223> OTHER INFORMATION: M13 rev THCAS sequencing primer

<400> SEQUENCE: 12

caggaaacag ctatgacc                                                    18


<210> SEQ ID NO 13
<211> LENGTH: 21
<212> TYPE: DNA
<213> ORGANISM: Artificial Sequence
<220> FEATURE:
<223> OTHER INFORMATION: p35S-Cf3 colony PCR primer

<400> SEQUENCE: 13

ccacgtcttc aaagcaagtg g                                                21


<210> SEQ ID NO 14
<211> LENGTH: 25
<212> TYPE: DNA
<213> ORGANISM: Artificial Sequence
<220> FEATURE:
<223> OTHER INFORMATION: p35S-Cr4 colony PCR primer

<400> SEQUENCE: 14

tcctctccaa atgaaatgaa cttcc                                            25
```